(12) United States Patent
Schwarz et al.

(10) Patent No.: US 10,653,775 B2
(45) Date of Patent: May 19, 2020

(54) **ANTI-GLUCOSAMINIDASE PASSIVE IMMUNIZATION FOR *STAPHYLOCOCCUS AUREUS* INFECTIONS**

(71) Applicant: University of Rochester, Rochester, NY (US)

(72) Inventors: Edward M. Schwarz, Rochester, NY (US); Mark A. Sullivan, Fairport, NY (US); John L. Daiss, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 16/221,442

(22) Filed: Dec. 14, 2018

(65) Prior Publication Data
US 2019/0314501 A1    Oct. 17, 2019

Related U.S. Application Data

(63) Continuation of application No. 15/662,715, filed on Jul. 28, 2017, now Pat. No. 10,179,170, which is a continuation of application No. 13/696,019, filed as application No. PCT/US2011/035033 on May 3, 2011, now Pat. No. 9,737,601.

(60) Provisional application No. 61/330,568, filed on May 3, 2010.

(51) Int. Cl.
| | | |
|---|---|---|
| *A61K 39/40* | (2006.01) | |
| *C07K 16/12* | (2006.01) | |
| *A61F 2/28* | (2006.01) | |
| *A61F 2/30* | (2006.01) | |
| *A61K 45/06* | (2006.01) | |
| *A61K 39/00* | (2006.01) | |

(52) U.S. Cl.
CPC ............ *A61K 39/40* (2013.01); *A61F 2/28* (2013.01); *A61F 2/30* (2013.01); *A61K 45/06* (2013.01); *C07K 16/1271* (2013.01); *A61K 2039/505* (2013.01); *C07K 2317/24* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| 2001/0039038 A1 | 11/2001 | Black et al. |
| 2002/0076766 A1 | 6/2002 | Black et al. |

FOREIGN PATENT DOCUMENTS

| WO | 2009/137677 A2 | 11/2009 |
| WO | 2010/028013 A2 | 3/2010 |
| WO | 2010/039563 A2 | 4/2010 |
| WO | 2011/140114 A2 | 11/2011 |

OTHER PUBLICATIONS

Sugai et al. "Identification of Endo-beta-N-acetylglucosaminidase and N-acetylmuramyl-L-alanine Amidase as Cluster-dispersing Enzymes in *Staphylococcus Aureus*," J. Bacteriol 177:1491-1496 (1995).
Guardati et al. "The Use of Monoclonal Antibodies for Studying the Biological Properties of *Staphylococcus Aureus* Endo-N-acetylglucosaminidase," FEMS Microbiol. Lett. 112:73-79 (1993).
Kuklin et al. "Real-Time Monitoring of Bacterial Infection In Vivo: Development of Bioluminescent Staphylococcal Foreign-Body and Deep-Thigh-Wound Mouse Infection Models," Antimicrob Agents Chemother. 47:2740-2748 (2003).
Brady et al. "Immunoglobulins to Surface-Associated Biofilm Immunogens Provide a Novel Means of Visualization of Methicillin-Resistant *Staphylococcus Aureus* Biofilms," Appl. Env. Micro. 73(20):6612-6619 (2007).
Baba et al. "Targeting of Muralytic Enzymes to the Cell Division Site of Gram-positive Bacteria: Repeat Domains Direct Autolysin to the Equatorial Surface Ring of *Staphylococcus Aureus*," EMBO J. 17:4639-4646 (1998).
International Search Report and Written Opinion for PCT/US11/35033, dated Apr. 9, 2012.
Oshida et al., "A *Staphylococcus aureus* autolysin that has an N-acetylmuramoyl-L-alanine amidase domain and an endo-β_N-acetylglucosaminidase domain: Cloning, sequence analysis, and characterization," Proc. Natl. Acad. Sci. USA, 92: 285-289 (1995).
Li et al., "A Quantitative Mouse Model of Implant-Associated Osteomyelitis and the Kinetics of Microbial Growth, Osteolysis and Humoral Immunity," J. Orthop Res. 26(1): 96-105 (2008).
Guzman et al., "Novel Immunoenzymatic Assay for Identification of Coagulase and Protein A-Negative *Staphylococcus aureus* Strains," Journal of Clinical Microbiology 30(5): 1194-1197 (1992).
Brady et al., "Identification of *Staphylococcus aureus* Proteins Recognized by the Antibody-mediated Immune Response to a Biofilm Infection," Infect. Immun. 74(6):3415-3426 (2006).
Brady et al., "Resolution of *Staphylococcus aureus* Biofilm Infection Using Vaccination and Antibiotic Treatment," Infect. Immun. 79(4):1797-1803 (2011).
Varrone et al., "Anti-glucosaminidase Monoclonal Antibodies as a Passive Immunization for Methicillin-Resistant *Staphylococcus aureus* (MRSA) Orthopedic Infections," IBMS BoneKey 8(4):187-194 (2011).
Varrone et al., "Evaluation of Anti-glucosaminidase Monoclonal Antibodies as a Passive Immunization for Methicillin-resistant *Staphylococcus aureus* (MRSA) Osteomyelitis," 57th Annual Meeting of the Orthopedic Research Society, Jan. 2011.

(Continued)

*Primary Examiner* — Brian Gangle
(74) *Attorney, Agent, or Firm* — Pepper Hamilton LLP

(57) ABSTRACT

The present invention is directed to a monoclonal antibody that binds specifically to a *Staphylococcus aureus* glucosaminidase and inhibits in vivo growth of *S. aureus*. Also disclosed are monoclonal antibody binding portions, recombinant or hybridoma cell lines, pharmaceutical compositions containing the monoclonal antibody or binding portions thereof, and methods of treating *S. aureus* infection and osteomyelitis, and methods for introducing an orthopedic implant into a patient using the monoclonal antibody, binding portion, or pharmaceutical composition of the present invention.

23 Claims, 18 Drawing Sheets

Specification includes a Sequence Listing.

(56) References Cited

OTHER PUBLICATIONS

Kates et al., "Development of a Passive Immunization for Methicillin-resistant *Staphylococcus aureus* (MRSA) Osteomyelitis;" Euro. Cells Mater. 21(Suppl. 2):23 (2011).

Garcia-Lara et al., "Anti-*Staphylococcus aureus* Immunotherapy: Current Status and Prospects," Curr. Opin. Pharma. 9(5):552-557 (2009).

European Search Report for EP11778188.0 dated Apr. 29, 2014.

Vajdos et al., "Comprehensive Functional Maps of the Antigen-Binding Site of an Anti-ErbB2 Antibody Obtained with Shotgun Scanning Mutagenesis," J. Mol. Biol. 320(2)415-428 (2002).

Brown et al., "Tolerance to Single but Not Multiple, Amino Acid Replacements in Antibody VH CDR2,"J. Immunol. 156 (9):3285-91 (1996).

Alignet et al., "*Staphylococcus caprae* Strains Carry Determinants Known to Be Involved in Pathogenicity: a Gene Encoding an Autolysin-binding Fibronectin and the ica Operon Involved in Biofilm Formation," Infection and Immunity 69(2):712-718 (2001).

Francis et al., "Monitoring Bioluminescent *Staphylococcus aureus* Infections in Living Mice Using a Novel luxABCDE Construct," Infection and Immunity 68(6):3594-3600 (2000).

Sugai et al., "Localized Perforation of the Cell Wall by a Major Autolysin: atl Gene Products and the Onset of Penicillin-induced Lysis of *Staphylococcus aureus*," Journal of Bacteriology179(9):2958-2962 (1997).

Extended European Search Report for EP 19187099.7 (dated Apr. 1, 2020).

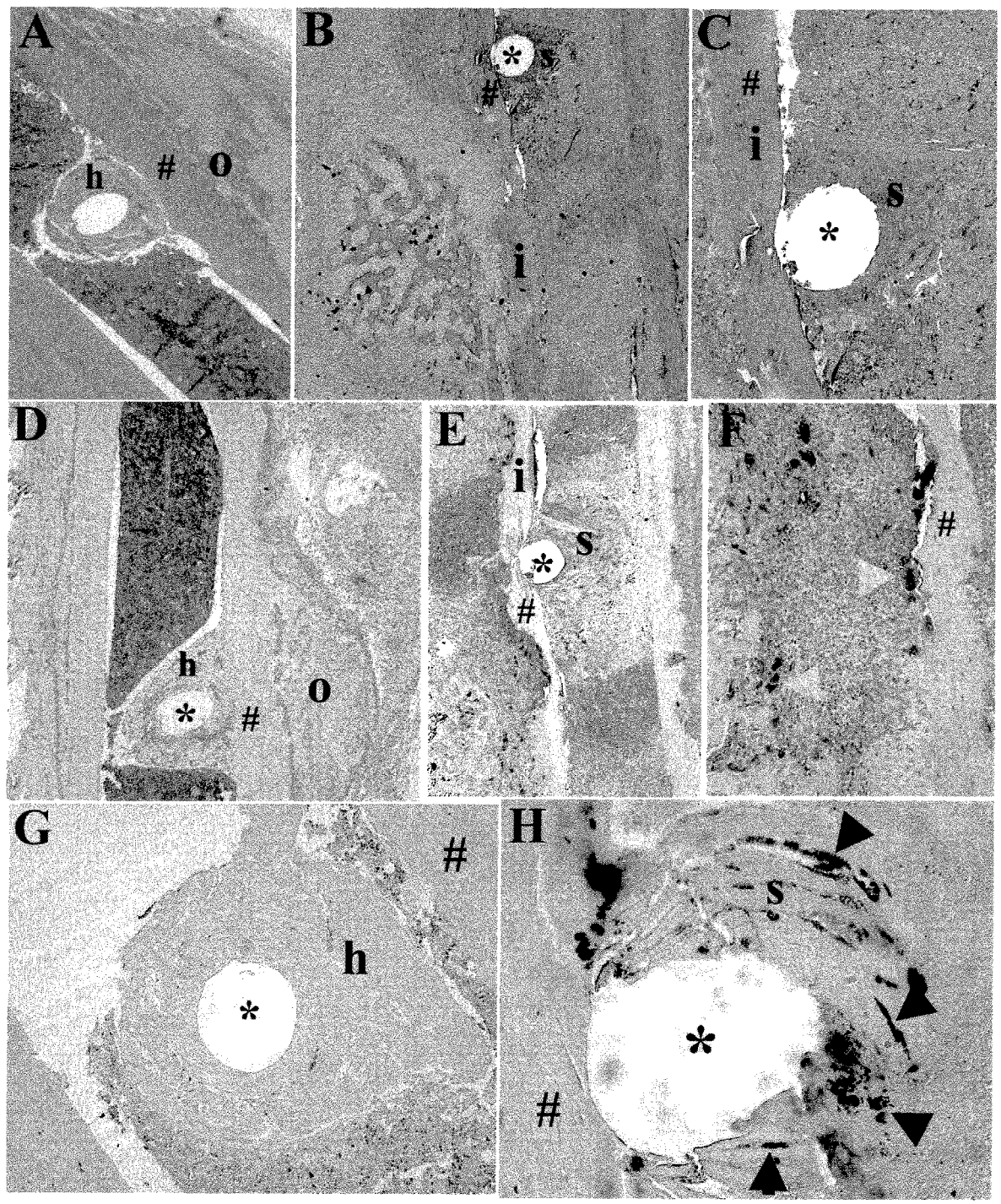
FIGS. 2A-H

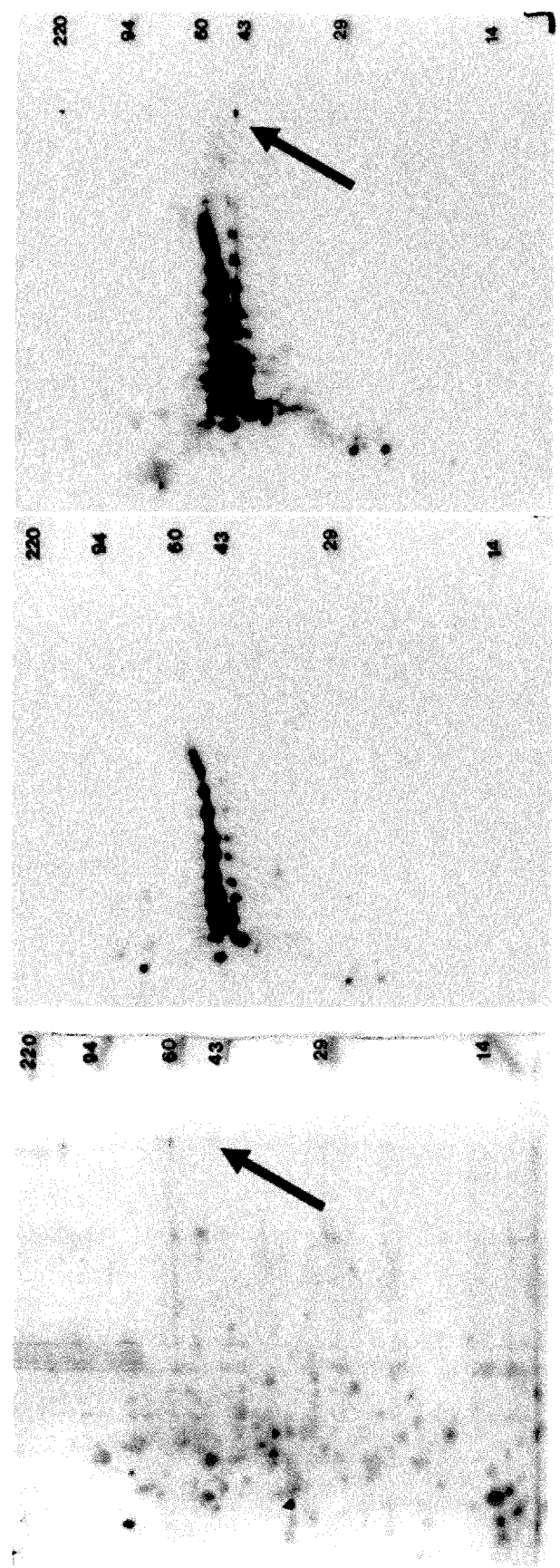

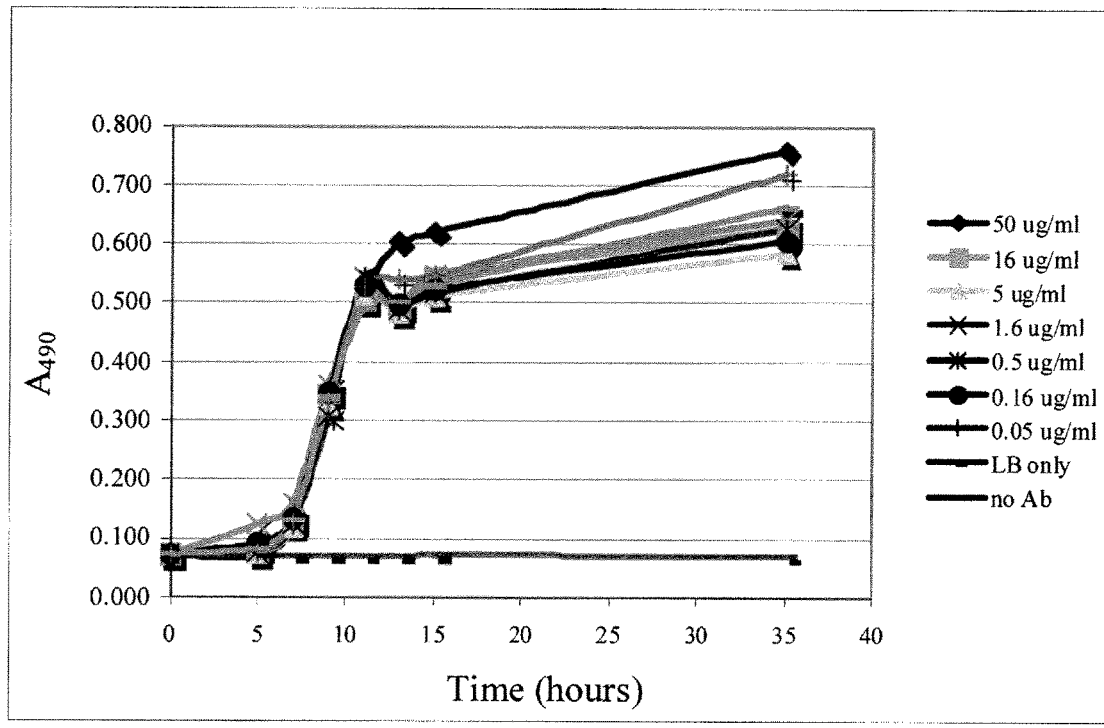

*FIG. 10*

Clustal alignment of four V$_H$ segments
2D11_VH (SEQ ID NO: 1)
3H6_VH  (SEQ ID NO: 2)
1E12_VH (SEQ ID NO: 3)
3A8_VH  (SEQ ID NO: 4)
Consensus (SEQ ID NO: 31)

```
2D11_VH      EVQLQESGPVLVKPGASVKMSCKASGYTFTDYYMNWVKQSHGKSLEWIGVINPYNG--DT  58
3H6_VH       EVQLQESGPVLVKPGASVKLSCKASGYTFTDYFMNWVKQSHGKSLEWIGVINPFNG--GN  58
1E12_VH      EVQLQESGGGFVKPGGSLKLSCAASGFTFSTYVMSWVRQTPEKRLEWVATISDGGG--HT  58
3A8_VH       EVQLQESGGGLVQPGGSMKLSCAASGFTFSDAWMDWVRQSPEKGLEWVAEIKDKTNNHAT  60
             *******  :.:**.*:*:**.***::**   *.**:*: * ***:.  *.        .

Consensus    EVQLQESGXXXVXPGXSXKXSCXASGXTFXXXXMXWVXQXXXKXLEWXXXXIXXXXXXXX

2D11_VH      TYSQKFKGKATLTVDKSSSTAYMELNSLTSEDSAVYYCAR-NYD---EYFDVWGTGTTVT 114
3H6_VH       RYNQNFKGKATLTVDKSSSTAYMELNSLTSEDSAVYYCARGDYDS--PWFDYWGQGTLVT 116
1E12_VH      YYLDNVKGRFTISRDNAKNNLYLHMSHLKSEDTAMYYCARAYYGSSYDAMDYWGQGTSVT 118
3A8_VH       YYAESVKGRFTISRDVSKSRVFLQMNSLRPEDTGIYYCTSGPY----FDYWGQGTTLT 114
              *   .**: *::  *  ..    ::.:.  * .**:.:***:      :* ** ** :*

Consensus    XYXXXXKGXXTXXXDXXXXXXXXXXXXLXXEDXXXYYCXXXXYXXXXXXXDXWGXGTXXT

2D11_VH      VSSAKTTPPSVYPLAPGSAAQTNSMVTLGCXVKG----- 148
3H6_VH       VSAAKTTPPSVYPLAPGSAAQTNSMVTLGCLVKGYSXSQ 155
1E12_VH      VSSAKTTPPSVYPLAPGSAAQTNSMVTLGCLVKG----- 152
3A8_VH       VSSAKTTPPSVYPLAPGSAAQTNSMVTLGCLVKGYFPE- 152
             **:**************************** ***

Consensus    VSXAKTTPPSVYPLAPGSAAQTNSMVTLGCXVKGXXXXX
``` where "X" is any amino acid residue or a deletion of amino acid residue.

*FIG. 11*

Clustal alignment of $V_L$ segments
1E12 (SEQ ID NO: 10)
2D11 (SEQ ID NO: 8)
Consensus (SEQ ID NO: 32)

```
1E12        DIVITQSPAIMSASLGERVTMTCTASSSVSSSYLHWYQQKPGSSPKXWIYSTSNLASGVP 60
2D11        DIVMTQSPAIMSASPGEKVTMTCSASSSVS--YMYWYQQKPGSSPRLLIYDTSNLASGVP 58
            ***:********** **:*****:******  *:;**********:  **.********
Consensus   DIVXTQSPAIMSASXGEXVTMTCXASSSVSXXYXXWYQQKPGSSPXXXIYXTSNLASGVP 1E12        ARFSGSGSGTSYSLTISSMEAEDAATYYCHQYHRSPWTFGGGT 103
2D11        VRFSGSGSGTSYSLTISRMEAEDAATYYCQQWSSYPLTFG--- 98
            .***************** ***********.*:   *  ***
Consensus   XRFSGSGSGTSYSLTISXMEAEDAATYYCXQXXXXPXTFGXXX
``` where "X" is any amino acid residue or a deletion of amino acid residue.

FIG. 12

Clustal alignment of all $V_H$ segments
2D11_VH (SEQ ID NO: 1)
3H6_VH  (SEQ ID NO: 2)
1E12_VH (SEQ ID NO: 3)
3A8_VH  (SEQ ID NO: 4)
1C11_VH (SEQ ID NO: 5)
Consensus (SEQ ID NO: 6)

```
1E12_VH     EVQLQESGGGFVKPGGSLKLSCAASGFTFSTYVMSWVRQTPEKRLEWVATISDGGG--HT 58
3A8_VH      EVQLQESGGGLVQPGGSMKLSCAASGFTFSDAWMDWVRQSPEKGLEWVAEIKDKTNNHAT 60
2D11_VH     EVQLQESGPVLVKPGASVKMSCKASGYTFTDYYMNWVKQSHGKSLEWIGVINPYNG--DT 58
3H6_VH      EVQLQESGPVLVKPGASVKLSCKASGYTFTDYFMNWVKQSHGKSLEWIGVINPFNG--GN 58
1C11_VH     QIQLVQSGPELKKPGETVKISCKASGYTFTTYGMSWVNQAPGKGLKWMGWINTYSG--VP 58
            :;** :**   : ** ::*:** ***.**:    *.**.*:  * *:*:..  *.    .
Consensus   XXQLXXSGXXXXXPGXXXKXSCXASGXTFXXXXMXWVXQXXXKXLXWXXXIXXXXXXXXX 1E12_VH     YYLDNVKGRFTISRDNAKNNLYLHMSHLKSEDTAMYYCARAYYGS-SYDAMDYWGQGTSV 117
3A8_VH      YYAESVKGRFTISRDVSKSRVFLQMNSLRPEDTGIYYCTSGPY-------FDYWGQGTTL 113
2D11_VH     TYSQKFKGKATLTVDKSSSTAYMELNSLTSEDSAVYYCAR-NYD----EYFDVWGTGTTV 113
3H6_VH      RYNQNFKGKATLTVDKSSSTAYMELNSLTSEDSAVYYCARGDYDS---PWFDYWGQGTLV 115
1C11_VH     TYADDFKGRFVFSLETSASTAYLQINNLKNEDTATYFCAREEYSSGYAAWFPYWGQGTLV 118
             * :..**:  .::  :  .   ::.:.  *   **:.  *:*:     *    ** ** :
Consensus   XYXXXXKGXXXXXXXXXXXXXXXXXXXXXLXXEDXXXYXCXXXXYXXXXXXXXXWGXGTXX 1E12_VH     TVSSAKTTPPSVYPLAPGSAAQTNSMVTLGCLVKG----- 152
3A8_VH      TVSSAKTTPPSVYPLAPGSAAQTNSMVTLGCLVKGYFPE- 152
2D11_VH     TVSSAKTTPPSVYPLAPGSAAQTNSMVTLGCXVKG----- 148
3H6_VH      TVSAAKTTPPSVYPLAPGSAAQTNSMVTLGCLVKGYSXSQ 155
1C11_VH     TVSA------------------------------------ 122
            ***:
Consensus   TVSXXXXXXXXXXXXXXXXXXXXXXXXXXXXXXXXXXXXX
``` where "X" is any amino acid residue or a deletion of amino acid residue.

FIG. 13

Clustal alignment of all V_L segments

1E12 (SEQ ID NO: 10)
2D11 (SEQ ID NO: 8)
3A8  (SEQ ID NO: 11)
3H6  (SEQ ID NO: 9)
1C11 (SEQ ID NO: 12)
Consensus (SEQ ID NO: 13)

```
1E12_VL      DIVITQSPAIMSASLGERVTMTCTASSSVSSSYLHWYQQKPGSSPKXWIYSTSNLASGVP 60
2D11_VL      DIVMTQSPAIMSASPGEKVTMTCSASSSVS--YMYWYQQKPGSSPRLLIYDTSNLASGVP 58
3A8_VL       DIVMTQSHKFMSTSVGDRVSITCKASQDVS-TAVAWYQQKPGQSPKLLIYWTSTRHTGVP 59
3H6_VL       --QMTQTTSSLSASLGDRVTISCSASQGIS-NYLNWYQQKPDGTVKLLIYYTSSLHSGVP 57
1C11_VL      DIVLTQSPATLSVTPGDSVSLSCRASQSIS-NNLHWYQQKSHESPRLLIEYASRSISGIP 59
             ** :**:     :*.: *: *:::* **..:*   : *****. : :   *   :*   :*:*
Consensus    DIXXTQXXXXXSXXXGXXVXXXCXASXXXSXXXXXWYQQKXXXXXXXXIXXXSXXXGXP 1E12_VL      ARFSGSGSGTSYSLTISSMEAEDAATYYCHQYHRSPWTFGGGT----- 104
2D11_VL      VRFSGSGSGTSYSLTISRMEAEDAATYYCQQWSSYPLTFG-------- 98
3A8_VL       DRFTGSGSGTDFTLTISSVQAKDLALYYCQQHYTTPYTFGGGTKLEIK 107
3H6_VL       SRFSGGGSGTDYSLSISNLEPEDIATYYCQQYSKLPWTFGGGTKLEIK 105
1C11_VL      SRFSGGGSGTDFTLSINSVESEDFGLYFCQQSNSWPLTFGAGTKLELK 107
             **:*.****.::*:*. ::.:*  . *:*:*    * *** **
Consensus    XRFXGXGSGTXXXLXIXXXXXXXDXXXYCXQXXXXPXTFGXGTXXXXX
``` where "X" is any amino acid residue or a deletion of amino acid residue.

FIG. 14A

Clustal alignment of four V_L segments

1E12 (SEQ ID NO: 10)
2D11 (SEQ ID NO: 8)
3A8  (SEQ ID NO: 11)
3H6  (SEQ ID NO: 9)
Consensus (SEQ ID NO: 33)

```
1E12_VL      DIVITQSPAIMSASLGERVTMTCTASSSVSSSYLHWYQQKPGSSPKXWIYSTSNLASGVP 60
2D11_VL      DIVMTQSPAIMSASPGEKVTMTCSASSSVS--YMYWYQQKPGSSPRLLIYDTSNLASGVP 58
3H6_VL       --QMTQTTSSLSASLGDRVTISCSASQGISN-YLNWYQQKPDGTVKLLIYYTSSLHSGVP 57
3A8_VL       DIVMTQSHKFMSTSVGDRVSITCKASQDVST-AVAWYQQKPGQSPKLLIYWTSTRHTGVP 59
             ** :**:     :*:* *:::*:.**..:*   : ******. : :   ** **. :***
Consensus    DIXXTQXXXXXSXSXSXXSXXXSXSSXXXSXXXXXWYQQKPXXXXXXXXIYXTSXXXXGVP 1E12_VL      PARFSGSGSGTSYSLTISSMEAEDAATYYCHQYHRSPWTFGGGT----- 104
2D11_VL      PVRFSGSGSGTSYSLTISRMEAEDAATYYCQQWSSYPLTFG-------- 98
3H6_VL       PSRFSGGGSGTDYSLSISNLEPEDIATYYCQQYSKLPWTFGGGTKLEIK 105
3A8_VL       PDRFTGSGSGTDFTLTISSVQAKDLALYYCQQHYTTPYTFGGGTKLEIK 107
             * **:*.****.::*:**   :::*  * ***:*    * ******
Consensus    PXRFXGXGSGTXXXLXISXXXXXXDXAXYYCXQXXXXPXTFGGGTXXXXX
```

FIG. 14B

Clustal alignment of 1C11 and 3A8 V$_H$ segments
3A8   (SEQ ID NO: 4)
1C11  (SEQ ID NO: 5)
Consensus (SEQ ID NO: 7)

```
1C11_VH      QIQLVQSGPELKKPGETVKISCKASGYTFTTYGMSWVNQAPGKGLKWMGWIN--TYSGVP  58
3A8_VH       EVQLQESGGGLVQPGGSMKLSCAASGFTFSDAWMDWVRQSPEKGLEWVAEIKDKTNNHAT  60
             ::**.:**   *.:**.::*:**.***:**.  *.**.*:*.***:*:. *:  *...
Consensus    XXQLXXSGXXLXXPGXXXKXSCXASGXTFXXXXMXWVXQXPXKGLXWXXXIXXXTXXXXX 1C11_VH      TYADDFKGRFVFSLETSASTAYLQINNLKNEDTATYFCAREEYSSGYAAWFPYWGQGTLV  118
3A8_VH       YYAESVKGRFTISRDVSKSRVFLQMNSLRPEDTGIYYCT-----SG--PYFDYWGQGTTL  113
             **:..****.:*.:.*.*.*.:**:*.*:.***.*:*:       **  .:*.******.:
Consensus    XYAXXXKGRFXXSXXXSXSXXXLQXNXLXXEDTXXYXCXXXXXXSGXXXXFXYWGQGTXX 1C11_VH      TVSA------------------------------------ 122
3A8_VH       TVSSAKTTPPSVYPLAPGSAAQTNSMVTLGCLVKGYFPE   152
             ***:
Consensus    TVSXXXXXXXXXXXXXXXXXXXXXXXXXXXXXXXXXXXXX
``` where "X" is any amino acid residue or a deletion of amino acid residue.

FIG. 15

Clustal alignment of 1C11 and 3A8 V$_L$ segments
3A8   (SEQ ID NO: 11)
1C11  (SEQ ID NO: 12)
Consensus (SEQ ID NO: 14)

```
1C11_VL      DIVLTQSPATLSVTPGDSVSLSCRASQSISNNLHWYQQKSHESPRLLIEYASRSISGIPS  60
3A8_VL       DIVMTQSHKFMSTSVGDRVSITCKASQDVSTAVAWYQQKPGQSPKLLIYWTSTRHTGVPD  60
             ***:***    :*.: ** **::*:***.:*.. .*****. .**:***:  *:  *.*.
Consensus    DIVXTQSXXXXSXXXGDXVSXXCXASQXXSXXXXWYQQKXXXSPXLLIXXXSXXXXGXPX 1C11_VL      RFSGGGSGTDFTLSINSVESEDFGLYFCQQSNSWPLTFGAGTKLELK  107
3A8_VL       RFTGSGSGTDFTLTISSVQAKDLALYYCQQHYTPYTFGGGTKLEIK   107
             **:*.********:.**:**:..*.**:***     *.* ***.*:*
Consensus    RFXGXGSGTDFTLXIXSVXXXDXXLYXCQQXXXXPXTFGXGTKLEXK
``` where "X" is any amino acid residue or a deletion of amino acid residue.

FIG. 16

```
                                                           CDR1
1C11  H     QIQLVQSGPELKKPGETVKISCKASGYTFT  TYGMS  WVNQAPGKGLKWMG
7-81GL      QVQLVQSGHEVKQPGASVKVSCKASGYSFT  TYGMN  WVPQAPGQGLEWMG
Consenus    QXQLVQSGXEXKXPGXXVKXSCKASGYXFT  TYGMX  WVXQAPGXGLXWMG CDR2
1C11  H     WINTYSGVPTYADDFKG  RFVFSLETSASTAYLQINNLKNEDTATYFCAR
7-81GL      WFNTYTGNPTYAQGFTG  RFVFSMDTSASTAYLQISSLKAEDMAMYYCAR
Consenus    WXNTYXGXPTYAXXFXG  RFVFSXXTSASTAYLQIXXLKXEDXAXYXCAR CDR3
1C11  H     EEYSSGYAAWFP  YWGQGTLVTVSA
7-81GL                    YWGQGTLVTVSA
Consenus    XXXXXXXXXXXX  YWGQGTLVTVSA
                               HJ4
```

FIG. 17A

```
1C11  L     DIVLTQSPATLSVTPGDSVSLSC  RASQSISN  NLHWYQQKSHESPRLLIE
VK6D-21     EIVLTQSPDFQSVTPKEKVTITC  RASQSIGS  SLHWYQQKPDQSPKLLIK
Consenus    XIVLTQSPXXXSVTPXXXVXXXC  RASQSIXX  XLHWYQQXXXXSPXLLIX 1C11  L     YASRSIS  GIPSRFSGGGSGTDFTLSINSVESEDFGLYFC
VK6D-21     YASQSFS  GVPSRFSGSGSGTDFTLTINSLEAEDAATYYC
Consensus   YASXSXS  GXPSRFSGXGSGTDFTLXINSXEXEDXXXYXC 1C11  L     QQSNSWP  LTFGAGTKLELK
VK6D-21     HQSSSLP  LTFGGGTKVEIK
Consensus   XQSXSXP  LTFGXGTKXEXK
                      KJ4
```

FIG. 17B

*FIG. 20A*     *FIG. 20C*
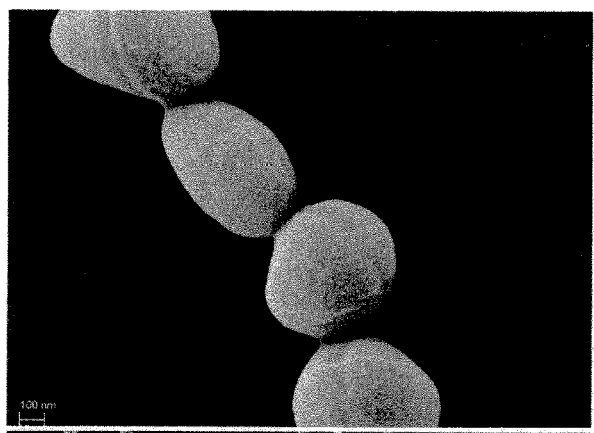 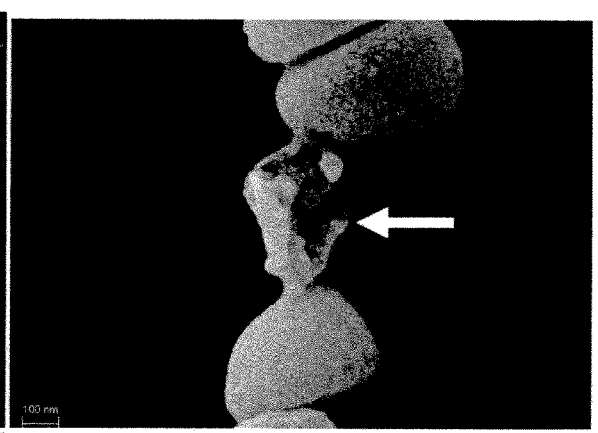
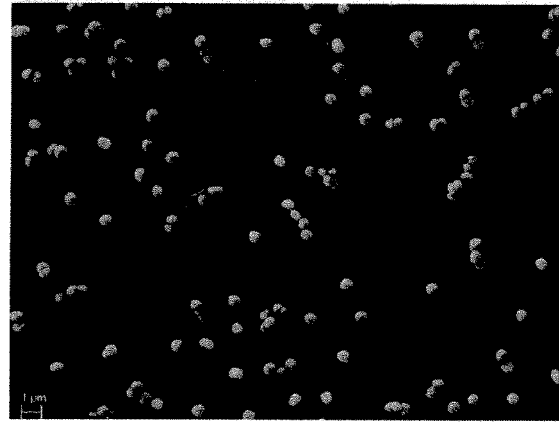 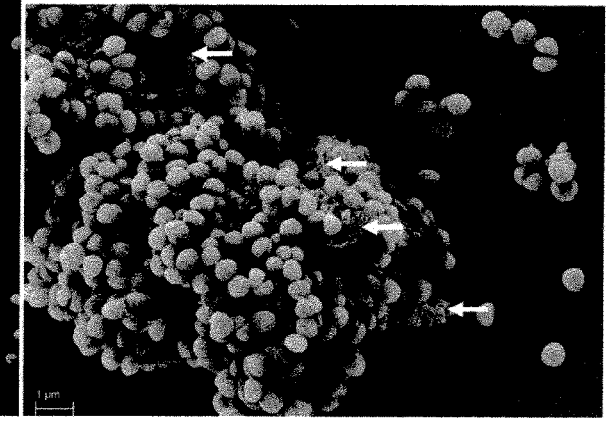
*FIG. 20B*     *FIG. 20D*

SEQUENCE LISTING

```
<160> NUMBER OF SEQ ID NOS: 37

<210> SEQ ID NO 1
<211> LENGTH: 148
<212> TYPE: PRT
<213> ORGANISM: Mus musculus
<220> FEATURE:
<221> NAME/KEY: MISC_FEATURE
<222> LOCATION: (145)..(145)
<223> OTHER INFORMATION: X at position 145 is any amino acid

<400> SEQUENCE: 1

Glu Val Gln Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Thr Tyr Ser Gln Lys Phe
```

```
                    50                  55                  60

Lys Gly Lys Ala Thr Leu Thr Val Asp Lys Ser Ser Thr Ala Tyr
 65                  70                  75                  80

Met Glu Leu Asn Ser Leu Thr Ser Glu Asp Ser Ala Val Tyr Tyr Cys
                     85                  90                  95

Ala Arg Asn Tyr Asp Glu Tyr Phe Asp Val Trp Gly Thr Gly Thr Thr
                100                 105                 110

Val Thr Val Ser Ser Ala Lys Thr Thr Pro Pro Ser Val Tyr Pro Leu
                115                 120                 125

Ala Pro Gly Ser Ala Ala Gln Thr Asn Ser Met Val Thr Leu Gly Cys
                130                 135                 140

Xaa Val Lys Gly
145

<210> SEQ ID NO 2
<211> LENGTH: 155
<212> TYPE: PRT
<213> ORGANISM: Mus musculus
<220> FEATURE:
<221> NAME/KEY: MISC_FEATURE
<222> LOCATION: (153)..(153)
<223> OTHER INFORMATION: X at position 153 is any amino acid

<400> SEQUENCE: 2

Glu Val Gln Leu Gln Glu Ser Gly Pro Val Leu Val Lys Pro Gly Ala
 1               5                  10                  15

Ser Val Lys Leu Ser Cys Lys Ala Ser Gly Tyr Thr Phe Thr Asp Tyr
                20                  25                  30

Phe Met Asn Trp Val Lys Gln Ser His Gly Lys Ser Leu Glu Trp Ile
                35                  40                  45

Gly Val Ile Asn Pro Phe Asn Gly Gly Asn Arg Tyr Asn Gln Asn Phe
                50                  55                  60

Lys Gly Lys Ala Thr Leu Thr Val Asp Lys Ser Ser Ser Thr Ala Tyr
 65                  70                  75                  80

Met Glu Leu Asn Ser Leu Thr Ser Glu Asp Ser Ala Val Tyr Tyr Cys
                     85                  90                  95

Ala Arg Gly Asp Tyr Asp Ser Pro Trp Phe Asp Tyr Trp Gly Gln Gly
                100                 105                 110

Thr Leu Val Thr Val Ser Ala Ala Lys Thr Thr Pro Pro Ser Val Tyr
                115                 120                 125

Pro Leu Ala Pro Gly Ser Ala Ala Gln Thr Asn Ser Met Val Thr Leu
                130                 135                 140

Gly Cys Leu Val Lys Gly Tyr Ser Xaa Ser Gln
145                 150                 155

<210> SEQ ID NO 3
<211> LENGTH: 152
<212> TYPE: PRT
<213> ORGANISM: Mus musculus

<400> SEQUENCE: 3

Glu Val Gln Leu Gln Glu Ser Gly Gly Gly Phe Val Lys Pro Gly Gly
 1               5                  10                  15

Ser Leu Lys Leu Ser Cys Ala Ala Ser Gly Phe Thr Phe Ser Thr Tyr
                20                  25                  30

Val Met Ser Trp Val Arg Gln Thr Pro Glu Lys Arg Leu Glu Trp Val
                35                  40                  45
```

-continued

Ala Thr Ile Ser Asp Gly Gly His Thr Tyr Tyr Leu Asp Asn Val
    50                  55                  60

Lys Gly Arg Phe Thr Ile Ser Arg Asp Asn Ala Lys Asn Asn Leu Tyr
65                  70                  75                  80

Leu His Met Ser His Leu Lys Ser Glu Asp Thr Ala Met Tyr Tyr Cys
                    85                  90                  95

Ala Arg Ala Tyr Tyr Gly Ser Ser Tyr Asp Ala Met Asp Tyr Trp Gly
                100                 105                 110

Gln Gly Thr Ser Val Thr Val Ser Ala Lys Thr Thr Pro Pro Ser
                115                 120                 125

Val Tyr Pro Leu Ala Pro Gly Ser Ala Ala Gln Thr Asn Ser Met Val
130                 135                 140

Thr Leu Gly Cys Leu Val Lys Gly
145                 150

<210> SEQ ID NO 4
<211> LENGTH: 152
<212> TYPE: PRT
<213> ORGANISM: Mus musculus

<400> SEQUENCE: 4

Glu Val Gln Leu Gln Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Lys Asp Lys Thr Asn Asn His Ala Thr Tyr Tyr Ala Glu
    50                  55                  60

Ser Val Lys Gly Arg Phe Thr Ile Ser Arg Asp Val Ser Lys Ser Arg
65                  70                  75                  80

Val Phe Leu Gln Met Asn Ser Leu Arg Pro Glu Asp Thr Gly Ile Tyr
                85                  90                  95

Tyr Cys Thr Ser Gly Pro Tyr Phe Asp Tyr Trp Gly Gln Gly Thr Thr
                100                 105                 110

Leu Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
        130                 135                 140

Leu Val Lys Gly Tyr Phe Pro Glu
145                 150

<210> SEQ ID NO 5
<211> LENGTH: 122
<212> TYPE: PRT
<213> ORGANISM: Mus musculus

<400> SEQUENCE: 5

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
                20                  25                  30

Gly Met Ser Trp Val Asn Gln Ala Pro Gly Lys Gly Leu Lys Trp Met
            35                  40                  45

Gly Trp Ile Asn Thr Tyr Ser Gly Val Pro Thr Tyr Ala Asp Asp Phe
    50                  55                  60

Lys Gly Arg Phe Val Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Glu Glu Tyr Ser Ser Gly Tyr Ala Ala Trp Phe Pro Tyr Trp
            100                 105                 110

Gly Gln Gly Thr Leu Val Thr Val Ser Ala
            115                 120

<210> SEQ ID NO 6
<211> LENGTH: 160
<212> TYPE: PRT
<213> ORGANISM: artificial
<220> FEATURE:
<223> OTHER INFORMATION: Consensus alignment of SEQ ID NOS: 1-5
<220> FEATURE:
<221> NAME/KEY: MISC_FEATURE
<222> LOCATION: (1)..(2)
<223> OTHER INFORMATION: X at position 1 to 2 is any amino acid
<220> FEATURE:
<221> NAME/KEY: MISC_FEATURE
<222> LOCATION: (5)..(6)
<223> OTHER INFORMATION: X at position 5 to 6 is any amino acid
<220> FEATURE:
<221> NAME/KEY: MISC_FEATURE
<222> LOCATION: (9)..(13)
<223> OTHER INFORMATION: X at position 9 to 13 is any amino acid
<220> FEATURE:
<221> NAME/KEY: MISC_FEATURE
<222> LOCATION: (16)..(18)
<223> OTHER INFORMATION: X at position 16 to 18 is any amino acid
<220> FEATURE:
<221> NAME/KEY: MISC_FEATURE
<222> LOCATION: (20)..(20)
<223> OTHER INFORMATION: X at position 20 is any amino acid
<220> FEATURE:
<221> NAME/KEY: MISC_FEATURE
<222> LOCATION: (23)..(23)
<223> OTHER INFORMATION: X at position 23 is any amino acid
<220> FEATURE:
<221> NAME/KEY: MISC_FEATURE
<222> LOCATION: (27)..(27)
<223> OTHER INFORMATION: X at position 27 is any amino acid
<220> FEATURE:
<221> NAME/KEY: MISC_FEATURE
<222> LOCATION: (30)..(33)
<223> OTHER INFORMATION: X at position 30 to 33 is any amino acid
<220> FEATURE:
<221> NAME/KEY: MISC_FEATURE
<222> LOCATION: (35)..(35)
<223> OTHER INFORMATION: X at position 35 is any amino acid
<220> FEATURE:
<221> NAME/KEY: MISC_FEATURE
<222> LOCATION: (38)..(38)
<223> OTHER INFORMATION: X at position 38 is any amino acid
<220> FEATURE:
<221> NAME/KEY: MISC_FEATURE
<222> LOCATION: (40)..(42)
<223> OTHER INFORMATION: X at position 40 to 42 is any amino acid
<220> FEATURE:
<221> NAME/KEY: MISC_FEATURE
<222> LOCATION: (44)..(44)
<223> OTHER INFORMATION: X at position 44 is any amino acid
<220> FEATURE:
<221> NAME/KEY: MISC_FEATURE
<222> LOCATION: (46)..(46)
<223> OTHER INFORMATION: X at position 46 is any amino acid
<220> FEATURE:
<221> NAME/KEY: MISC_FEATURE
<222> LOCATION: (48)..(50)
<223> OTHER INFORMATION: X at position 48 to 50 is any amino acid
<220> FEATURE:
<221> NAME/KEY: MISC_FEATURE
<222> LOCATION: (52)..(61)
<223> OTHER INFORMATION: X at position 52 to 61 is any amino acid

```
<220> FEATURE:
<221> NAME/KEY: MISC_FEATURE
<222> LOCATION: (63)..(66)
<223> OTHER INFORMATION: X at position 63 to 66 is any amino acid
<220> FEATURE:
<221> NAME/KEY: MISC_FEATURE
<222> LOCATION: (69)..(87)
<223> OTHER INFORMATION: X at position 69 to 87 is any amino acid
<220> FEATURE:
<221> NAME/KEY: MISC_FEATURE
<222> LOCATION: (89)..(90)
<223> OTHER INFORMATION: X at position 89 to 90 is any amino acid
<220> FEATURE:
<221> NAME/KEY: MISC_FEATURE
<222> LOCATION: (93)..(95)
<223> OTHER INFORMATION: X at position 93 to 95 is any amino acid
<220> FEATURE:
<221> NAME/KEY: MISC_FEATURE
<222> LOCATION: (97)..(97)
<223> OTHER INFORMATION: X at position 97 is any amino acid
<220> FEATURE:
<221> NAME/KEY: MISC_FEATURE
<222> LOCATION: (99)..(102)
<223> OTHER INFORMATION: X at position 99 to 102 is any amino acid
<220> FEATURE:
<221> NAME/KEY: MISC_FEATURE
<222> LOCATION: (103)..(112)
<223> OTHER INFORMATION: X at position 103 to 112 is any amino acid
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: MISC_FEATURE
<222> LOCATION: (115)..(115)
<223> OTHER INFORMATION: X at position 115 is any amino acid
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: MISC_FEATURE
<222> LOCATION: (118)..(119)
<223> OTHER INFORMATION: X at position 118 to 119 is any amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: MISC_FEATURE
<222> LOCATION: (123)..(159)
<223> OTHER INFORMATION: X at position 123 to 159 is any amino acid
<220> FEATURE:
<221> NAME/KEY: misc_feature
<222> LOCATION: (160)..(160)
<223> OTHER INFORMATION: Xaa can be any naturally occurring amino acid

<400> SEQUENCE: 6

Xaa Xaa Gln Leu Xaa Xaa Ser Gly Xaa Xaa Xaa Xaa Pro Gly Xaa
1               5                   10                  15

Xaa Xaa Lys Xaa Ser Cys Xaa Ala Ser Gly Xaa Thr Phe Xaa Xaa Xaa
                20                  25                  30

Xaa Met Xaa Trp Val Xaa Gln Xaa Xaa Xaa Lys Xaa Leu Xaa Trp Xaa
            35                  40                  45

Xaa Xaa Ile Xaa Xaa Xaa Xaa Xaa Xaa Xaa Xaa Xaa Tyr Xaa Xaa
        50                  55                  60

Xaa Xaa Lys Gly Xaa Xaa Xaa Xaa Xaa Xaa Xaa Xaa Xaa Xaa Xaa
65                  70                  75                  80

Xaa Xaa Xaa Xaa Xaa Xaa Xaa Leu Xaa Xaa Glu Asp Xaa Xaa Xaa Tyr
                    85                  90                  95

Xaa Cys Xaa Xaa Xaa Xaa Tyr Xaa Xaa Xaa Xaa Xaa Xaa Xaa Xaa
                100                 105                 110
```

```
Xaa Trp Gly Xaa Gly Thr Xaa Xaa Thr Val Ser Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

<210> SEQ ID NO 7
<211> LENGTH: 159
<212> TYPE: PRT
<213> ORGANISM: artificial
<220> FEATURE:
<223> OTHER INFORMATION: Consensus alignment of SEQ ID NOS: 4-5
<220> FEATURE:
<221> NAME/KEY: MISC_FEATURE
<222> LOCATION: (1)..(2)
<223> OTHER INFORMATION: X at position 1 to 2 is any amino acid
<220> FEATURE:
<221> NAME/KEY: MISC_FEATURE
<222> LOCATION: (5)..(6)
<223> OTHER INFORMATION: X at position 5 to 6 is any amino acid
<220> FEATURE:
<221> NAME/KEY: MISC_FEATURE
<222> LOCATION: (9)..(10)
<223> OTHER INFORMATION: X at position 9 to 10 is any amino acid
<220> FEATURE:
<221> NAME/KEY: MISC_FEATURE
<222> LOCATION: (12)..(13)
<223> OTHER INFORMATION: X at position 12 to 13 is any amino acid
<220> FEATURE:
<221> NAME/KEY: MISC_FEATURE
<222> LOCATION: (16)..(20)
<223> OTHER INFORMATION: X at position 16 to 20 is any amino acid
<220> FEATURE:
<221> NAME/KEY: MISC_FEATURE
<222> LOCATION: (23)..(23)
<223> OTHER INFORMATION: X at position 23 is any amino acid
<220> FEATURE:
<221> NAME/KEY: MISC_FEATURE
<222> LOCATION: (27)..(27)
<223> OTHER INFORMATION: X at position 27 is any amino acid
<220> FEATURE:
<221> NAME/KEY: MISC_FEATURE
<222> LOCATION: (30)..(33)
<223> OTHER INFORMATION: X at position 30 to 33 is any amino acid
<220> FEATURE:
<221> NAME/KEY: MISC_FEATURE
<222> LOCATION: (35)..(35)
<223> OTHER INFORMATION: X at position 35 is any amino acid
<220> FEATURE:
<221> NAME/KEY: MISC_FEATURE
<222> LOCATION: (38)..(38)
<223> OTHER INFORMATION: X at position 38 is any amino acid
<220> FEATURE:
<221> NAME/KEY: MISC_FEATURE
<222> LOCATION: (40)..(40)
<223> OTHER INFORMATION: X at position 40 is any amino acid
<220> FEATURE:
<221> NAME/KEY: MISC_FEATURE
<222> LOCATION: (42)..(42)
<223> OTHER INFORMATION: X at position 42 is any amino acid
<220> FEATURE:
<221> NAME/KEY: MISC_FEATURE
<222> LOCATION: (46)..(46)
<223> OTHER INFORMATION: X at position 46 is any amino acid
<220> FEATURE:
<221> NAME/KEY: MISC_FEATURE
<222> LOCATION: (48)..(50)
<223> OTHER INFORMATION: X at position 48 to 50 is any amino acid
<220> FEATURE:
<221> NAME/KEY: MISC_FEATURE
<222> LOCATION: (52)..(54)
<223> OTHER INFORMATION: X at position 52 to 54 is any amino acid
<220> FEATURE:
<221> NAME/KEY: MISC_FEATURE
```

```
<222> LOCATION: (56)..(61)
<223> OTHER INFORMATION: X at position 56 to 61 is any amino acid
<220> FEATURE:
<221> NAME/KEY: MISC_FEATURE
<222> LOCATION: (64)..(66)
<223> OTHER INFORMATION: X at position 64 to 66 is any amino acid
<220> FEATURE:
<221> NAME/KEY: MISC_FEATURE
<222> LOCATION: (71)..(72)
<223> OTHER INFORMATION: X at position 71 to 72 is any amino acid
<220> FEATURE:
<221> NAME/KEY: MISC_FEATURE
<222> LOCATION: (74)..(76)
<223> OTHER INFORMATION: X at position 74 to 76 is any amino acid
<220> FEATURE:
<221> NAME/KEY: MISC_FEATURE
<222> LOCATION: (78)..(78)
<223> OTHER INFORMATION: X at position 78 is any amino acid
<220> FEATURE:
<221> NAME/KEY: MISC_FEATURE
<222> LOCATION: (80)..(82)
<223> OTHER INFORMATION: X at position 80 to 82 is any amino acid
<220> FEATURE:
<221> NAME/KEY: MISC_FEATURE
<222> LOCATION: (85)..(85)
<223> OTHER INFORMATION: X at position 85 is any amino acid
<220> FEATURE:
<221> NAME/KEY: MISC_FEATURE
<222> LOCATION: (87)..(87)
<223> OTHER INFORMATION: X at position 87 is any amino acid
<220> FEATURE:
<221> NAME/KEY: MISC_FEATURE
<222> LOCATION: (89)..(90)
<223> OTHER INFORMATION: X at position 89 to 90 is any amino acid
<220> FEATURE:
<221> NAME/KEY: MISC_FEATURE
<222> LOCATION: (94)..(95)
<223> OTHER INFORMATION: X at position 94 to 95 is any amino acid
<220> FEATURE:
<221> NAME/KEY: MISC_FEATURE
<222> LOCATION: (97)..(97)
<223> OTHER INFORMATION: X at position 97 is any amino acid
<220> FEATURE:
<221> NAME/KEY: MISC_FEATURE
<222> LOCATION: (99)..(104)
<223> OTHER INFORMATION: X at position 99 to 104 is any amino acid
<220> FEATURE:
<221> NAME/KEY: MISC_FEATURE
<222> LOCATION: (107)..(110)
<223> OTHER INFORMATION: X at position 107 to 110 is any amino acid
<220> FEATURE:
<221> NAME/KEY: MISC_FEATURE
<222> LOCATION: (112)..(112)
<223> OTHER INFORMATION: X at position 112 is any amino acid
<220> FEATURE:
<221> NAME/KEY: MISC_FEATURE
<222> LOCATION: (119)..(120)
<223> OTHER INFORMATION: X at position 119 to 120 is any amino acid
<220> FEATURE:
<221> NAME/KEY: MISC_FEATURE
<222> LOCATION: (124)..(159)
<223> OTHER INFORMATION: X at position 124 to 159 is any amino acid

<400> SEQUENCE: 7

Xaa Xaa Gln Leu Xaa Xaa Ser Gly Xaa Xaa Leu Xaa Xaa Pro Gly Xaa
1               5                   10                  15

Xaa Xaa Lys Xaa Ser Cys Xaa Ala Ser Gly Xaa Thr Phe Xaa Xaa Xaa
                20                  25                  30

Xaa Met Xaa Trp Val Xaa Gln Xaa Pro Xaa Lys Gly Leu Xaa Trp Xaa
            35                  40                  45

Xaa Xaa Ile Xaa Xaa Xaa Thr Xaa Xaa Xaa Xaa Xaa Tyr Ala Xaa
    50                  55                  60

Xaa Xaa Lys Gly Arg Phe Xaa Xaa Ser Xaa Xaa Ser Xaa Ser Xaa
65                  70                  75              80
```

```
Xaa Xaa Leu Gln Xaa Asn Xaa Leu Xaa Xaa Glu Asp Thr Xaa Xaa Tyr
            85                  90                  95

Xaa Cys Xaa Xaa Xaa Xaa Xaa Ser Gly Xaa Xaa Xaa Xaa Phe Xaa
        100                 105                 110

Tyr Trp Gly Gln Gly Thr Xaa Xaa Thr Val Ser Xaa Xaa Xaa Xaa
        115                 120                 125

Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa
145                 150                 155

<210> SEQ ID NO 8
<211> LENGTH: 98
<212> TYPE: PRT
<213> ORGANISM: Mus musculus

<400> SEQUENCE: 8

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly

<210> SEQ ID NO 9
<211> LENGTH: 105
<212> TYPE: PRT
<213> ORGANISM: Mus musculus

<400> SEQUENCE: 9

Gln Met Thr Gln Thr Thr Ser Ser Leu Ser Ala Ser Leu Gly Asp Arg
1               5                   10                  15

Val Thr Ile Ser Cys Ser Ala Ser Gln Gly Ile Ser Asn Tyr Leu Asn
            20                  25                  30

Trp Tyr Gln Gln Lys Pro Asp Gly Thr Val Lys Leu Leu Ile Tyr Tyr
        35                  40                  45

Thr Ser Ser Leu His Ser Gly Val Pro Ser Arg Phe Ser Gly Gly Gly
    50                  55                  60

Ser Gly Thr Asp Tyr Ser Leu Ser Ile Ser Asn Leu Glu Pro Glu Asp
65                  70                  75                  80

Ile Ala Thr Tyr Tyr Cys Gln Gln Tyr Ser Lys Leu Pro Trp Thr Phe
                85                  90                  95

Gly Gly Gly Thr Lys Leu Glu Ile Lys
            100                 105

<210> SEQ ID NO 10
<211> LENGTH: 103
<212> TYPE: PRT
<213> ORGANISM: Mus musculus
<220> FEATURE:
```

```
<221> NAME/KEY: MISC_FEATURE
<222> LOCATION: (47)..(47)
<223> OTHER INFORMATION: X at position 47 is any amino acid

<400> SEQUENCE: 10

Asp Ile Val Ile Thr Gln Ser Pro Ala Ile Met Ser Ala Ser Leu Gly
1               5                   10                  15

Glu Arg Val Thr Met Thr Cys Thr Ala Ser Ser Val Ser Ser Ser Ser
            20                  25                  30

Tyr Leu His Trp Tyr Gln Gln Lys Pro Gly Ser Ser Pro Lys Xaa Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Trp Thr Phe Gly Gly Gly Thr
            100

<210> SEQ ID NO 11
<211> LENGTH: 107
<212> TYPE: PRT
<213> ORGANISM: Mus musculus

<400> SEQUENCE: 11

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Lys Asp Leu Ala Leu Tyr Tyr Cys Gln Gln His Tyr Thr Thr Pro Tyr
                85                  90                  95

Thr Phe Gly Gly Gly Thr Lys Leu Glu Ile Lys
            100                 105

<210> SEQ ID NO 12
<211> LENGTH: 107
<212> TYPE: PRT
<213> ORGANISM: Mus musculus

<400> SEQUENCE: 12

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Glu Tyr Ala Ser Arg Ser Ile Ser Gly Ile Pro Ser Arg Phe Ser Gly
    50                  55                  60

Gly Gly Ser Gly Thr Asp Phe Thr Leu Ser Ile Asn Ser Val Glu Ser
65                  70                  75                  80
```

Glu Asp Phe Gly Leu Tyr Phe Cys Gln Gln Ser Asn Ser Trp Pro Leu
            85                  90                  95

Thr Phe Gly Ala Gly Thr Lys Leu Glu Leu Lys
            100                 105

<210> SEQ ID NO 13
<211> LENGTH: 108
<212> TYPE: PRT
<213> ORGANISM: artificial
<220> FEATURE:
<223> OTHER INFORMATION: Consensus alignment of SEQ ID NOS: 8-12
<220> FEATURE:
<221> NAME/KEY: MISC_FEATURE
<222> LOCATION: (3)..(4)
<223> OTHER INFORMATION: X at position 3 to 4 is any amino acid or a
      deletion
<220> FEATURE:
<221> NAME/KEY: MISC_FEATURE
<222> LOCATION: (7)..(11)
<223> OTHER INFORMATION: X at position 7 to 11 is any amino acid or a
      deletion
<220> FEATURE:
<221> NAME/KEY: MISC_FEATURE
<222> LOCATION: (13)..(15)
<223> OTHER INFORMATION: X at position 13 to 15 is any amino acid or a
      deletion
<220> FEATURE:
<221> NAME/KEY: MISC_FEATURE
<222> LOCATION: (17)..(18)
<223> OTHER INFORMATION: X at position 17 to 18 is any amino acid or a
      deletion
<220> FEATURE:
<221> NAME/KEY: MISC_FEATURE
<222> LOCATION: (20)..(22)
<223> OTHER INFORMATION: X at position 20 to 22 is any amino acid or a
      deletion
<220> FEATURE:
<221> NAME/KEY: MISC_FEATURE
<222> LOCATION: (24)..(24)
<223> OTHER INFORMATION: X at position 24 is any amino acid or a
      deletion
<220> FEATURE:
<221> NAME/KEY: MISC_FEATURE
<222> LOCATION: (27)..(29)
<223> OTHER INFORMATION: X at position 27 to 29 is any amino acid or a
      deletion
<220> FEATURE:
<221> NAME/KEY: MISC_FEATURE
<222> LOCATION: (31)..(35)
<223> OTHER INFORMATION: X at position 31 to 35 is any amino acid or a
      deletion
<220> FEATURE:
<221> NAME/KEY: MISC_FEATURE
<222> LOCATION: (41)..(48)
<223> OTHER INFORMATION: X at position 41 to 48 is any amino acid or a
      deletion
<220> FEATURE:
<221> NAME/KEY: MISC_FEATURE
<222> LOCATION: (50)..(52)
<223> OTHER INFORMATION: X at position 50 to 52 is any amino acid or a
      deletion
<220> FEATURE:
<221> NAME/KEY: MISC_FEATURE
<222> LOCATION: (54)..(57)
<223> OTHER INFORMATION: X at position 54 to 57 is any amino acid or a
      deletion
<220> FEATURE:
<221> NAME/KEY: MISC_FEATURE
<222> LOCATION: (59)..(59)
<223> OTHER INFORMATION: X at position 59 is any amino acid or a
      deletion
<220> FEATURE:
<221> NAME/KEY: MISC_FEATURE
<222> LOCATION: (61)..(61)
<223> OTHER INFORMATION: X at position 61 is any amino acid or a
      deletion
<220> FEATURE:

```
<221> NAME/KEY: MISC_FEATURE
<222> LOCATION: (64)..(64)
<223> OTHER INFORMATION: X at position 64 is any amino acid or a
      deletion
<220> FEATURE:
<221> NAME/KEY: MISC_FEATURE
<222> LOCATION: (66)..(66)
<223> OTHER INFORMATION: X at position 66 is any amino acid or a
      deletion
<220> FEATURE:
<221> NAME/KEY: MISC_FEATURE
<222> LOCATION: (71)..(73)
<223> OTHER INFORMATION: X at position 71 to 73 is any amino acid or a
      deletion
<220> FEATURE:
<221> NAME/KEY: MISC_FEATURE
<222> LOCATION: (75)..(75)
<223> OTHER INFORMATION: X at position 75 is any amino acid or a
      deletion
<220> FEATURE:
<221> NAME/KEY: MISC_FEATURE
<222> LOCATION: (77)..(82)
<223> OTHER INFORMATION: X at position 77 to 82 is any amino acid or a
      deletion
<220> FEATURE:
<221> NAME/KEY: MISC_FEATURE
<222> LOCATION: (84)..(86)
<223> OTHER INFORMATION: X at position 84 to 86 is any amino acid or a
      deletion
<220> FEATURE:
<221> NAME/KEY: MISC_FEATURE
<222> LOCATION: (88)..(88)
<223> OTHER INFORMATION: X at position 88 is any amino acid or a
      deletion
<220> FEATURE:
<221> NAME/KEY: MISC_FEATURE
<222> LOCATION: (90)..(90)
<223> OTHER INFORMATION: X at position 90 is any amino acid or a
      deletion
<220> FEATURE:
<221> NAME/KEY: MISC_FEATURE
<222> LOCATION: (92)..(95)
<223> OTHER INFORMATION: X at position 92 to 95 is any amino acid or a
      deletion
<220> FEATURE:
<221> NAME/KEY: MISC_FEATURE
<222> LOCATION: (97)..(97)
<223> OTHER INFORMATION: X at position 97 is any amino acid or a
      deletion
<220> FEATURE:
<221> NAME/KEY: MISC_FEATURE
<222> LOCATION: (101)..(101)
<223> OTHER INFORMATION: X at position 101 is any amino acid or a
      deletion
<220> FEATURE:
<221> NAME/KEY: MISC_FEATURE
<222> LOCATION: (104)..(108)
<223> OTHER INFORMATION: X at position 104 to 108 is any amino acid or a
      deletion

<400> SEQUENCE: 13

Asp Ile Xaa Xaa Thr Gln Xaa Xaa Xaa Xaa Ser Xaa Xaa Xaa Gly
1               5                   10                  15

Xaa Xaa Val Xaa Xaa Xaa Cys Xaa Ala Ser Xaa Xaa Xaa Ser Xaa Xaa
                20                  25                  30

Xaa Xaa Xaa Trp Tyr Gln Gln Lys Xaa Xaa Xaa Xaa Xaa Xaa Xaa
            35                  40                  45

Ile Xaa Xaa Xaa Ser Xaa Xaa Xaa Xaa Gly Xaa Pro Xaa Arg Phe Xaa
    50                  55                  60

Gly Xaa Gly Ser Gly Thr Xaa Xaa Xaa Leu Xaa Ile Xaa Xaa Xaa Xaa
65                  70                  75                  80

Xaa Xaa Asp Xaa Xaa Xaa Tyr Xaa Cys Xaa Gln Xaa Xaa Xaa Xaa Pro
                85                  90                  95
```

Xaa Thr Phe Gly Xaa Gly Thr Xaa Xaa Xaa Xaa Xaa
            100                 105

<210> SEQ ID NO 14
<211> LENGTH: 107
<212> TYPE: PRT
<213> ORGANISM: artificial
<220> FEATURE:
<223> OTHER INFORMATION: Consensus alignment of SEQ ID NOS: 11-12
<220> FEATURE:
<221> NAME/KEY: MISC_FEATURE
<222> LOCATION: (4)..(4)
<223> OTHER INFORMATION: X at position 4 is any amino acid or a deletion
<220> FEATURE:
<221> NAME/KEY: MISC_FEATURE
<222> LOCATION: (8)..(11)
<223> OTHER INFORMATION: X at position 8 to 11 is any amino acid or a
      deletion
<220> FEATURE:
<221> NAME/KEY: MISC_FEATURE
<222> LOCATION: (13)..(15)
<223> OTHER INFORMATION: X at position 13 to 15 is any amino acid or a
      deletion
<220> FEATURE:
<221> NAME/KEY: MISC_FEATURE
<222> LOCATION: (18)..(18)
<223> OTHER INFORMATION: X at position 18 is any amino acid or a
      deletion
<220> FEATURE:
<221> NAME/KEY: MISC_FEATURE
<222> LOCATION: (21)..(22)
<223> OTHER INFORMATION: X at position 21 to 22 is any amino acid or a
      deletion
<220> FEATURE:
<221> NAME/KEY: MISC_FEATURE
<222> LOCATION: (24)..(24)
<223> OTHER INFORMATION: X at position 24 is any amino acid or a
      deletion
<220> FEATURE:
<221> NAME/KEY: MISC_FEATURE
<222> LOCATION: (28)..(29)
<223> OTHER INFORMATION: X at position 28 to 29 is any amino acid or a
      deletion
<220> FEATURE:
<221> NAME/KEY: MISC_FEATURE
<222> LOCATION: (31)..(34)
<223> OTHER INFORMATION: X at position 31 to 34 is any amino acid or a
      deletion
<220> FEATURE:
<221> NAME/KEY: MISC_FEATURE
<222> LOCATION: (40)..(42)
<223> OTHER INFORMATION: X at position 40 to 42 is any amino acid or a
      deletion
<220> FEATURE:
<221> NAME/KEY: MISC_FEATURE
<222> LOCATION: (45)..(45)
<223> OTHER INFORMATION: X at position 45 is any amino acid or a
      deletion
<220> FEATURE:
<221> NAME/KEY: MISC_FEATURE
<222> LOCATION: (49)..(51)
<223> OTHER INFORMATION: X at position 49 to 51 is any amino acid or a
      deletion
<220> FEATURE:
<221> NAME/KEY: MISC_FEATURE
<222> LOCATION: (53)..(56)
<223> OTHER INFORMATION: X at position 53 to 56 is any amino acid or a
      deletion
<220> FEATURE:
<221> NAME/KEY: MISC_FEATURE
<222> LOCATION: (58)..(58)
<223> OTHER INFORMATION: X at position 58 is any amino acid or a
      deletion
<220> FEATURE:
<221> NAME/KEY: MISC_FEATURE
<222> LOCATION: (60)..(60)
<223> OTHER INFORMATION: X at position 60 is any amino acid or a

```
                                    -continued
<220> FEATURE:
<221> NAME/KEY: MISC_FEATURE
<222> LOCATION: (63)..(63)
<223> OTHER INFORMATION: X at position 63 is any amino acid or a
      deletion
<220> FEATURE:
<221> NAME/KEY: MISC_FEATURE
<222> LOCATION: (65)..(65)
<223> OTHER INFORMATION: X at position 65 is any amino acid or a
      deletion
<220> FEATURE:
<221> NAME/KEY: MISC_FEATURE
<222> LOCATION: (74)..(74)
<223> OTHER INFORMATION: X at position 74 is any amino acid or a
      deletion
<220> FEATURE:
<221> NAME/KEY: MISC_FEATURE
<222> LOCATION: (76)..(76)
<223> OTHER INFORMATION: X at position 76 is any amino acid or a
      deletion
<220> FEATURE:
<221> NAME/KEY: MISC_FEATURE
<222> LOCATION: (79)..(81)
<223> OTHER INFORMATION: X at position 79 to 81 is any amino acid or a
      deletion
<220> FEATURE:
<221> NAME/KEY: MISC_FEATURE
<222> LOCATION: (83)..(84)
<223> OTHER INFORMATION: X at position 83 to 84 is any amino acid or a
      deletion
<220> FEATURE:
<221> NAME/KEY: MISC_FEATURE
<222> LOCATION: (87)..(87)
<223> OTHER INFORMATION: X at position 87 is any amino acid or a
      deletion
<220> FEATURE:
<221> NAME/KEY: MISC_FEATURE
<222> LOCATION: (91)..(94)
<223> OTHER INFORMATION: X at position 91 to 94 is any amino acid or a
      deletion
<220> FEATURE:
<221> NAME/KEY: MISC_FEATURE
<222> LOCATION: (96)..(96)
<223> OTHER INFORMATION: X at position 96 is any amino acid or a
      deletion
<220> FEATURE:
<221> NAME/KEY: MISC_FEATURE
<222> LOCATION: (100)..(100)
<223> OTHER INFORMATION: X at position 100 is any amino acid or a
      deletion
<220> FEATURE:
<221> NAME/KEY: MISC_FEATURE
<222> LOCATION: (106)..(106)
<223> OTHER INFORMATION: X at position 106 is any amino acid or a
      deletion

<400> SEQUENCE: 14

Asp Ile Val Xaa Thr Gln Ser Xaa Xaa Xaa Xaa Ser Xaa Xaa Xaa Gly
1               5                   10                  15

Asp Xaa Val Ser Xaa Xaa Cys Xaa Ala Ser Gln Xaa Xaa Ser Xaa Xaa
            20                  25                  30

Xaa Xaa Trp Tyr Gln Gln Lys Xaa Xaa Xaa Ser Pro Xaa Leu Leu Ile
        35                  40                  45

Xaa Xaa Xaa Ser Xaa Xaa Xaa Xaa Gly Xaa Pro Xaa Arg Phe Xaa Gly
    50                  55                  60

Xaa Gly Ser Gly Thr Asp Phe Thr Leu Xaa Ile Xaa Ser Val Xaa Xaa
65                  70                  75                  80

Xaa Asp Xaa Xaa Leu Tyr Xaa Cys Gln Gln Xaa Xaa Xaa Xaa Pro Xaa
                85                  90                  95

Thr Phe Gly Xaa Gly Thr Lys Leu Glu Xaa Lys
                100                 105
```

<210> SEQ ID NO 15
<211> LENGTH: 21
<212> TYPE: PRT
<213> ORGANISM: artificial
<220> FEATURE:
<223> OTHER INFORMATION: Primer for S. aureus nuc gene

<400> SEQUENCE: 15

Gly Cys Gly Ala Thr Thr Gly Ala Thr Gly Gly Thr Gly Ala Thr Ala
1               5                   10                  15

Cys Gly Gly Thr Thr
            20

<210> SEQ ID NO 16
<211> LENGTH: 21
<212> TYPE: PRT
<213> ORGANISM: artificial
<220> FEATURE:
<223> OTHER INFORMATION: Primer for S. aureus nuc gene

<400> SEQUENCE: 16

Ala Gly Cys Cys Ala Ala Gly Cys Cys Thr Thr Gly Ala Cys Gly Ala
1               5                   10                  15

Ala Cys Thr Ala Ala
            20

<210> SEQ ID NO 17
<211> LENGTH: 20
<212> TYPE: PRT
<213> ORGANISM: artificial
<220> FEATURE:
<223> OTHER INFORMATION: Primer for mouse b-actin gene

<400> SEQUENCE: 17

Ala Gly Ala Thr Gly Thr Gly Ala Ala Thr Cys Ala Gly Cys Ala Ala
1               5                   10                  15

Gly Cys Ala Gly
            20

<210> SEQ ID NO 18
<211> LENGTH: 20
<212> TYPE: PRT
<213> ORGANISM: artificial
<220> FEATURE:
<223> OTHER INFORMATION: Primer for mouse b-actin gene

<400> SEQUENCE: 18

Gly Cys Gly Cys Ala Ala Gly Thr Thr Ala Gly Gly Thr Thr Thr Thr
1               5                   10                  15

Gly Thr Cys Ala
            20

<210> SEQ ID NO 19
<211> LENGTH: 110
<212> TYPE: PRT
<213> ORGANISM: Homo sapiens

<400> SEQUENCE: 19

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
            35                  40                  45

Gly Trp Phe Asn Thr Tyr Thr Gly Asn Pro Tyr Ala Gln Gly Phe
 50                  55                  60

Thr Gly Arg Phe Val Phe Ser Met Asp Thr Ser Ala Ser Thr Ala Tyr
 65                  70                  75                  80

Leu Gln Ile Ser Ser Leu Lys Ala Glu Asp Met Ala Met Tyr Tyr Cys
                 85                  90                  95

Ala Arg Tyr Trp Gly Gln Gly Thr Leu Val Thr Val Ser Ala
            100                 105                 110

<210> SEQ ID NO 20
<211> LENGTH: 107
<212> TYPE: PRT
<213> ORGANISM: Homo sapiens

<400> SEQUENCE: 20

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Ser Leu Pro Leu
                 85                  90                  95

Thr Phe Gly Gly Gly Thr Lys Val Glu Ile Lys
            100                 105

<210> SEQ ID NO 21
<211> LENGTH: 444
<212> TYPE: DNA
<213> ORGANISM: Mus musculus
<220> FEATURE:
<221> NAME/KEY: misc_feature
<222> LOCATION: (434)..(434)
<223> OTHER INFORMATION: N at position 434 is unknown

<400> SEQUENCE: 21
gaggtgcagc tgcaggagtc tggacctgtg ctggtgaagc ctggggcttc agtgaagatg      60
tcctgtaagg cttctggata cacattcact gactactata tgaactgggt gaagcagagc     120
catggaaaga gccttgagtg gattggagtt attaatcctt acaacggtga tactacctac     180
agccagaagt tcaagggcaa ggccacattg actgttgaca gtcctccag cacagcctac      240 atggagctca cagcctgac atctgaggac tctgcagtct attactgtgc aagaaattac      300
gacgagtact tcgatgtctg gggcacaggg accacggtca ccgtctcctc agccaaaacg     360
acacccccat ctgtctatcc actggcccct ggatctgctg cccaaactaa ctccatggtg     420
accctgggat gccnggtcaa gggc                                            444

<210> SEQ ID NO 22
<211> LENGTH: 294
<212> TYPE: DNA
<213> ORGANISM: Mus musculus

<400> SEQUENCE: 22

```
gatattgtga tgacccagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttatgacaca tccaacctgg cttctggagt ccctgttcgc     180
ttcagtggca gtgggtctgg gacctcttac tctctcacaa tcagccgaat ggaggctgag     240
gatgctgcca cttattactg ccagcagtgg agtagttacc cgctcacgtt cggt           294
```

<210> SEQ ID NO 23
<211> LENGTH: 467
<212> TYPE: DNA
<213> ORGANISM: Mus musculus
<220> FEATURE:
<221> NAME/KEY: misc_feature
<222> LOCATION: (458)..(458)
<223> OTHER INFORMATION: N at position 458 is unknown

<400> SEQUENCE: 23

```
gaggtgcagc tgcaggagtc tggacctgtg ctggtgaagc ctggggcttc agtgaagctg      60
tcctgtaagg cttctggata cacattcact gactacttta tgaactgggt gaagcagagc     120
catggaaaga gccttgagtg gattggagtt attaatcctt caacggtgg taataggtac      180 aaccagaact tcaagggcaa ggccacattg actgttgaca gtcctccag cacagcctac      240 atggagctca acagcctgac atctgaggac tctgcagtct attactgtgc aagaggggac     300
tatgactccc cctggtttga ttactgggc aagggactc tggtcactgt ctctgcagcc      360
aaaacgacac cccatctgt ctatccactg gcccctggat ctgctgccca aactaactcc     420
atggtgaccc tgggatgcct ggtcaagggc tattcccnga gccagtg                   467
```

<210> SEQ ID NO 24
<211> LENGTH: 315
<212> TYPE: DNA
<213> ORGANISM: Mus musculus

<400> SEQUENCE: 24

```
cagatgacac agactacgtc ctccctgtct gcctctctgg agacagagt caccatcagt      60 tgcagtgcaa gtcagggcat tagcaattat ttaaactggt atcagcagaa accagatgga     120
actgttaaac tcctgatcta ttacacatca gtttacact caggagtccc atcaaggttc     180
agtggcggtg gtctgggac agattattct ctctccatca gcaacctgga acctgaagat     240
attgccactt actattgtca gcagtatagt aagcttcctt ggacgttcgg tggaggcacc     300
aagctggaaa tcaaa                                                     315
```

<210> SEQ ID NO 25
<211> LENGTH: 456
<212> TYPE: DNA
<213> ORGANISM: Mus musculus

<400> SEQUENCE: 25

```
gaggtgcagc tgcaggagtc tgggggaggc ttcgtgaagc ctggagggtc cctgaaactc      60
tcctgtgcag cctctggatt cactttcagt acctatgtca tgtcttgggt tcgccagact     120
ccggaaaaga ggctggagtg gtcgcaacc attagtgatg gtggtggtca tacttactat     180
ctagacaatg taagggccg attcaccatc tccagagaca atgccaagaa caacctgtac     240
ctgcacatga gccatctgaa gtctgaggac acagccatgt attactgtgc aagagcttac     300
tacggtagta gttacgacgc tatggactac tggggtcaag gaacctcagt caccgtctcc     360
```

```
tcagccaaaa cgacaccccc atctgtctat ccactggccc ctggatctgc tgcccaaact    420
aactccatgg tgaccctggg atgcctggtc aagggc                             456
```

<210> SEQ ID NO 26
<211> LENGTH: 309
<212> TYPE: DNA
<213> ORGANISM: Mus musculus
<220> FEATURE:
<221> NAME/KEY: misc_feature
<222> LOCATION: (141)..(141)
<223> OTHER INFORMATION: N at position 141 is unknown

<400> SEQUENCE: 26

```
gatattgtga tcacccagtc tccagcaatc atgtctgcat ctctagggga acgggtcacc    60
atgacctgca ctgccagctc aagtgtaagt tccagttact tacactggta ccagcagaag   120
ccaggatcct cccccaaact ntggatttat agcacatcca acctggcttc tggagtccca   180
gctcgcttca gtggcagtgg gtctgggacc tcttactctc tcacaatcag cagcatggag   240
gctgaagatg ctgccactta ttactgccac cagtatcatc gttccccatg gacgttcggt   300
ggaggcacc                                                           309
```

<210> SEQ ID NO 27
<211> LENGTH: 456
<212> TYPE: DNA
<213> ORGANISM: Mus musculus

<400> SEQUENCE: 27

```
gaggtgcagc tgcaggagtc tggaggaggc ttggtgcaac ctggaggatc catgaaactc    60
tcttgtgctg cctctggatt cactttagt gacgcctgga tggactgggt ccgccagtct   120
ccagagaagg ggcttgagtg ggttgctgaa attaaagaca aaactaataa tcatgcaaca   180
tactatgctg agtctgtgaa agggaggttc accatctcaa gagatgtttc caaaagtcgt   240
gtcttcctgc aaatgaacag cttaagacct gaagacactg gcatttatta ctgtacgtct   300
gggccatatt ttgactactg gggccaaggc accactctca cagtctcctc agccaaaacg   360
acacccccat ctgtctatcc actggcccct ggatctgctg cccaaactaa ctccatggtg   420
accctgggat gcctggtcaa gggctatttc cctgag                             456
```

<210> SEQ ID NO 28
<211> LENGTH: 321
<212> TYPE: DNA
<213> ORGANISM: Mus musculus

<400> SEQUENCE: 28

```
gacattgtga tgacccagtc tcacaaattc atgtccacat cagtaggaga cagggtcagc    60
atcacctgca aggccagtca ggacgtgagt actgctgtag cctggtatca acaaaaacca   120
gggcaatctc ctaaactact gatttactgg acatccaccc ggcacactgg agtccctgat   180
cgcttcacag gcagtggatc tgggacagat tttactctca ccatcagcag tgtgcaggct   240
aaagacctgg cactttatta ctgtcagcaa cattatacca ctccgtacac gttcggaggg   300
gggaccaagc tggaaataaa a                                             321
```

<210> SEQ ID NO 29
<211> LENGTH: 366
<212> TYPE: DNA
<213> ORGANISM: Mus musculus

<400> SEQUENCE: 29

```
cagatccagt tggtacagtc tggacctgag ctgaagaagc ctggagagac agtcaagatc    60
tcctgcaagg cttctgggta taccttcaca acgtatggaa tgagctgggt gaatcaggct   120
ccaggaaagg gtttaaagtg gatgggctgg ataaacacct actctggagt gccaacatat   180
gctgatgact tcaagggacg gtttgtcttc tctttggaaa cctctgccag cactgcctat   240
ttgcagatca caacctcaa aaatgaggac acggctacat atttctgtgc aagagaggag    300
tacagctcag gctacgcggc ctggtttcct tactggggcc aagggactct ggtcactgtc   360
tctgca                                                              366
```

<210> SEQ ID NO 30
<211> LENGTH: 321
<212> TYPE: DNA
<213> ORGANISM: Mus musculus

<400> SEQUENCE: 30

```
gatattgtgc taactcagtc tccagccacc ctgtctgtga ctccaggaga tagcgtcagt    60 cttcctgca gggccagcca agtattagc aacaacctac actggtatca acaaaaatca    120
catgagtctc caaggcttct catcgaatat gcttcccggt ccatctctgg gatcccctct   180
aggttcagtg gcggtggatc agggacagat ttcactctca gtatcaacag tgtggagtct   240
gaagattttg gattgtattt ctgtcaacag agtaacagct ggccgctcac gttcggtgct   300
gggaccaagc tggagctgaa a                                            321
```

<210> SEQ ID NO 31
<211> LENGTH: 159
<212> TYPE: PRT
<213> ORGANISM: artificial
<220> FEATURE:
<223> OTHER INFORMATION: Consensus alignment of SEQ ID NOS: 1-4
<220> FEATURE:
<221> NAME/KEY: MISC_FEATURE
<222> LOCATION: (9)..(11)
<223> OTHER INFORMATION: X at position 9 to 11 is any amino acid
<220> FEATURE:
<221> NAME/KEY: MISC_FEATURE
<222> LOCATION: (13)..(13)
<223> OTHER INFORMATION: X at position 13 is any amino acid
<220> FEATURE:
<221> NAME/KEY: MISC_FEATURE
<222> LOCATION: (16)..(16)
<223> OTHER INFORMATION: X at position 16 is any amino acid
<220> FEATURE:
<221> NAME/KEY: MISC_FEATURE
<222> LOCATION: (18)..(18)
<223> OTHER INFORMATION: X at position 18 is any amino acid
<220> FEATURE:
<221> NAME/KEY: MISC_FEATURE
<222> LOCATION: (20)..(20)
<223> OTHER INFORMATION: X at position 20 is any amino acid
<220> FEATURE:
<221> NAME/KEY: MISC_FEATURE
<222> LOCATION: (23)..(23)
<223> OTHER INFORMATION: X at position 23 is any amino acid
<220> FEATURE:
<221> NAME/KEY: MISC_FEATURE
<222> LOCATION: (27)..(27)
<223> OTHER INFORMATION: X at position 27 is any amino acid
<220> FEATURE:
<221> NAME/KEY: MISC_FEATURE
<222> LOCATION: (30)..(33)
<223> OTHER INFORMATION: X at position 30 to 33 is any amino acid
<220> FEATURE:
<221> NAME/KEY: MISC_FEATURE
<222> LOCATION: (35)..(35)
<223> OTHER INFORMATION: X at position 35 is any amino acid
<220> FEATURE:

```
<221> NAME/KEY: MISC_FEATURE
<222> LOCATION: (38)..(38)
<223> OTHER INFORMATION: X at position 38 is any amino acid
<220> FEATURE:
<221> NAME/KEY: MISC_FEATURE
<222> LOCATION: (40)..(42)
<223> OTHER INFORMATION: X at position 40 to 42 is any amino acid
<220> FEATURE:
<221> NAME/KEY: MISC_FEATURE
<222> LOCATION: (44)..(44)
<223> OTHER INFORMATION: X at position 44 is any amino acid
<220> FEATURE:
<221> NAME/KEY: MISC_FEATURE
<222> LOCATION: (48)..(61)
<223> OTHER INFORMATION: X at position 48 to 61 is any amino acid
<220> FEATURE:
<221> NAME/KEY: MISC_FEATURE
<222> LOCATION: (63)..(66)
<223> OTHER INFORMATION: X at position 63 to 66 is any amino acid
<220> FEATURE:
<221> NAME/KEY: MISC_FEATURE
<222> LOCATION: (69)..(70)
<223> OTHER INFORMATION: X at position 69 to 70 is any amino acid
<220> FEATURE:
<221> NAME/KEY: MISC_FEATURE
<222> LOCATION: (72)..(74)
<223> OTHER INFORMATION: X at position 72 to 74 is any amino acid
<220> FEATURE:
<221> NAME/KEY: MISC_FEATURE
<222> LOCATION: (76)..(87)
<223> OTHER INFORMATION: X at position 76 to 87 is any amino acid
<220> FEATURE:
<221> NAME/KEY: MISC_FEATURE
<222> LOCATION: (89)..(90)
<223> OTHER INFORMATION: X at position 89 to 90 is any amino acid
<220> FEATURE:
<221> NAME/KEY: MISC_FEATURE
<222> LOCATION: (93)..(95)
<223> OTHER INFORMATION: X at position 93 to 95 is any amino acid
<220> FEATURE:
<221> NAME/KEY: MISC_FEATURE
<222> LOCATION: (99)..(102)
<223> OTHER INFORMATION: X at position 99 to 102 is any amino acid
<220> FEATURE:
<221> NAME/KEY: MISC_FEATURE
<222> LOCATION: (104)..(110)
<223> OTHER INFORMATION: X at position 104 to 110 is any amino acid
<220> FEATURE:
<221> NAME/KEY: MISC_FEATURE
<222> LOCATION: (112)..(112)
<223> OTHER INFORMATION: X at position 112 is any amino acid
<220> FEATURE:
<221> NAME/KEY: MISC_FEATURE
<222> LOCATION: (115)..(115)
<223> OTHER INFORMATION: X at position 115 is any amino acid
<220> FEATURE:
<221> NAME/KEY: MISC_FEATURE
<222> LOCATION: (118)..(119)
<223> OTHER INFORMATION: X at position 118 to 119 is any amino acid
<220> FEATURE:
<221> NAME/KEY: MISC_FEATURE
<222> LOCATION: (123)..(123)
<223> OTHER INFORMATION: X at position 123 is any amino acid
<220> FEATURE:
<221> NAME/KEY: MISC_FEATURE
<222> LOCATION: (151)..(151)
<223> OTHER INFORMATION: X at position 151 is any amino acid
<220> FEATURE:
<221> NAME/KEY: MISC_FEATURE
<222> LOCATION: (155)..(159)
<223> OTHER INFORMATION: X at position 155 to 159 is any amino acid

<400> SEQUENCE: 31

Glu Val Gln Leu Gln Glu Ser Gly Xaa Xaa Xaa Val Xaa Pro Gly Xaa
1               5                   10                  15

Ser Xaa Lys Xaa Ser Cys Xaa Ala Ser Gly Xaa Thr Phe Xaa Xaa Xaa
            20                  25                  30
```

```
Xaa Met Xaa Trp Val Xaa Gln Xaa Xaa Xaa Lys Xaa Leu Glu Trp Xaa
        35                  40                  45

Xaa Xaa Ile Xaa Xaa Xaa Xaa Xaa Xaa Xaa Xaa Xaa Tyr Xaa Xaa
    50                  55                  60

Xaa Xaa Lys Gly Xaa Xaa Thr Xaa Xaa Xaa Asp Xaa Xaa Xaa Xaa Xaa
65              70                  75                  80

Xaa Xaa Xaa Xaa Xaa Xaa Xaa Leu Xaa Xaa Glu Asp Xaa Xaa Xaa Tyr
                85                  90                  95

Tyr Cys Xaa Xaa Xaa Xaa Tyr Xaa Xaa Xaa Xaa Xaa Xaa Xaa Asp Xaa
            100                 105                 110

Trp Gly Xaa Gly Thr Xaa Xaa Thr Val Ser Xaa Ala Lys Thr Thr Pro
            115                 120                 125

Pro Ser Val Tyr Pro Leu Ala Pro Gly Ser Ala Ala Gln Thr Asn Ser
130                 135                 140

Met Val Thr Leu Gly Cys Xaa Val Lys Gly Xaa Xaa Xaa Xaa Xaa
145                 150                 155

<210> SEQ ID NO 32
<211> LENGTH: 103
<212> TYPE: PRT
<213> ORGANISM: artificial
<220> FEATURE:
<223> OTHER INFORMATION: Consensus alignment of SEQ ID NOS: 8 and 10
<220> FEATURE:
<221> NAME/KEY: MISC_FEATURE
<222> LOCATION: (4)..(4)
<223> OTHER INFORMATION: X at position 4 is any amino acid or a deletion
<220> FEATURE:
<221> NAME/KEY: MISC_FEATURE
<222> LOCATION: (15)..(15)
<223> OTHER INFORMATION: X at position 15 is any amino acid or a
      deletion
<220> FEATURE:
<221> NAME/KEY: MISC_FEATURE
<222> LOCATION: (18)..(18)
<223> OTHER INFORMATION: X at position 18 is any amino acid or a
      deletion
<220> FEATURE:
<221> NAME/KEY: MISC_FEATURE
<222> LOCATION: (24)..(24)
<223> OTHER INFORMATION: X at position 24 is any amino acid or a
      deletion
<220> FEATURE:
<221> NAME/KEY: MISC_FEATURE
<222> LOCATION: (31)..(32)
<223> OTHER INFORMATION: X at position 31 to 32 is any amino acid or a
      deletion
<220> FEATURE:
<221> NAME/KEY: MISC_FEATURE
<222> LOCATION: (34)..(35)
<223> OTHER INFORMATION: X at position 34 to 35 is any amino acid or a
      deletion
<220> FEATURE:
<221> NAME/KEY: MISC_FEATURE
<222> LOCATION: (46)..(48)
<223> OTHER INFORMATION: X at position 46 to 48 is any amino acid or a
      deletion
<220> FEATURE:
<221> NAME/KEY: MISC_FEATURE
<222> LOCATION: (51)..(51)
<223> OTHER INFORMATION: X at position 51 is any amino acid or a
      deletion
<220> FEATURE:
<221> NAME/KEY: MISC_FEATURE
<222> LOCATION: (61)..(61)
<223> OTHER INFORMATION: X at position 61 is any amino acid or a
      deletion
<220> FEATURE:
<221> NAME/KEY: MISC_FEATURE
<222> LOCATION: (78)..(78)
```

```
<223> OTHER INFORMATION: X at position 78 is any amino acid or a
      deletion
<220> FEATURE:
<221> NAME/KEY: MISC_FEATURE
<222> LOCATION: (90)..(90)
<223> OTHER INFORMATION: X at position 90 is any amino acid or a
      deletion
<220> FEATURE:
<221> NAME/KEY: MISC_FEATURE
<222> LOCATION: (92)..(95)
<223> OTHER INFORMATION: X at position 92 to 95 is any amino acid or a
      deletion
<220> FEATURE:
<221> NAME/KEY: MISC_FEATURE
<222> LOCATION: (97)..(97)
<223> OTHER INFORMATION: X at position 97 is any amino acid or a
      deletion
<220> FEATURE:
<221> NAME/KEY: MISC_FEATURE
<222> LOCATION: (101)..(103)
<223> OTHER INFORMATION: X at position 101 to 103 is any amino acid or a
      deletion

<400> SEQUENCE: 32

Asp Ile Val Xaa Thr Gln Ser Pro Ala Ile Met Ser Ala Ser Xaa Gly
1               5                   10                  15

Glu Xaa Val Thr Met Thr Cys Xaa Ala Ser Ser Ser Val Ser Xaa Xaa
            20                  25                  30

Tyr Xaa Xaa Trp Tyr Gln Gln Lys Pro Gly Ser Ser Pro Xaa Xaa Xaa
        35                  40                  45

Ile Tyr Xaa Thr Ser Asn Leu Ala Ser Gly Val Pro Xaa Arg Phe Ser
    50                  55                  60

Gly Ser Gly Ser Gly Thr Ser Tyr Ser Leu Thr Ile Ser Xaa Met Glu
65                  70                  75                  80

Ala Glu Asp Ala Ala Thr Tyr Tyr Cys Xaa Gln Xaa Xaa Xaa Xaa Pro
                85                  90                  95

Xaa Thr Phe Gly Xaa Xaa Xaa
            100

<210> SEQ ID NO 33
<211> LENGTH: 109
<212> TYPE: PRT
<213> ORGANISM: artificial
<220> FEATURE:
<223> OTHER INFORMATION: Consensus alignment of SEQ ID NOS: 8-11
<220> FEATURE:
<221> NAME/KEY: MISC_FEATURE
<222> LOCATION: (3)..(4)
<223> OTHER INFORMATION: X at position 3 to 4 is any amino acid or a
      deletion
<220> FEATURE:
<221> NAME/KEY: MISC_FEATURE
<222> LOCATION: (7)..(11)
<223> OTHER INFORMATION: X at position 7 to 11 is any amino acid or a
      deletion
<220> FEATURE:
<221> NAME/KEY: MISC_FEATURE
<222> LOCATION: (13)..(13)
<223> OTHER INFORMATION: X at position 13 is any amino acid or a
      deletion
<220> FEATURE:
<221> NAME/KEY: MISC_FEATURE
<222> LOCATION: (15)..(15)
<223> OTHER INFORMATION: X at position 15 is any amino acid or a
      deletion
<220> FEATURE:
<221> NAME/KEY: MISC_FEATURE
<222> LOCATION: (17)..(18)
<223> OTHER INFORMATION: X at position 17 to 18 is any amino acid or a
      deletion
<220> FEATURE:
```

```
<221> NAME/KEY: MISC_FEATURE
<222> LOCATION: (20)..(22)
<223> OTHER INFORMATION: X at position 20 to 22 is any amino acid or a
      deletion
<220> FEATURE:
<221> NAME/KEY: MISC_FEATURE
<222> LOCATION: (24)..(24)
<223> OTHER INFORMATION: X at position 24 is any amino acid or a
      deletion
<220> FEATURE:
<221> NAME/KEY: MISC_FEATURE
<222> LOCATION: (27)..(29)
<223> OTHER INFORMATION: X at position 27 to 29 is any amino acid or a
      deletion
<220> FEATURE:
<221> NAME/KEY: MISC_FEATURE
<222> LOCATION: (31)..(35)
<223> OTHER INFORMATION: X at position 31 to 35 is any amino acid or a
      deletion
<220> FEATURE:
<221> NAME/KEY: MISC_FEATURE
<222> LOCATION: (42)..(48)
<223> OTHER INFORMATION: X at position 42 to 48 is any amino acid or a
      deletion
<220> FEATURE:
<221> NAME/KEY: MISC_FEATURE
<222> LOCATION: (51)..(51)
<223> OTHER INFORMATION: X at position 51 is any amino acid or a
      deletion
<220> FEATURE:
<221> NAME/KEY: MISC_FEATURE
<222> LOCATION: (54)..(57)
<223> OTHER INFORMATION: X at position 54 to 57 is any amino acid or a
      deletion
<220> FEATURE:
<221> NAME/KEY: MISC_FEATURE
<222> LOCATION: (62)..(62)
<223> OTHER INFORMATION: X at position 62 is any amino acid or a
      deletion
<220> FEATURE:
<221> NAME/KEY: MISC_FEATURE
<222> LOCATION: (65)..(65)
<223> OTHER INFORMATION: X at position 65 is any amino acid or a
      deletion
<220> FEATURE:
<221> NAME/KEY: MISC_FEATURE
<222> LOCATION: (67)..(67)
<223> OTHER INFORMATION: X at position 67 is any amino acid or a
      deletion
<220> FEATURE:
<221> NAME/KEY: MISC_FEATURE
<222> LOCATION: (72)..(74)
<223> OTHER INFORMATION: X at position 72 to 74 is any amino acid or a
      deletion
<220> FEATURE:
<221> NAME/KEY: MISC_FEATURE
<222> LOCATION: (76)..(76)
<223> OTHER INFORMATION: X at position 76 is any amino acid or a
      deletion
<220> FEATURE:
<221> NAME/KEY: MISC_FEATURE
<222> LOCATION: (79)..(83)
<223> OTHER INFORMATION: X at position 79 to 83 is any amino acid or a
      deletion
<220> FEATURE:
<221> NAME/KEY: MISC_FEATURE
<222> LOCATION: (85)..(85)
<223> OTHER INFORMATION: X at position 85 is any amino acid or a
      deletion
<220> FEATURE:
<221> NAME/KEY: MISC_FEATURE
<222> LOCATION: (87)..(87)
<223> OTHER INFORMATION: X at position 87 is any amino acid or a
      deletion
<220> FEATURE:
<221> NAME/KEY: MISC_FEATURE
<222> LOCATION: (91)..(91)
<223> OTHER INFORMATION: X at position 91 is any amino acid or a
      deletion
```

```
<220> FEATURE:
<221> NAME/KEY: MISC_FEATURE
<222> LOCATION: (93)..(96)
<223> OTHER INFORMATION: X at position 93 to 96 is any amino acid or a
      deletion
<220> FEATURE:
<221> NAME/KEY: MISC_FEATURE
<222> LOCATION: (98)..(98)
<223> OTHER INFORMATION: X at position 98 is any amino acid or a
      deletion
<220> FEATURE:
<221> NAME/KEY: MISC_FEATURE
<222> LOCATION: (105)..(109)
<223> OTHER INFORMATION: X at position 105 to 109 is any amino acid or a
      deletion

<400> SEQUENCE: 33

Asp Ile Xaa Xaa Thr Gln Xaa Xaa Xaa Xaa Ser Xaa Ser Xaa Ser
1               5                   10                  15

Xaa Xaa Ser Xaa Xaa Xaa Ser Xaa Ser Ser Xaa Xaa Xaa Ser Xaa Xaa
            20                  25                  30

Xaa Xaa Xaa Trp Tyr Gln Gln Lys Pro Xaa Xaa Xaa Xaa Xaa Xaa
        35                  40                  45

Ile Tyr Xaa Thr Ser Xaa Xaa Xaa Xaa Gly Val Pro Pro Xaa Arg Phe
50                  55                  60

Xaa Gly Xaa Gly Ser Gly Thr Xaa Xaa Xaa Leu Xaa Ile Ser Xaa Xaa
65                  70                  75                  80

Xaa Xaa Xaa Asp Xaa Ala Xaa Tyr Tyr Cys Xaa Gln Xaa Xaa Xaa Xaa
                85                  90                  95

Pro Xaa Thr Phe Gly Gly Gly Thr Xaa Xaa Xaa Xaa Xaa
            100                 105

<210> SEQ ID NO 34
<211> LENGTH: 122
<212> TYPE: PRT
<213> ORGANISM: artificial
<220> FEATURE:
<223> OTHER INFORMATION: Consensus alignment of SEQ ID NOS: 5 and 19
<220> FEATURE:
<221> NAME/KEY: MISC_FEATURE
<222> LOCATION: (2)..(2)
<223> OTHER INFORMATION: X at position 2 is any amino acid or a deletion
<220> FEATURE:
<221> NAME/KEY: MISC_FEATURE
<222> LOCATION: (9)..(9)
<223> OTHER INFORMATION: X at position 9 is any amino acid or a deletion
<220> FEATURE:
<221> NAME/KEY: MISC_FEATURE
<222> LOCATION: (11)..(11)
<223> OTHER INFORMATION: X at position 11 is any amino acid or a
      deletion
<220> FEATURE:
<221> NAME/KEY: MISC_FEATURE
<222> LOCATION: (13)..(13)
<223> OTHER INFORMATION: X at position 13 is any amino acid or a
      deletion
<220> FEATURE:
<221> NAME/KEY: MISC_FEATURE
<222> LOCATION: (16)..(17)
<223> OTHER INFORMATION: X at position 16 to 17 is any amino acid or a
      deletion
<220> FEATURE:
<221> NAME/KEY: MISC_FEATURE
<222> LOCATION: (20)..(20)
<223> OTHER INFORMATION: X at position 20 is any amino acid or a
      deletion
<220> FEATURE:
<221> NAME/KEY: MISC_FEATURE
<222> LOCATION: (28)..(28)
<223> OTHER INFORMATION: X at position 28 is any amino acid or a
      deletion
```

```
<220> FEATURE:
<221> NAME/KEY: MISC_FEATURE
<222> LOCATION: (35)..(35)
<223> OTHER INFORMATION: X at position 35 is any amino acid or a
      deletion
<220> FEATURE:
<221> NAME/KEY: MISC_FEATURE
<222> LOCATION: (38)..(38)
<223> OTHER INFORMATION: X at position 38 is any amino acid or a
      deletion
<220> FEATURE:
<221> NAME/KEY: MISC_FEATURE
<222> LOCATION: (43)..(43)
<223> OTHER INFORMATION: X at position 43 is any amino acid or a
      deletion
<220> FEATURE:
<221> NAME/KEY: MISC_FEATURE
<222> LOCATION: (46)..(46)
<223> OTHER INFORMATION: X at position 46 is any amino acid or a
      deletion
<220> FEATURE:
<221> NAME/KEY: MISC_FEATURE
<222> LOCATION: (51)..(51)
<223> OTHER INFORMATION: X at position 51 is any amino acid or a
      deletion
<220> FEATURE:
<221> NAME/KEY: MISC_FEATURE
<222> LOCATION: (55)..(55)
<223> OTHER INFORMATION: X at position 55 is any amino acid or a
      deletion
<220> FEATURE:
<221> NAME/KEY: MISC_FEATURE
<222> LOCATION: (57)..(57)
<223> OTHER INFORMATION: X at position 7 is any amino acid or a deletion
<220> FEATURE:
<221> NAME/KEY: MISC_FEATURE
<222> LOCATION: (62)..(63)
<223> OTHER INFORMATION: X at position 62 to 63 is any amino acid or a
      deletion
<220> FEATURE:
<221> NAME/KEY: MISC_FEATURE
<222> LOCATION: (65)..(65)
<223> OTHER INFORMATION: X at position 65 is any amino acid or a
      deletion
<220> FEATURE:
<221> NAME/KEY: MISC_FEATURE
<222> LOCATION: (72)..(73)
<223> OTHER INFORMATION: X at position 72 to 73 is any amino acid or a
      deletion
<220> FEATURE:
<221> NAME/KEY: MISC_FEATURE
<222> LOCATION: (84)..(85)
<223> OTHER INFORMATION: X at position 84 to 85 is any amino acid or a
      deletion
<220> FEATURE:
<221> NAME/KEY: MISC_FEATURE
<222> LOCATION: (88)..(88)
<223> OTHER INFORMATION: X at position 88 is any amino acid or a
      deletion
<220> FEATURE:
<221> NAME/KEY: MISC_FEATURE
<222> LOCATION: (91)..(91)
<223> OTHER INFORMATION: X at position 91 is any amino acid or a
      deletion
<220> FEATURE:
<221> NAME/KEY: MISC_FEATURE
<222> LOCATION: (93)..(93)
<223> OTHER INFORMATION: X at position 93 is any amino acid or a
      deletion
<220> FEATURE:
<221> NAME/KEY: MISC_FEATURE
<222> LOCATION: (95)..(95)
<223> OTHER INFORMATION: X at position 95 is any amino acid or a
      deletion
<220> FEATURE:
<221> NAME/KEY: MISC_FEATURE
<222> LOCATION: (99)..(110)
<223> OTHER INFORMATION: X at position 99 to 110 is any amino acid or a
      deletion
```

-continued

<400> SEQUENCE: 34

Gln Xaa Gln Leu Val Gln Ser Gly Xaa Glu Xaa Lys Xaa Pro Gly Xaa
1               5                   10                  15

Xaa Val Lys Xaa Ser Cys Lys Ala Ser Gly Tyr Xaa Phe Thr Thr Tyr
            20                  25                  30

Gly Met Xaa Trp Val Xaa Gln Ala Pro Gly Xaa Gly Leu Xaa Trp Met
        35                  40                  45

Gly Trp Xaa Asn Thr Tyr Xaa Gly Xaa Pro Thr Tyr Ala Xaa Xaa Phe
    50                  55                  60

Xaa Gly Arg Phe Val Phe Ser Xaa Xaa Thr Ser Ala Ser Thr Ala Tyr
65                  70                  75                  80

Leu Gln Ile Xaa Xaa Leu Lys Xaa Glu Asp Xaa Ala Xaa Tyr Xaa Cys
                85                  90                  95

Ala Arg Xaa Xaa Xaa Xaa Xaa Xaa Xaa Xaa Xaa Xaa Xaa Tyr Trp
            100                 105                 110

Gly Gln Gly Thr Leu Val Thr Val Ser Ala
            115                 120

<210> SEQ ID NO 35
<211> LENGTH: 107
<212> TYPE: PRT
<213> ORGANISM: artificial
<220> FEATURE:
<223> OTHER INFORMATION: Consensus alignment of SEQ ID NOS: 12 and 20
<220> FEATURE:
<221> NAME/KEY: MISC_FEATURE
<222> LOCATION: (1)..(1)
<223> OTHER INFORMATION: X at position 1 is any amino acid or a deletion
<220> FEATURE:
<221> NAME/KEY: MISC_FEATURE
<222> LOCATION: (9)..(11)
<223> OTHER INFORMATION: X at position 9 to 11 is any amino acid or a
      deletion
<220> FEATURE:
<221> NAME/KEY: MISC_FEATURE
<222> LOCATION: (16)..(18)
<223> OTHER INFORMATION: X at position 16 to 18 is any amino acid or a
      deletion
<220> FEATURE:
<221> NAME/KEY: MISC_FEATURE
<222> LOCATION: (20)..(22)
<223> OTHER INFORMATION: X at position 20 to 22 is any amino acid or a
      deletion
<220> FEATURE:
<221> NAME/KEY: MISC_FEATURE
<222> LOCATION: (30)..(32)
<223> OTHER INFORMATION: X at position 30 to 32 is any amino acid or a
      deletion
<220> FEATURE:
<221> NAME/KEY: MISC_FEATURE
<222> LOCATION: (39)..(42)
<223> OTHER INFORMATION: X at position 39 to 42 is any amino acid or a
      deletion
<220> FEATURE:
<221> NAME/KEY: MISC_FEATURE
<222> LOCATION: (45)..(45)
<223> OTHER INFORMATION: X at position 45 is any amino acid or a
      deletion
<220> FEATURE:
<221> NAME/KEY: MISC_FEATURE
<222> LOCATION: (49)..(49)
<223> OTHER INFORMATION: X at position 49 is any amino acid or a
      deletion
<220> FEATURE:
<221> NAME/KEY: MISC_FEATURE
<222> LOCATION: (53)..(53)
<223> OTHER INFORMATION: X at position 53 is any amino acid or a
      deletion
<220> FEATURE:

```
<221> NAME/KEY: MISC_FEATURE
<222> LOCATION: (55)..(55)
<223> OTHER INFORMATION: X at position 55 is any amino acid or a
      deletion
<220> FEATURE:
<221> NAME/KEY: MISC_FEATURE
<222> LOCATION: (58)..(58)
<223> OTHER INFORMATION: X at position 58 is any amino acid or a
      deletion
<220> FEATURE:
<221> NAME/KEY: MISC_FEATURE
<222> LOCATION: (65)..(65)
<223> OTHER INFORMATION: X at position 65 is any amino acid or a
      deletion
<220> FEATURE:
<221> NAME/KEY: MISC_FEATURE
<222> LOCATION: (74)..(74)
<223> OTHER INFORMATION: X at position 74 is any amino acid or a
      deletion
<220> FEATURE:
<221> NAME/KEY: MISC_FEATURE
<222> LOCATION: (78)..(78)
<223> OTHER INFORMATION: X at position 78 is any amino acid or a
      deletion
<220> FEATURE:
<221> NAME/KEY: MISC_FEATURE
<222> LOCATION: (80)..(80)
<223> OTHER INFORMATION: X at position 80 is any amino acid or a
      deletion
<220> FEATURE:
<221> NAME/KEY: MISC_FEATURE
<222> LOCATION: (83)..(85)
<223> OTHER INFORMATION: X at position 83 to 85 is any amino acid or a
      deletion
<220> FEATURE:
<221> NAME/KEY: MISC_FEATURE
<222> LOCATION: (87)..(87)
<223> OTHER INFORMATION: X at position 87 is any amino acid or a
      deletion
<220> FEATURE:
<221> NAME/KEY: MISC_FEATURE
<222> LOCATION: (89)..(89)
<223> OTHER INFORMATION: X at position 89 is any amino acid or a
      deletion
<220> FEATURE:
<221> NAME/KEY: MISC_FEATURE
<222> LOCATION: (92)..(92)
<223> OTHER INFORMATION: X at position 92 is any amino acid or a
      deletion
<220> FEATURE:
<221> NAME/KEY: MISC_FEATURE
<222> LOCATION: (94)..(94)
<223> OTHER INFORMATION: X at position 94 is any amino acid or a
      deletion
<220> FEATURE:
<221> NAME/KEY: MISC_FEATURE
<222> LOCATION: (100)..(100)
<223> OTHER INFORMATION: X at position 100 is any amino acid or a
      deletion
<220> FEATURE:
<221> NAME/KEY: MISC_FEATURE
<222> LOCATION: (104)..(104)
<223> OTHER INFORMATION: X at position 104 is any amino acid or a
      deletion
<220> FEATURE:
<221> NAME/KEY: MISC_FEATURE
<222> LOCATION: (106)..(106)
<223> OTHER INFORMATION: X at position 106 is any amino acid or a
      deletion

<400> SEQUENCE: 35

Xaa Ile Val Leu Thr Gln Ser Pro Xaa Xaa Xaa Ser Val Thr Pro Xaa
1               5                   10                  15

Xaa Xaa Val Xaa Xaa Xaa Cys Arg Ala Ser Gln Ser Ile Xaa Xaa Xaa
            20                  25                  30

Leu His Trp Tyr Gln Gln Xaa Xaa Xaa Xaa Ser Pro Xaa Leu Leu Ile
```

```
            35                  40                  45
Xaa Tyr Ala Ser Xaa Ser Xaa Ser Gly Xaa Pro Ser Arg Phe Ser Gly
 50                  55                  60

Xaa Gly Ser Gly Thr Asp Phe Thr Leu Xaa Ile Asn Ser Xaa Glu Xaa
 65                  70                  75                  80

Glu Asp Xaa Xaa Xaa Tyr Xaa Cys Xaa Gln Ser Xaa Ser Xaa Pro Leu
                 85                  90                  95

Thr Phe Gly Xaa Gly Thr Lys Xaa Glu Xaa Lys
                100                 105

<210> SEQ ID NO 36
<211> LENGTH: 480
<212> TYPE: PRT
<213> ORGANISM: Staphylococcus aureus glucosaminidase

<400> SEQUENCE: 36

Ala Tyr Thr Val Thr Lys Pro Gln Thr Thr Gln Thr Val Ser Lys Ile
 1               5                  10                  15

Ala Gln Val Lys Pro Asn Asn Thr Gly Ile Arg Ala Ser Val Tyr Glu
                20                  25                  30

Lys Thr Ala Lys Asn Gly Ala Lys Tyr Ala Asp Arg Thr Phe Tyr Val
             35                  40                  45

Thr Lys Glu Arg Ala His Gly Asn Glu Thr Tyr Val Leu Leu Asn Asn
 50                  55                  60

Thr Ser His Asn Ile Pro Leu Gly Trp Phe Asn Val Lys Asp Leu Asn
 65                  70                  75                  80

Val Gln Asn Leu Gly Lys Glu Val Lys Thr Thr Gln Lys Tyr Thr Val
                 85                  90                  95

Asn Lys Ser Asn Asn Gly Leu Ser Met Val Pro Trp Gly Thr Lys Asn
                100                 105                 110

Gln Val Ile Leu Thr Gly Asn Asn Ile Ala Gln Gly Thr Phe Asn Ala
            115                 120                 125

Thr Lys Gln Val Ser Val Gly Lys Asp Val Tyr Leu Tyr Gly Thr Ile
130                 135                 140

Asn Asn Arg Thr Gly Trp Val Asn Ala Lys Asp Leu Thr Ala Pro Thr
145                 150                 155                 160

Ala Val Lys Pro Thr Thr Ser Ala Ala Lys Asp Tyr Asn Tyr Thr Tyr
                165                 170                 175

Val Ile Lys Asn Gly Asn Gly Tyr Tyr Tyr Val Thr Pro Asn Ser Asp
            180                 185                 190

Thr Ala Lys Tyr Ser Leu Lys Ala Phe Asn Glu Gln Pro Phe Ala Val
        195                 200                 205

Val Lys Glu Gln Val Ile Asn Gly Gln Thr Trp Tyr Tyr Gly Lys Leu
210                 215                 220

Ser Asn Gly Lys Leu Ala Trp Ile Lys Ser Thr Asp Leu Ala Lys Glu
225                 230                 235                 240

Leu Ile Lys Tyr Asn Gln Thr Gly Met Thr Leu Asn Gln Val Ala Gln
                245                 250                 255

Ile Gln Ala Gly Leu Gln Tyr Lys Pro Gln Val Gln Arg Val Pro Gly
            260                 265                 270

Lys Trp Thr Asp Ala Asn Phe Asn Asp Val Lys His Ala Met Asp Thr
        275                 280                 285

Lys Arg Leu Ala Gln Asp Pro Ala Leu Lys Tyr Gln Phe Leu Arg Leu
290                 295                 300
```

```
Asp Gln Pro Gln Asn Ile Ser Ile Asp Lys Ile Asn Gln Phe Leu Lys
305                 310                 315                 320

Gly Lys Gly Val Leu Glu Asn Gln Gly Ala Ala Phe Asn Lys Ala Ala
                325                 330                 335

Gln Met Tyr Gly Ile Asn Glu Val Tyr Leu Ile Ser His Ala Leu Leu
            340                 345                 350

Glu Thr Gly Asn Gly Thr Ser Gln Leu Ala Lys Gly Ala Asp Val Val
        355                 360                 365

Asn Asn Lys Val Val Thr Asn Ser Asn Thr Lys Tyr His Asn Val Phe
    370                 375                 380

Gly Ile Ala Ala Tyr Asp Asn Asp Pro Leu Arg Glu Gly Ile Lys Tyr
385                 390                 395                 400

Ala Lys Gln Ala Gly Trp Asp Thr Val Ser Lys Ala Ile Val Gly Gly
                405                 410                 415

Ala Lys Phe Ile Gly Asn Ser Tyr Val Lys Ala Gly Gln Asn Thr Leu
            420                 425                 430

Tyr Lys Met Arg Trp Asn Pro Ala His Pro Gly Thr His Gln Tyr Ala
        435                 440                 445

Thr Asp Val Asp Trp Ala Asn Ile Asn Ala Lys Ile Ile Lys Gly Tyr
    450                 455                 460

Tyr Asp Lys Ile Gly Glu Val Gly Lys Tyr Phe Asp Ile Pro Gln Tyr
465                 470                 475                 480

<210> SEQ ID NO 37
<211> LENGTH: 6
<212> TYPE: PRT
<213> ORGANISM: Artificial
<220> FEATURE:
<223> OTHER INFORMATION: Glycine rich linker
<220> FEATURE:
<221> NAME/KEY: MISC_FEATURE
<222> LOCATION: (6)..(6)
<223> OTHER INFORMATION: Where X is optional and can be S

<400> SEQUENCE: 37

Gly Gly Gly Ser Ser Xaa
1               5
```

ANTI-GLUCOSAMINIDASE PASSIVE IMMUNIZATION FOR *STAPHYLOCOCCUS AUREUS* INFECTIONS

This application is a continuation of U.S. patent application Ser. No. 15/662,715 filed on Jul. 28, 2017, which is a continuation of U.S. patent application Ser. No. 13/696,019, now U.S. Pat. No. 9,737,601, which is a national stage application under 35 U.S.C. § 371 of PCT Application No. PCT/US2011/035033, filed May 3, 2011, which claims the benefit of U.S. Provisional Patent Application Ser. No. 61/330,568, filed May 3, 2010, which is hereby incorporated by reference in its entirety.

This invention was made with government support under R43 AI085844 awarded by National Institutes of Health. The government has certain rights in the invention.

FIELD OF THE INVENTION

The present invention relates to passive immunization against *Staphylococcus aureus* infection, particularly for the prevention or treatment of osteomyelitis and for implantation of an orthopedic implant or graft. Antibodies that bind specifically to *S. aureus* glucosaminidase and pharmaceutical compositions containing the same can be used for these purposes.

BACKGROUND OF THE INVENTION

There is a great need for novel interventions of chronic osteomyelitis (OM) as approximately 112,000 orthopedic device-related infections occur per year in the US, at an approximate hospital cost of $15,000-70,000 per incident (Darouiche, "Treatment of Infections Associated With Surgical Implants," *N. Engl. J. Med.* 350(14):1422-9 (2004)). Although improvements in surgical technique and aggressive antibiotic prophylaxis have decreased the infection rate following orthopedic implant surgery to 1-5%, osteomyelitis (OM) remains a serious problem and appears to be on the rise from minimally invasive surgery (Mahomed et al., "Rates and Outcomes of Primary and Revision Total Hip Replacement in the United States Medicare Population,"*J. Bone Joint Surg. Am.* 85(A-1):27-32 (2003); WHO Global Strategy for Containment of Antimicrobial Resistance, 2001). The significance of this resurgence, 80% of which is due to *Staphylococcus aureus*, is amplified by the fact that ~50% of clinical isolates are methicillin resistant *S. aureus* (MRSA). While the infection rates for joint prosthesis and fracture-fixation devices have been only 0.3-11% and 5-15% of cases, respectively, over the last decade (Lew and Waldvogel, "Osteomyelitis," *Lancet* 364(9431):369-79 (2004); Toms et al., "The Management of Pen-Prosthetic Infection in Total Joint Arthroplasty," *J. Bone Joint Surg. Br.* 88(2): 149-55 (2006)), this result may lead to amputation or death. Additionally, the popularization of "minimally invasive surgery" for elective total joint replacements (TJR) in which the very small incision often leads to complications from the prosthesis contacting skin during implantation, has markedly increased the incidence of OM (Mahomed et al., "Rates and Outcomes of Primary and Revision Total Hip Replacement in the United States Medicare Population," *J. Bone Joint Surg. Am.* 85(A-1):27-32 (2003); WHO Global Strategy for Containment of Antimicrobial Resistance, 2001). These infections require a very expensive two-stage revision surgery, and recent reports suggest that success rates could be as low as 50% (Azzam et al., "Outcome of a Second Two-stage Reimplantation for Periprosthetic Knee Infection," *Clin. Orthop. Relat. Res.* 467(7):1706-14 (2009)). However, the greatest concern is the emergence of drug resistant strains, most notably MRSA, which has surpassed HIV as the most deadly pathogen in North America, and continues to make the management of chronic OM more difficult, placing a great demand for novel therapeutic interventions. There is a great need for alternative interventional strategies, particularly for immune compromised elderly who are the primary recipients of TJR.

Presently, there are no prophylactic treatments that can protect high-risk patients from MRSA, most notably the aging "baby boomers" who account for most of the 1.5 million TJR performed annually in the United States. A vaccine that would decrease the MRSA incidence by 50-80% would not only reduce the number one complication of joint replacement and open fracture repair procedures, but also cut the healthcare burden by a similar amount.

Studies have documented that 80% of chronic OM is caused by *S. aureus*. These bacteria contain several factors that make them bone pathogens including several cell-surface adhesion molecules that facilitate their binding to bone matrix (Flock et al., "Cloning and Expression of the Gene for a Fibronectin-Binding Protein From *Staphylococcus aureus*," *Embo. J.* 6(8):2351-7 (1987)), toxins capable of stimulating bone resorption (Nair et al., "Surface-Associated Proteins From *Staphylococcus aureus* Demonstrate Potent Bone Resorbing Activity," *J. Bone Miner. Res.* 10(5): 726-34 (1995)), through increased osteoclast activity (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). The rate-limiting step in the evolution and persistence of infection is the formation of biofilm around implanted devices (Costerton et al., "Bacterial Biofilms: A Common Cause of Persistent Infections," *Science* 284(5418):1318-22 (1999)). Shortly after implantation, a conditioning layer composed of host-derived adhesins (including fibrinogen, fibronectin, and collagen) forms on the surface of the implant and invites the adherence of free-floating bacteria derived from hematogenous seeding, including spread of infection from a contiguous area (the skin adjacent to a wound), surgical inoculation of bacteria into bone, or trauma coincident with significant disruption of the associated soft tissue bone envelope (Darouiche, "Treatment of Infections Associated With Surgical Implants," *N. Engl. J. Med.* 350(14):1422-9 (2004)). Over the next few days bacterial cell division, recruitment of additional planktonic organisms, and secretion of bacterial products (such as the glycocalyx) produces the biofilm. This biofilm serves as a dominant barrier to protect the bacteria from the action of antibiotics, phagocytic cells, antibodies and impairs lymphocyte functions (Gray et al., "Effect of Extracellular Slime Substance From *Staphylococcus epidermidis* on the Human Cellular Immune Response," *Lancet* 1(8373):365-7 (1984); Johnson et al., "Interference With Granulocyte Function By *Staphylococcus epidermidis* Slime," *Infect. Immun.* 54(1):13-20 (1986); Naylor et al., "Antibiotic Resistance of Biomaterial-Adherent Coagulase-Negative and Coagulase-Positive Staphylococci," *Clin. Orthop. Relat. Res.* 261:126-33 (1990)).

Another recent discovery is that *S. aureus* not only colonizes bone matrix, but is also internalized by osteoblasts in vitro (Ellington et al., "Involvement of Mitogen-Activated Protein Kinase Pathways in *Staphylococcus aureus* Invasion of Normal Osteoblasts," *Infect. Immun.* 69(9):5235-42 (2001)) and in vivo (Reilly et al., "In Vivo Internalization of *Staphylococcus aureus* by Embryonic Chick Osteoblasts,"

Bone 26(1):63-70 (2000)). This provides yet another layer of antibody and antibiotic resistance. This phase of infection occurs under conditions of markedly reduced metabolic activity and sometimes appears as so-called small-colony variants that likely accounts for its persistence (Proctor et al., "Persistent and Relapsing Infections Associated with Small-Colony Variants of *Staphylococcus aureus*," *Clin. Infect. Dis.* 20(1):95-102 (1995)). At this point the bacteria may also express phenotypic resistance to antimicrobial treatment, also explaining the high failure rate of short courses of therapy (Chuard et al., "Resistance of *Staphylococcus aureus* Recovered From Infected Foreign Body in Vivo to Killing by Antimicrobials," *J. Infect. Dis.* 163(6): 1369-73 (1991)). Due to these extensive pathogenic mechanism, OM is notorious for its tendency to recur even after years of quiescence, and it is accepted that a complete cure is an unlikely outcome (Mader and Calhoun, "Long-Bone Osteomyelitis Diagnosis and Management," *Hosp. Pract. (Off Ed)* 29(10):71-6, 9, 83 passim (1994)).

One of the key questions in the field of chronic OM is why current knowledge of factors that regulate chronic OM so limited. Supposedly, the experimental tools necessary to elucidate bacterial virulence gene have been available for over a century. There are three explanations for this anomaly. First, although the total number of osteomyelitis cases is high, its incidence of 1-5% is too low for rigorous prospective clinical studies, with the possible exception of revision arthropasty. Second, it is well known that in vitro cultures rapidly select for growth of organisms that do not elaborate an extracellular capsule, such that biofilm biology can only be studied with in vivo models (Costerton et al., "Bacterial Biofilms: A Common Cause of Persistent Infections," *Science* 284(5418):1318-22 (1999)). This leads to the "greatest obstacle" in this field, which is the absence of a quantitative animal model that can assess the initial planktonic growth phase of the bacteria prior to biofilm formation. To date, much of the knowledge of its pathogenesis comes from animal models (Norden, "Lessons Learned From Animal Models of Osteomyelitis," *Rev. Infect. Dis.* 10(1):103-10 (1988)), which have been developed for the chicken (Daum et al., "A Model of *Staphylococcus aureus* Bacteremia, Septic Arthritis, and Osteomyelitis in Chickens," *J. Orthop. Res.* 8(6):804-13 (1990)), rat (Rissing et al., "Model of Experimental Chronic Osteomyelitis in Rats," *Infect. Immun.* 47(3):581-6 (1985)), guinea pig (Passl et al., "A Model of Experimental Post-Traumatic Osteomyelitis in Guinea Pigs," *J. Trauma* 24(4):323-6 (1984)), rabbit (Worlock et al., "An Experimental Model of Post-Traumatic Osteomyelitis in Rabbits," *Br. J. Exp. Pathol.* 69(2):235-44 (1988)), dog (Varshney et al., "Experimental Model of Staphylococcal Osteomyelitis in Dogs," *Indian J. Exp. Biol.* 27(9):816-9 (1989)), sheep (Kaarsemaker et al., "New Model for Chronic Osteomyelitis With *Staphylococcus aureus* in Sheep," *Clin. Orthop. Relat. Res.* 339:246-52 (1997)) and most recently mouse (Marriott et al., "Osteoblasts Express the Inflammatory Cytokine Interleukin-6 in a Murine Model of *Staphylococcus aureus* Osteomyelitis and Infected Human Bone Tissue," *Am. J. Pathol.* 164(4):1399-406 (2004)). While these models have been used to confirm the importance of bacterial adhesions identified from in vitro assays (Chuard et al., "Susceptibility of *Staphylococcus aureus* Growing on Fibronectin-Coated Surfaces to Bactericidal Antibiotics,"*Antimicrob. Agents Chemother.* 37(4): 625-32 (1993); Buxton et al., "Binding of a *Staphylococcus aureus* Bone Pathogen to Type I Collagen,"*Microb. Pathog.* 8(6):441-8 (1990); Switalski et al., "A Collagen Receptor on *Staphylococcus aureus* Strains Isolated From Patients With Septic Arthritis Mediates Adhesion to Cartilage,"*Mol. Microbiol.* 7(1):99-107 (1993)), they do not have an outcome measure of in vivo growth, bacterial load, or osteolysis. Thus, they cannot be efficiently used to assess drug effects, bacterial mutants, and the role of host factors with transgenic mice.

Based on over 150 years of research, a clear paradigm to explain microbial pathogenesis has emerged. This model also applies to OM. The initial step of infection occurs when a unicellular bacterium invades the body. At this point the microbe must respond to environmental changes and express virulence genes that will help it defeat innate immunity and provide it with adhesin receptors to attach to the host. The bacterium is also dependent on the stochastic availability of host adhesins from necrotic tissue or a foreign body such as an implant. Successful completion of these steps leads to an exponential growth phase, which ceases at the point of nutrient exhaustion and/or the development of adaptive immunity. Following the exponential growth phase the bacteria are forced to persist under dormant growth conditions within the biofilm. However, at this point the infection is now chronic and cannot be eradicated by drugs or host immunity. Thus, the focus in this field has been on cell surface adhesins that specifically interact with extracellular matrix components known as MSCRAMMs (microbial surface components recognizing adhesive matrix molecules) (Patti et al., "MSCRAMM-Mediated Adherence of Microorganisms to Host Tissues,"*Annu. Rev. Microbiol.* 48:585-617 (1994)). In fact, essentially all anti-*S. aureus* vaccines that have been developed to date have been directed against MSCRAMMs that are important for host tissue colonization and invasion. The goal of these vaccines is to generate antibodies that bind to these surface antigens, thereby inhibiting their attachment to host tissue. By opsinizing the bacterial surface, these antibodies can also mediate *S. aureus* clearance by phagocytic cells. Unfortunately, *S. aureus* has many adhesins, such that inhibition of one or more may not be sufficient to prevent bacterial attachment. Furthermore, bacterial clearance by phagocytic cells may be limited in avascular tissue, such that mAb may need additional antimicrobial mechanism of action to significantly reduce the in vivo planktonic growth of *S. aureus* and prevent the establishment of chronic OM or reinfection during revision total joint replacement surgery.

The present invention is directed to overcoming these and other deficiencies in the art.

SUMMARY OF THE INVENTION

A first aspect of the present invention is directed to a monoclonal antibody or binding portion thereof that binds specifically to a *Staphylococcus aureus* glucosaminidase and inhibits in vivo growth of *S. aureus*. In one embodiment, the monoclonal antibody or binding portion thereof binds specifically to an epitope lying wholly or partly within an R3 domain of the *S. aureus* glucosaminidase.

A second aspect of present invention relates to a cell line that expresses a monoclonal antibody or binding portion of the present invention. In one embodiment, the cell line is a hybridoma cell line. In another embodiment, the cell line is a recombinant cell line that expresses the antibody.

A third aspect of the present invention relates to a pharmaceutical composition that may include a carrier and one or more monoclonal antibodies or binding portions of the present invention.

A fourth aspect of the present invention relates to a method of treating *S. aureus* infection that may include administering to a patient having a *S. aureus* infection an effective amount of a monoclonal antibody, binding portion, or pharmaceutical composition of the present invention.

A fifth aspect of the present invention relates to a method of treating osteomyelitis that may include administering to a patient having a *S. aureus* bone or joint infection an effective amount of a monoclonal antibody, binding portion, or pharmaceutical composition of the present invention.

A sixth aspect of the present invention relates to a method of introducing an orthopedic implant into a patient that may include administering to a patient in need of an orthopedic implant an effective amount of a monoclonal antibody, binding portion, or pharmaceutical composition of the present invention, and introducing the orthopedic implant into the patient. In this aspect of the present invention, the monoclonal antibody, binding portion, or pharmaceutical composition acts as a prophylactic agent. In certain embodiments, this aspect of the invention is directed to preventing OM or *S. aureus* reinfection during or subsequent to revision total joint replacement surgery.

Because *S. aureus*, and especially antibiotic resistant variants such as methicillin resistant *S. aureus* (MRSA), are the most common and challenging causes of *Staphylococcus* infections, the methods of the present invention aim to disrupt critical steps in the growth cycle of these microorganisms. The present invention also relates to a passive immunization for preventing infections in patients, for example, patients undergoing total joint replacement. The selected target for immunization is the glucosaminidase (Gmd) that *S. aureus* secretes to facilitate cytokinesis, the separation of cells during mitosis (Oshida et al., "A *Staphylococcus aureus* Autolysin that has an N-acetylmuramoyl-L-Alanine Amidase Domain and an Endo-beta-N-acetylglucosaminidase Domain: Cloning, Sequence Analysis, and Characterization," *Proc Natl Acad Sci USA* 92:285-9 (1995); Oshida et al., "Expression Analysis of the Autolysin Gene (ad) of *Staphylococcus aureus*," *Microbiol Immunol* 42:655-9 (1998); Sugai et al., "Localized Perforation of the Cell Wall by a Major Autolysin: atl Gene Products and the Onset of Penicillin-induced Lysis of *Staphylococcus aureus*," *J Bacteriol* 179:2958-62 (1997); and Yamada et al., "An Autolysin Ring Associated with Cell Separation of *Staphylococcus aureus*," *J Bacteriol* 178:1565-71 (1996), which are hereby incorporated by reference in their entirety).

To study and evaluate *S. aureus* infections, OM and various therapies directed towards *Staphylococcus* infections, a novel murine model of implant-associated OM in which a stainless steel pin is coated with *S. aureus* and implanted transcortically through the tibial metaphysic was used (Li et al., "Quantitative Mouse Model of Implant-Associated Osteomyelitis and the Kinetics of Microbial Growth, Osteolysis, and Humoral Immunity," *J Orthop. Res.* 26(1):96-105 (2008), which is hereby incorporated by reference in its entirety). This model provides highly reproducible OM with Gram-positive biofilm, osteolysis, sequestrum/involucrum formation, and closely resembles clinical OM. Furthermore, in vivo bioluminescence imaging was used to quantify the planktonic growth phase of the bacteria; real time quantitative-PCR (RTQ-PCR) was used to determine nuc gene copy number in infected bone tissue to quantify the total bacteria load; and micro-CT was used to quantify osteolysis.

Using the above-mentioned murine model of osteomyelitis, antibodies specific for Gmd have been identified as a conspicuous part of the successful immune response in the challenged mice. In addition, a vaccine comprising recombinant Gmd with N-terminal $His_6$ (Gmd-His) elicited at least partial immunity in the mouse model. The anti-Gmd antibodies can block *S. aureus* cell division by either directly blocking cell division or by recruiting host effectors such as phagocytes or complement at a vulnerable point in the cycle of cell division.

Experiments demonstrating the action of individual monoclonal antibodies on the cell growth of *S. aureus* are presented in detail in the accompanying examples. The specific objective was to determine if single antibodies, in the absence of any immune effectors, would suppress or alter the growth of rapidly dividing *S. aureus*. The growth-related increase in light-scattering by growing cultures of *S. aureus* Xen29 was reduced by five selected monoclonal antibodies, but they did not appear to actually alter the in vitro growth rate per se. Rather, they appear to have reduced the activity of Gmd to a degree such that dividing cells failed to separate from each other. The effect was dose-dependent and consistent with a high affinity interaction between each antibody and Gmd. These effects demonstrate that these antibodies, raised against recombinant Gmd, react effectively with native Gmd and diminish its enzymatic activity. One of the monoclonal antibodies, 1C11, demonstrated the unique ability to promote cell-independent lysis of *S. aureus*, and two monoclonal antibodies, 1C11 and 3A8, demonstrated an ability to inhibit in vivo *S. aureus* growth and infection during orthopedic implant surgery in an in vivo mouse model.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

FIGS. 2A-H show the histology of trans-tibial implant-associated OM. H&E (Haematoxylin and Eosin stain) (FIGS. 2A-C), TRAP (Tartrate-Resistant Acid Phosphatase) (FIGS. 2D-F) and Gram stained (FIGS. 2G and 2H) sections of histology at the pin site (*) adjacent to the tibial cortex (#), 9 days after implantation of a sterile pin (FIGS. 2A, 2D, and 2G), or a pin coated with *S. aureus* (FIGS. 2B, 2C, 2E, 2F, and 2H). Of note is the new bone (h) that forms around the sterile pin (FIGS. 2A, 2D, and 2G) vs. the necrotic sequestrum (s) and involucrum (i) adjacent to the infected pin. While very few TRAP+ osteoclasts (yellow arrow heads) were present in the uninfected samples (FIG. 2D), numerous osteoclasts appear to be actively resorbing the cortex adjacent to the infected pin, and remodeling the new woven bone that is encasing the involucrum (FIGS. 2E and 2F). Gram staining confirmed the absence of bacteria in the specimens with the sterile pin (FIG. 2G) and their presence (black arrow heads) within the necrotic bone around the infected pins.

FIGS. 4A-C show that glucosaminidase of *S. aureus* autolysin is the 56 kDa immuno-dominant antigen. To elucidate the molecular identity of the novel *S. aureus* antigens identified in FIG. 3, subtractive immunoblot analysis of 2D-SDS-PAGE of whole cell extract was performed with pre-immune and day 14 immune sera. Three 2D gels were run after isoelectric focusing (pH 4.0-10.0). The first was Coomassie blue-stained (FIG. 4A). The others were Western blotted with either day 0 (FIG. 4B) or day 14 sera (FIG. 4C). In addition to the background reactivity, the immune serum detected a specific polypeptide (~53 kDa; pH 9: arrow). The 53 kDa spot was removed from the Coomassie gel, digested with trypsin, and analyzed by MALDI, which resolved 70 individual peptide peaks. The amino acid sequence from every peptide was a 100% match with the known sequence of the glucosaminidase of *S. aureus* autolysin, which is 53.6 kDa and has a pI of 9.66.

FIG. 5A shows BLI levels (p/sec/cm$^2$/sr) at the site of infection and was assessed longitudinally in mice that received a sterile trans-tibial pin (Uninfected), or a pin coated with Xen 29 *S. aureus* (Infected) and were imaged on the indicated day. The circle in the top left image highlights the 1.5 cm diameter region of interest (ROI) that was assessed for BLI in each mouse at each time point. FIG. 5B shows the data from mice (N=5) that were Uninfected, Infected or infected and treated with parenteral antibiotics (Gentamycin) and were assessed for BLI longitudinally at the indicated time following surgery. The data are presented as the mean+/−SD (*Significantly greater vs. Day 0; p<0.05).

FIG. 6A shows serum ELISA in which His-Gmd was used as the antigen to assay anti-Gmd antibody titers in mouse serum which was generated using a known high titer anti-sera from *S. aureus* infected mice. The serial dilution factor (X axis) and absorbance reading at 450 nm (Y axis) of the serial 2-fold diluted sera samples are plotted in the XY plane using GraphPad Prism 4 software. The functional titer (1:3623) is extrapolated from the inflection point (arrow) of the dilution curve. FIG. 6B shows the ELISA used to determine the titers of anti-Gmd antibodies in the sera of mice pre-immunization, pre-boost and pre-challenge with the indicated vaccine. Note that only mice immunized with the His-Gmd vaccine obtained high titers.

FIG. 10 shows the effect of Control mAb MOPC21 on in vitro *S. aureus* growth. 100 cfu of Xen29 from a culture in log-phase growth were incubated at 37° C. with a range of concentrations of isotype-matched control monoclonal antibody MOPC21 in LB medium. Growth was monitored by light scattering at both 670 and 490 nm at the indicated intervals. Note that the slight elevation of the 50 μg/mL line is due to the use of outside wells on the microtiter plate where temperatures equilibrate faster.

FIG. 11 shows a ClustalW amino acid sequence alignment of the $V_H$ sequences from hybridomas 2D11, 3H6, 1E12 and 3A8. (2D11 $V_H$=SEQ ID NO: 1; 3H6 $V_H$=SEQ ID NO: 2; 1E12 $V_H$=SEQ ID NO: 3; 3A8 $V_H$=SEQ ID NO: 4). Highlighted sequences indicate the putative complementarity determining regions (CDR) in 2D11. A consensus sequence (SEQ ID NO: 31) is derived from these hybridoma sequences.

FIG. 12 shows a ClustalW amino acid sequence alignment of $V_L$ sequences from hybridomas 1E12 and 2D11 (1E12 $V_L$=SEQ ID NO: 10; 2D11 $V_L$=SEQ ID NO: 8). A consensus sequence (SEQ ID NO: 32) is derived from these two hybridoma sequences.

FIG. 13 shows a ClustalW amino acid sequence alignment of the $V_H$ sequences from hybridomas 2D11, 3H6, 1E12, 3A8, and 1C11 (2D11 $V_H$=SEQ ID NO: 1; 3H6 $V_H$=SEQ ID NO: 2; 1E12 $V_H$=SEQ ID NO: 3; 3A8 $V_H$=SEQ ID NO: 4; 1C11 $V_H$=SEQ ID NO: 5). A consensus sequence (SEQ ID NO: 6) is derived from these five hybridoma sequences.

FIGS. 14A-B show a ClustalW amino acid sequence alignment of the $V_L$ sequences. FIG. 14A shows $V_L$ alignment of hybridomas 1E12, 2D11, 3A8, 3H6, and 1C11 (1E12 $V_L$=SEQ ID NO: 10; 2D11 $V_L$=SEQ ID NO: 8; 3A8 $V_L$=SEQ ID NO: 11; 3H6 $V_L$=SEQ ID NO: 9; 1C11 $V_L$=SEQ ID NO: 12). A consensus sequence (SEQ ID NO: 13) is derived from these five hybridoma sequences. FIG. 14B shows $V_L$ alignment of hybridomas 1E12, 2D11, 3A8, and 3H6 (1E12 $V_L$=SEQ ID NO: 10; 2D11 $V_L$=SEQ ID NO: 8; 3A8 $V_L$=SEQ ID NO: 11; 3H6 $V_L$=SEQ ID NO: 9). A consensus sequence (SEQ ID NO: 33) is derived from these four hybridoma sequences.

FIG. 15 shows a ClustalW amino sequence alignment of the $V_H$ sequences from hybridomas 3A8 and 1C11 (3A8 $V_H$=SEQ ID NO: 4; 1C11 $V_H$=SEQ ID NO: 5). A consensus sequence (SEQ ID NO: 7) is derived from these two hybridoma sequences.

FIG. 16 shows a ClustalW amino acid sequence alignment of the $V_L$ sequences from hybridomas 3A8 and 1C11 (3A8 $V_L$=SEQ ID NO: 11; 1C11 $V_L$=SEQ ID NO: 12). A consensus sequence (SEQ ID NO: 14) is derived from these two hybridoma sequences.

FIG. 17A illustrates an alignment of the 1C11 $V_H$ domain (SEQ ID NO: 5) with a homologous amino acid sequence (SEQ ID NO: 19) encoded by the human gene IGV7-81 (see Genbank Accession AAH32733 and BC032733, each of which is hereby incorporated by reference in its entirety). A consensus sequence for the $V_H$ homologs (SEQ ID NO: 34) is shown. FIG. 17B illustrates an alignment of the 1C11 $V_L$ domain (SEQ ID NO: 12) with a homologous amino acid sequence (SEQ ID NO: 20) encoded by the human gene IGVK6D-21 (see Genbank Accession AAA58917 and M29469, each of which is hereby incorporated by reference in its entirety). A consensus sequence for the $V_L$ homologs (SEQ ID NO: 35) is shown.

FIGS. 20A-D are scanning electron miscroscopy (SEM) images of S. aureus grown in the absence (FIGS. 20A-B) or presence of anti-Gmd monoclonal antibodies of the present invention. FIG. 20C shows the effects of 50 μg/ml mAb 1E12 on Xen29 S. aureus and FIG. 20D shows the effects of 50 ng/ml mAb 1C11 on Xen29 S. aureus. Micrographs of representative fields were obtained at 50,000× (A&C), 2,000× (B) and 4,000× (D). Arrows identify sites where lysis has occurred, and document the surprising and unexpected effects of the present invention, as complement and immune effector cell independent lytic activity of an anti-S. aureus mAb has yet to be documented in the literature.

DETAILED DESCRIPTION OF THE INVENTION

Figure 1A:
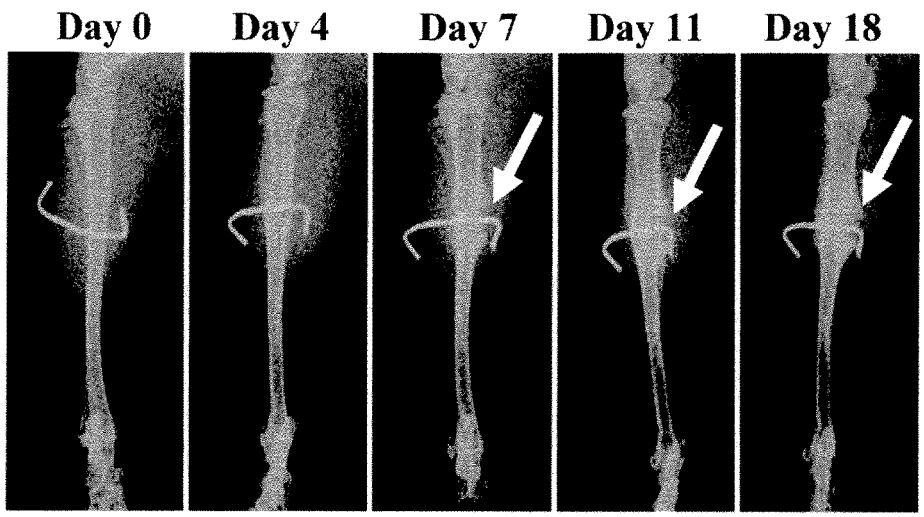
FIGS. 1A-C show the quantification of osteolysis from implant-associated osteomyelitis. A longitudinal series of X-rays from a representative mouse demonstrate the development of implant-associated osteolysis over time in this model (FIG. 1A). Medial views of reconstructed µCT (micro-computed tomography) images of representative tibiae from mice (N=5) that received a trans-tibial pin coated with *S. aureus* and were sacrificed on the indicated day (FIG. 1B). Also shown are control mice that received a trans-tibial pin coated with *S. aureus* and treated with parenteral gentamicin (Gent), or received a sterile pin. The osteolytic area around the pin was quantified as previously described (Li et al., "Quantitative Mouse Model of Implant-Associated Osteomyelitis and the Kinetics of Microbial Growth, Osteolysis, and Humoral Immunity," *J. Orthop. Res.* 26(1):96-105 (2008), which is hereby incorporated by reference in its entirety), and the data are presented as the mean+/−SD (*p<0.05 vs. Day 4; **p<0.05 vs. Gent Day 18) (FIG. 1C). There was no difference in the osteolysis area between the gentamicin and sterile pin controls.

In one aspect, the present invention relates to a monoclonal antibody that binds specifically to a Staphylococcus aureus glucosaminidase and inhibits in vivo growth of S. aureus. The monoclonal antibody of the present invention can be such that it targets S. aureus that is methicillin resistant.

As used herein, the term "antibody" is meant to include immunoglobulins derived from natural sources or from recombinant sources, as well as immunoreactive portions (i.e. antigen binding portions) of immunoglobulins. The monoclonal antibodies of the present invention may exist in or can be isolated in a variety of forms including, for example, substantially pure monoclonal antibodies, antibody fragments or binding portions, chimeric antibodies, and humanized antibodies (Ed Harlow and David Lane, USING ANTIBODIES: A LABORATORY MANUAL (Cold Spring Harbor Laboratory Press, 1999), which is hereby incorporated by reference in its entirety).

The monoclonal antibodies of the present invention are characterized by specificity for binding to *S. aureus* glucosaminidase or fragments thereof. The antibody specifically binds to an immuno-dominant epitope in the glucosaminidase (Gmd) sub-unit of *S. aureus* autolysin (Atl). These monoclonal antibodies inhibit in vivo growth of *S. aureus*.

Immuno-dominant antigen is a part of the antigenic determinant that is most easily recognized by the immune system and thus exerts the most influence on the specificity of the induced antibody. An "immuno-dominant epitope" refers to the epitope on an antigen that selectively provokes an immune response in a host organism to the substantial exclusion of other epitopes on that antigen.

Usually, the antigen likely to carry an immuno-dominant epitope can be identified by selecting antigens on the outer surface of the pathogenic organism. For example, most simple organisms, such as fungi, bacteria and viruses have one or two proteins that are exposed on the outer surface of the pathogenic organism. These outer surface proteins are most likely to carry the appropriate antigen. The proteins most likely to carry an immuno-dominant epitope can be identified in a Western assay in which total protein is run on a gel against serum from an organism infected with the pathogenic organism. Bound antibodies from the serum are identified by labeled anti-antibodies, such as in one of the well-known ELISA techniques. The immuno-dominant epitope can be identified by examining serum from a host organism infected with the pathogenic organism. The serum is evaluated for its content of antibodies that bind to the identified antigens that are likely to cause an immune response in a host organism. If an immuno-dominant epitope is present in these antigens, substantially all antibodies in the serum will bind to the immuno-dominant epitope, with little binding to other epitopes present in the antigen.

Atl is one of the catalytically distinct peptidoglycan hydrolases in *S. aureus* that is required to digest the cell wall during mitosis (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," *EMBO. J.* 17(16): 4639-46 (1998), which is hereby incorporated by reference in its entirety). In addition to being an essential gene for growth, scanning electron microscopy studies have demonstrated that anti Atl antibodies bound to *S. aureus* during binary fission localize to regions of the bacteria that are not covered by the cell wall (Yamada et al., "An Autolysin Ring Associated With Cell Separation of *Staphylococcus aureus*," *J. Bacteriol.* 178(6):1565-71 (1996), which is hereby incorporated by reference in its entirety).

The Atl enzyme is comprised of an amidase (62 kD) and glucosaminidase (53 kD), which are produced from the same Atl precursor protein via a cleavage process (Baba and Schneewind, "Targeting of Muralytic Enzymes to the Cell Division Site of Gram-Positive Bacteria: Repeat Domains Direct Autolysin to the Equatorial Surface Ring of *Staphylococcus aureus*," *Embo. J.* 17(16):4639-46 (1998); Komatsuzawa et al., "Subcellular Localization of the Major Autolysin, ATL and Its Processed Proteins in *Staphylococcus aureus*," *Microbiol Immunol.* 41:469-79 (1997); Oshida et al., "A *Staphylococcus aureus* Autolysin That Has an N-acetylmuramoyl-L-alanine Amidase Domain and an Endo-beta-N-acetylglucosaminidase Domain: Cloning, Sequence Analysis, and Characterization," *Proc. Nat'l. Acad. Sci. U.S.A.* 92(1):285-9 (1995), which are hereby incorporated by reference in their entirety). The autolysin is held to the cell wall by three ~150 amino acid cell wall binding domains R1, R2, and R3. In the final maturation step, proteolytic cleavage separates the aminidase domain and its associated R1 and R2 domains from the glucosaminidase and its associated N-terminal R3 domain.

By way of example, and without limitation, one exemplary *Staphylococcus aureus* glucosaminidase contains the amino acid sequence of SEQ ID NO: 36 below.

```
AYTVTKPQTT QTVSKIAQVK PNNTGIRASV YEKTAKNGAK

YADRTFYVTK ERAHGNETYV LLNNTSHNIP LGWFNVKDLN

VQNLGKEVKT TQKYTVNKSN NGLSMVPWGT KNQVILTGNN

IAQGTFNATK QVSVGKDVYL YGTINNRTGW VNAKDLTAPT

AVKPTTSAAK DYNYTYVIKN GNGYYYVTPN SDTAKYSLKA

FNEQPFAVVK EQVINGQTWY YGKLSNGKLA WIKSTDLAKE

LIKYNQTGMT LNQVAQIQAG LQYKPQVQRV PGKWTDANFN

DVKHAMDTKR LAQDPALKYQ FLRLDQPQNI SIDKINQFLK

GKGVLENQGA AFNKAAQMYG INEVYLISHA LLETGNGTSQ

LAKGADVVNN KVVTNSNTKY HNVFGIAAYD NDPLREGIKY

AKQAGWDTVS KAIVGGAKFI GNSYVKAGQN TLYKMRWNPA

HPGTHQYATD VDWANINAKI IKGYYDKIGE VGKYFDIPQY
```

In SEQ ID NO: 36, underlined residues correspond to residues 783 to 931 of the encoded autolysin, and represent the R3 domain. The remaining C-terminal residues (not underlined) correspond to the catalytic glucosaminidase domain.

In certain embodiments the monoclonal antibody of the present invention binds to a conserved epitope of *Staphylococcus aureus* glucosaminidase with an affinity greater than $10^{-9}$ M. As used herein, "epitope" refers to the antigenic determinant of *Staphylococcus aureus* glucosaminidase that is recognized by the monoclonal antibody. The epitope recognized by the antibody of the present invention may be a linear epitope, i.e. the primary structure of the amino acid sequence of glucosaminidase. Alternatively, the epitope recognized by the antibody of the present invention may be a non-linear or conformational epitope, i.e. the tertiary structure of glucosaminidase.

In certain embodiments, the monoclonal antibodies may bind specifically to the catalytic domain of the Gmd. In other embodiments, the monoclonal antibodies may bind specifically to the R3 domain.

Epitopes that are bound by five of the monoclonal antibodies identified herein lie wholly or at least partially within the R3 domain. By way of example, an epitope bound by mAb 3A8 lies within the region containing residues 776-842; an epitope bound by mAb 1C11 lies within the region containing residues 842-873; an epitope(s) bound by mAbs 2D11 and 1E12 are the same or different and lie within the region containing residues 842-948; and an epitope bound by mAb 3H6 lies within the region containing residues 907-948.

In certain embodiments, the monoclonal antibody of the present invention possesses S. aureus Gmd inhibitory activity, whereby the monoclonal antibody inhibits the activity of Gmd by at least 20%, at least 30%, at least 40% or at least 50%. In other embodiments, the monoclonal antibody inhibits the activity of Gmd by at least 60%, at least 70%, or at least 80%. Five monoclonal antibodies described herein (mAbs 3A8, 1C11, 2D11, 1E12, and 3H6) possess anti-Gmd inhibitory activity of about 70 to about 80 percent. It is a surprising and unexpected result that the antibodies of the present invention would bind a purported cell wall binding domain, the R3 domain, rather than a catalytic domain to inhibit enzymatic activity. Without being bound by theory, it is believed that the binding of the antibodies of the present invention to the R3 domain may trigger a conformational or electrostatic change in the catalytic domain of glucosaminidase.

Inhibition of Gmd activity can be measured in vitro. According to one approach, Gmd is first pre-titered to determine the concentration that will yield about a 50% reduction in $A_{490}$ in 60 minutes. Then 50 µL of antibody diluted in PBST is added to each well of a 96-well microtiter plate followed by 50 µL of appropriately diluted Gmd, and the mixture allowed to incubate for 5 or more minutes, and finally 100 µL of 0.15% mL is added and the initial $A_{490}$ measured. The plate is incubated at 37° C. and the $A_{490}$ measured at 30 and 60 minutes. Percent inhibition is calculated as $100 \cdot (1-(\Delta_{60}A_{490}$ inhibitor$/\Delta_{60}A_{490}$ no inhibitor control)).

In certain embodiments, the monoclonal antibody of the present invention possesses an ability to cause clustering or clumping of S. aureus, cell-independent lysis of S. aureus, or both. Examples of antibodies that possess an ability to cause clumping of S aureus include, without limitation, monoclonal antibodies 1C11, 1E12, 2D11, 3A8, and 3H6. One example of a lytic antibody is monoclonal antibody 1C11. This antibody binds to a unique epitope present in the R3 domain, displays between about 70 to about 80 percent Gmd inhibitory activity, and promotes cell-independent lysis of S. aureus.

The monoclonal antibodies of the present invention also inhibit in vivo growth of S. aureus. Inhibition of in vivo growth of S. aureus can be measured according to a number of suitable standards. In one such embodiment, the in vivo growth of S. aureus can be assessed according to a bioluminescence assay of the type described in the accompanying Examples. Specifically, bioluminescent S. aureus (Xen 29; ATCC 12600) (Francis et al., "Monitoring Bioluminescent Staphylococcus aureus Infections in Living Mice Using a Novel luxABCDE Construct," Infect. Immun. 68(6):3594-600 (2000); see also Contag et al., "Photonic Detection of Bacterial Pathogens in Living Hosts," Mol. Microbiol. 18(4):593-603 (1995), each of which is hereby incorporated by reference in its entirety) is used to dose a transtibial implant with 500,000 CFU prior to surgical implant. Five week old female BALB/cJ mice can receive an intraperitoneal injection of saline (n=10) or 1 mg of purified antibody in 0.25 ml saline 3 days prior to surgery. The mice can be imaged to assess bioluminescence on various days (e.g., 0, 3, 5, 7, 11, and 14) and a comparison of BLI images can be compared to assess whether the antibody inhibits in vivo growth of S. aureus relative to the saline control.

In one embodiment the monoclonal antibody of the present invention comprises a $V_H$ domain comprising one of the following amino acid sequences:

```
EVQLQESGPVLVKPGASVKMSCKASGYTFTDYYMNWVKQSHGKSLE

WIGVINPYNGDTTYSQKFKGKATLTVDKSSSTAYMELNSLTSEDSAVY

YCARNYDEYFDVWGTGTTVTVSSAKTTPPSVYPLAPGSAAQTNSMVT

LGCXVKG (SEQ ID NO: 1);
or

EVQLQESGPVLVKPGASVKLSCKASGYTFTDYFMNWVKQSHGKSLE

WIGVINPFNGGNRYNQNFKGKATLTVDKSSSTAYMELNSLTSEDSAV

YYCARGDYDSPWFDYWGQGTLVTVSAAKTTPPSVYPLAPGSAAQTN

SMVTLGCLVKGYSXSQ (SEQ ID NO: 2), where X is any amino acid;
or

EVQLQESGGGFVKPGGSLKLSCAASGFTFSTYVMSWVRQTPEKRLEW

VATISDGGGHTYYLDNVKGRFTISRDNAKNNLYLHMSHLKSEDTAMY

YCARAYYGSSYDAMDYWGQGTSVTVSSAKTTPPSVYPLAPGSAAQT

NSMVTLGCLVKG (SEQ ID NO: 3);
or

EVQLQESGGGLVQPGGSMKLSCAASGFTFSDAWMDWVRQSPEKGLE

WVAEIKDKTNNHATYYAESVKGRFTISRDVSKSRVFLQMNSLRPEDT

GIYYCTSGPYFDYWGQGTTLTVSSAKTTPPSVYPLAPGSAAQTNSMVT

LGCLVKGYFPE (SEQ ID NO: 4);
or

QIQLVQSGPELKKPGETVKISCKASGYTFTTYGMSWVNQAPGKGLKW

MGWINTYSGVPTYADDFKGRFVFSLETSASTAYLQINNLKNEDTATYF

CAREEYSSGYAAWFPYWGQGTLVTVSA (SEQ ID NO: 5), where X is any amino acid;
or
XXQLXXSGXXXXXPGXXXKXSCXASGXTFXXXXMXWVXQXXXKX

LXWXXXIXXXXXXXXXXYXXXXKGXXXXXXXXXXXXXXXXXXL

XXEDXXXYXCXXXXYXXXXXXXXXWGXGTXXTVSXXXXXXXXX

XXXXXXXXXXXXXXXXXXXXXXXXX, where X is any amino acid or deletion thereof; (consensus sequence SEQ ID NO: 6; see FIG. 13)
or
EVQLQESGXXXVXPGXSXKXSCXASGXTFXXXXMXWVXQXXXKXL

EWXXXIXXXXXXXXXXYXXXXKGXXTXXXDXXXXXXXXXXXLX

XEDXXXYYCXXXXYXXXXXXDXWGXGTXXTVSXAKTTPPSVYPL

APGSAAQTNSMVTLGCXVKGXXXXX. where X is any amino acid or deletion thereof, (consensus sequence SEQ ID NO: 31; see FIG. 11)
or
XXQLXXSGXXLXXPGXXXKXSCXASGXTFXXXXMXWVXQXPXKGL

XWXXXIXXXTXXXXXYAXXXKGRFXXSXXXSXSXXXLQXNXLXX

EDTXXYXCXXXXXXSGXXXXFXYWGQGTXXTVSXXXXXXXXXX
```

-continued

XXXXXXXXXXXXXXXXXXXXXXXXX, where X is any amino acid or deletion thereof; (consensus sequence SEQ ID NO: 7; see FIG. 15)
or
QXQLVQSGXEXKXPGXXVKXSCKASGYXFTTYGMXWVXQAPGXGL

XWMGWXNTYXGXPTYAXXFXGRFVFSXXTSASTAYLQIXXLKXEDX

AXYXCARXXXXXXXXXXXXXYWGQGTLVTVSA. where X is any amino acid or deletion thereof. (consensus sequence SEQ ID NO: 35, see FIG. 17A)

In another embodiment the monoclonal antibody of the present invention comprises a $V_L$ domain comprising one of the following amino acid sequences:

DIVMTQSPAIMSASPGEKVTMTCSASSSVSYMYWYQQKPGSSPRLLIY

DTSNLASGVPVRFSGSGSGTSYSLTISRMEAEDAATYYCQQWSSYPLT

FG (SEQ ID NO: 8);
or
QMTQTTSSLSASLGDRVTISCSASQGISNYLNWYQQKPDGTVKLLIYY

TSSLHSGVPSRFSGGGSGTDYSLSISNLEPEDIATYYCQQYSKLPWTFG

GGTKLEIK, (SEQ ID NO: 9);
or
DIVITQSPAIMSASLGERVTMTCTASSSVSSSYLHWYQQKPGSSPKXWI

YSTSNLASGVPARFSGSGSGTSYSLTISSMEAEDAATYYCHQYHRSPW

TFGGGT (SEQ ID NO: 10);
or
DIVMTQSHKFMSTSVGDRVSITCKASQDVSTAVAWYQQKPGQSPKLL

IYWTSTRHTGVPDRFTGSGSGTDFTLTISSVQAKDLALYYCQQHYTTP

YTFGGGTKLEIK, (SEQ ID NO: 11);
or
DIVLTQSPATLSVTPGDSVSLSCRASQSISNNLHWYQQKSHESPRLLIEY

ASRSISGIPSRFSGGGSGTDFTLSINSVESEDFGLYFCQQSNSWPLTFGA

GTKLELK, (SEQ ID NO: 12);
or
DIXXTQXXXXXSXXXGXXVXXXCXASXXXSXXXXXWYQQKXXXX

XXXXIXXXSXXXXGXPXRFXGXGSGTXXXLXIXXXXXXDXXXYXCX

QXXXXPXTFGXGTXXXXX. where X is any amino acid or deletion thereof; (consensus sequence SEQ ID NO: 13, see FIG. 14A)
or
DIVXTQSXXXXSXXXGDXVSXXCXASQXXSXXXXWYQQKXXXSPXL

LIXXXSXXXXGXPXRFXGXGSGTDFTLXIXSVXXXDXXLYXCQQXXX

XPXTFGXGTKLEXK, where X is any amino acid or deletion thereof; (consensus sequence SEQ ID NO: 14, see FIG. 16)
or
DIVXTQSPAIMSASXGEXVTMTCXASSSVSXXYXXWYQQKPGSSPXX

XIYXTSNLASGVPXRFSGSGSGTSYSLTISXMEAEDAATYYCXQXXXX

PXTFGXXX, where Xis any amino acid or deletion thereof; (consensus sequence SEQ ID NO: 32, see FIG. 12)
or
DIXXTQXXXXXSXSXSXXSXXXSXSSXXXSXXXXXWYQQKPXXXXX

XXIYXTSXXXXCGVPPXRFXGXGSGTXXXLXISXXXXXDXAXYYCXQ

XXXXPXTFGGGTXXXXX, where X is any amino acid or deletion thereof; (consensus sequence SEQ ID NO: 33, see FIG. 14B)
or
XIVLTQSPXXXSVTPXXXVXXXCRASQSIXXXLHWYQQXXXXSPXLLI

XYASXSXSGXPSRFSGXGSGTDFTLXINSXEXEDXXXYXCXQSXSXPL

TFGXGTKXEXK, where X is any amino acid or deletion thereof. (consensus sequence SEQ ID NO: 37, see FIG. 17B)

Antibodies of the present invention may also be synthetic antibodies. A synthetic antibody is an antibody which is generated using recombinant DNA technology, such as, for example, an antibody expressed by a bacteriophage. Alternatively, the synthetic antibody is generated by the synthesis of a DNA molecule encoding and expressing the antibody of the invention or the synthesis of an amino acid specifying the antibody, where the DNA or amino acid sequence has been obtained using synthetic DNA or amino acid sequence technology which is available and well known in the art.

The monoclonal antibody of the present invention can be humanized. Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. A human antibody is an antibody produced by a human or an antibody having an amino acid sequence corresponding to an antibody produced by a human.

An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," Nature 321:522-525 (1986); Riechmann et al., "Reshaping Human Antibodies for Therapy," Nature 332:323-327 (1988); Verhoeyen et al., "Reshaping Human Antibodies: Grafting an Antilysozyme Activity," Science 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Humanized antibodies can be produced using various techniques known in the art. Immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the humanized antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc. Nat'l. Acad. Sci. U.S.A.* 95:6157-6162 (1998); Hoogenboom et al., "By-passing Immunisation. Human Antibodies From Synthetic Repertoires of Germline VH Gene Segments Rearranged in vitro," *J. Mol. Biol.* 227:381-8 (1992); Marks et al., "By-passing Immunization. Human Antibodies from V-gene Libraries Displayed on Phage," *J. Mol. Biol.* 222: 581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

Based on a BLAST search of Genbank using the 1C11 V. and $V_L$ domain amino acid sequences, homologous sequences within the human genome were identified as IGVH7-81 and IGVK6D-21, respectively. Alignments of these homologous V. and $V_L$ domains (SEQ ID NOS: 19 and 20, respectively) with the corresponding 1C11 V. and $V_L$ domains are illustrated in FIGS. 17A-B, respectively. The $V_H$ and $V_L$ domains share a surprisingly high degree of identity, respectively about 75% and 67% over the region of homology (i.e., excluding V. CDR3H region). These IGVH7-81 and IGVK6D-21 sequences can be used to prepare a substantially pure monoclonal antibody of the present invention. Because the CDR3H is not encoded by the V. gene, a suitable D region will need to be spliced into the missing domain region. Any one of several candidate D regions can be used (e.g., IGHD5-5, 18 or 12*01).

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988); Houston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988); Bird et al, "Single-Chain Antigen-Binding Proteins," *Science* 242:423-426 (1988), which are hereby incorporated by reference in their entirety, or other methods known in the art.

It may further be desirable, especially in the case of antibody fragments, to modify the antibody to increase its serum half-life. This can be achieved, for example, by incorporation of a salvage receptor binding epitope into the antibody fragment by mutation of the appropriate region in the antibody fragment or by incorporating the epitope binding site into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In preparing these antibody mimics the CDR sequences of the $V_H$ and/or $V_L$ chains can be grafted into the variable loop regions of these antibody mimics (see FIGS. 11 and 17 for putative CDR domains). The grafting can involve a deletion of at least two amino acid residues up to substantially all but one amino acid residue appearing in a particular loop region along with the substitution of the CDR sequence. Insertions can be, for example, an insertion of the CDR domain at one or more locations of a particular loop region. The antibody mimics of the present invention preferably possess an amino acid sequence which is at least 50% homologous to the $V_H$ and/or $V_L$ chains sequences disclosed in the present application. The deletions, insertions, and replacements on the polypeptides can be achieved using recombinant techniques beginning with a known nucleotide sequence (see infra).

Methods for monoclonal antibody production may be achieved using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., *S. aureus* glucosaminidase or peptide fragments thereof).

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Thus, a second aspect of present invention relates to a cell line that expresses a monoclonal antibody of the present invention. In one embodiment the monoclonal antibody of the present invention is produced by a hybridoma cell line designated as 1C11, 1E12, 2D11, 3A8, or 3H6. In another embodiment, the monoclonal antibody of the present invention (or a binding portion thereof) is produced by a recombinant cell or cell line.

As noted above, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate host cells that express and secrete monoclonal antibodies. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The present invention also includes a nucleic acid molecule encoding a polypeptide of the present invention. In one embodiment the nucleic acid is DNA. Examples of such DNA sequences are those that comprise a $V_H$ and/or $V_L$ encoding sequence of the present invention. DNA sequence encoding for hybridoma 2D11 $V_H$ (closest germ line match: J558.18.108) has the nucleotide sequence (SEQ ID NO: 21) as follows:

GAGGTGCAGCTGCAGGAGTCTGGACCTGTGCTGGTGAAGCCTGGGGCTTC

AGTGAAGATGTCCTGTAAGGCTTCTGGATACACATTCACTGACTACTATA

TGAACTGGGTGAAGCAGAGCCATGGAAAGAGCCTTGAGTGGATTGGAGTT

ATTAATCCTTACAACGGTGATACTACCTACAGCCAGAAGTTCAAGGGCAA

GGCCACATTGACTGTTGACAAGTCCTCCAGCACAGCCTACATGGAGCTCA

ACAGCCTGACATCTGAGGACTCTGCAGTCTATTACTGTGCAAGAAATTAC

GACGAGTACTTCGATGTCTGGGGCACAGGGACCACGGTCACCGTCTCCTC

AGCCAAAACGACACCCCATCTGTCTATCCACTGGCCCTGGATCTGCTG

CCCAAACTAACTCCATGGTGACCCTGGGATGCCNGGTCAAGGGC

DNA sequence encoding for hybridoma 3H6 $V_H$ (closest germ line match: J558.18.108) has the nucleotide sequence (SEQ ID NO: 23) as follows:

GAGGTGCAGCTGCAGGAGTCTGGACCTGTGCTGGTGAAGCCTGGGGCTTC

AGTGAAGCTGTCCTGTAAGGCTTCTGGATACACATTCACTGACTACTTTA

TGAACTGGGTGAAGCAGAGCCATGGAAAGAGCCTTGAGTGGATTGGAGTT

ATTAATCCTTTCAACGGTGGTAATAGGTACAACCAGAACTTCAAGGGCAA

GGCCACATTGACTGTTGACAAGTCCTCCAGCACAGCCTACATGGAGCTCA

ACAGCCTGACATCTGAGGACTCTGCAGTCTATTACTGTGCAAGAGGGGAC

TATGACTCCCCCTGGTTTGATTACTGGGGCCAAGGGACTCTGGTCACTGT

CTCTGCAGCCAAAACGACACCCCATCTGTCTATCCACTGGCCCCTGGAT

CTGCTGCCCAAACTAACTCCATGGTGACCCTGGGATGCCTGGTCAAGGGC

TATTCCCNGAGCCAGTG

DNA sequence encoding for hybridoma 1E12 $V_H$ (closest germ line match: 7183.46 VH7) has the nucleotide sequence (SEQ ID NO: 25) as follows:

GAGGTGCAGCTGCAGGAGTCTGGGGGAGGCTTCGTGAAGCCTGGAGGGTC

CCTGAAACTCTCCTGTGCAGCCTCTGGATTCACTTTCAGTACCTATGTCA

TGTCTTGGGTTCGCCAGACTCCGGAAAAGAGGCTGGAGTGGGTCGCAACC

ATTAGTGATGGTGGTGGTCATACTTACTATCTAGACAATGTAAAGGGCCG

ATTCACCATCTCCAGAGACAATGCCAAGAACAACCTGTACCTGCACATGA

GCCATCTGAAGTCTGAGGACACAGCCATGTATTACTGTGCAAGAGCTTAC

TACGGTAGTAGTTACGACGCTATGGACTACTGGGGTCAAGGAACCTCAGT

CACCGTCTCCTCAGCCAAAACGACACCCCATCTGTCTATCCACTGGCCC

CTGGATCTGCTGCCCAAACTAACTCCATGGTGACCCTGGGATGCCTGGTC

AAGGGC

DNA sequence encoding for hybridoma 3A8 $V_H$ (closest germ line match: VHJ606.4.8.2) has the nucleotide sequence (SEQ ID NO: 27) as follows:

GAGGTGCAGCTGCAGGAGTCTGGAGGAGGCTTGGTGCAACCTGGAGGATC

CATGAAACTCTCTTGTGCTGCCTCTGGATTCACTTTTAGTGACGCCTGGA

TGGACTGGGTCCGCCAGTCTCCAGAGAAGGGGCTTGAGTGGGTTGCTGAA

ATTAAAGACAAAACTAATAATCATGCAACATACTATGCTGAGTCTGTGAA

AGGGAGGTTCACCATCTCAAGAGATGTTTCCAAAAGTCGTGTCTTCCTGC

AAATGAACAGCTTAAGACCTGAAGACACTGGCATTTATTACTGTACGTCT

GGGCCATATTTTGACTACTGGGGCCAAGGCACCACTCTCACAGTCTCCTC

AGCCAAAACGACACCCCATCTGTCTATCCACTGGCCCCTGGATCTGCTG

CCCAAACTAACTCCATGGTGACCCTGGGATGCCTGGTCAAGGGCTATTTC

CCTGAG

DNA sequence encoding for hybridoma 1C11 $V_H$ (closest germline match: VH 9-15, DST4-057B1-6, JH3) has the nucleotide sequence (SEQ ID NO: 29) as follows:

CAGATCCAGTTGGTACAGTCTGGACCTGAGCTGAAGAAGCCTGGAGAGAC

AGTCAAGATCTCCTGCAAGGCTTCTGGGTATACCTTCACAACGTATGGAA

TGAGCTGGGTGAATCAGGCTCCAGGAAAGGGTTTAAAGTGGATGGGCTGG

ATAAACACCTACTCTGGAGTGCCAACATATGCTGATGACTTCAAGGGACG

-continued
GTTTGTCTTCTCTTTGGAAACCTCTGCCAGCACTGCCTATTTGCAGATCA

ACAACCTCAAAAATGAGGACACGGCTACATATTTCTGTGCAAGAGAGGAG

TACAGCTCAGGCTACGCGGCCTGGTTTCCTTACTGGGGCCAAGGGACTCT

GGTCACTGTCTCTGCA

DNA sequence encoding for the 2D11 $V_L$ (closest germ line match: at4) has the nucleotide sequence (SEQ ID NO: 22) as follows:

GATATTGTGATGACCCAGTCTCCAGCAATCATGTCTGCATCTCCAGGGGA

GAAGGTCACCATGACCTGCAGTGCCAGCTCAAGTGTAAGTTACATGTACT

GGTACCAGCAGAAGCCAGGATCCTCCCCCAGACTCCTGATTTATGACACA

TCCAACCTGGCTTCTGGAGTCCCTGTTCGCTTCAGTGGCAGTGGGTCTGG

GACCTCTTACTCTCTCACAATCAGCCGAATGGAGGCTGAGGATGCTGCCA

CTTATTACTGCCAGCAGTGGAGTAGTTACCCGCTCACGTTCGGT

DNA sequence encoding for the 3H6 $V_L$ (closest germ line match: cp9, JK1) has the nucleotide sequence (SEQ ID NO: 24) as follows:

CAGATGACACAGACTACGTCCTCCCTGTCTGCCTCTCTGGGAGACAGAGT

CACCATCAGTTGCAGTGCAAGTCAGGGCATTAGCAATTATTTAAACTGGT

ATCAGCAGAAACCAGATGGAACTGTTAAACTCCTGATCTATTACACATCA

AGTTTACACTCAGGAGTCCCATCAAGGTTCAGTGGCGGTGGGTCTGGGAC

AGATTATTCTCTCTCCATCAGCAACCTGGAACCTGAAGATATTGCCACTT

ACTATTGTCAGCAGTATAGTAAGCTTCCTTGGACGTTCGGTGGAGGCACC

AAGCTGGAAATCAAA

DNA sequence encoding for the 1E12 $V_L$ (closest germ line match: ai4) has the nucleotide sequence (SEQ ID NO: 26) as follows:

GATATTGTGATCACCCAGTCTCCAGCAATCATGTCTGCATCTCTAGGGGA

ACGGGTCACCATGACCTGCACTGCCAGCTCAAGTGTAAGTTCCAGTTACT

TACACTGGTACCAGCAGAAGCCAGGATCCTCCCCCAAACTNTGGATTTAT

AGCACATCCAACCTGGCTTCTGGAGTCCCAGCTCGCTTCAGTGGCAGTGG

GTCTGGGACCTCTTACTCTCTCACAATCAGCAGCATGGAGGCTGAAGATG

CTGCCACTTATTACTGCCACCAGTATCATCGTTCCCCATGGACGTTCGGT

GGAGGCACC

DNA sequence encoding for the 3A8 $V_L$ (closest germ line match: KV 19-25, JK2) has the nucleotide sequence (SEQ ID NO: 28) as follows:

GACATTGTGATGACCCAGTCTCACAAATTCATGTCCACATCAGTAGGAGA

CAGGGTCAGCATCACCTGCAAGGCCAGTCAGGACGTGAGTACTGCTGTAG

CCTGGTATCAACAAAAACCAGGGCAATCTCCTAAACTACTGATTTACTGG

ACATCCACCCGGCACACTGGAGTCCCTGATCGCTTCACAGGCAGTGGATC

-continued
TGGGACAGATTTTACTCTCACCATCAGCAGTGTGCAGGCTAAAGACCTGG

CACTTTATTACTGTCAGCAACATTATACCACTCCGTACACGTTCGGAGGG

GGGACCAAGCTGGAAATAAAA

DNA sequence encoding for 1C11 $V_L$ (closest germ line match: VK23-43, JK5) has the nucleotide sequence (SEQ ID NO: 30) as follows:

GATATTGTGCTAACTCAGTCTCCAGCCACCCTGTCTGTGACTCCAGGAGA

TAGCGTCAGTCTTTCCTGCAGGGCCAGCCAAAGTATTAGCAACAACCTAC

ACTGGTATCAACAAAAATCACATGAGTCTCCAAGGCTTCTCATCGAATAT

GCTTCCCGGTCCATCTCTGGGATCCCCTCTAGGTTCAGTGGCGGTGGATC

AGGGACAGATTTCACTCTCAGTATCAACAGTGTGGAGTCTGAAGATTTTG

GATTGTATTTCTGTCAACAGAGTAACAGCTGGCCGCTCACGTTCGGTGCT

GGGACCAAGCTGGAGCTGAAA

Still a further aspect of the present invention is a DNA construct comprising a DNA molecule that encodes an antibody or binding portion of the present invention, a promoter-effective DNA molecule operably coupled 5' of the DNA molecule, and a transcription termination DNA molecule operably coupled 3' of the DNA molecule. The present invention also encompasses an expression vector into which the DNA construct of the present invention is inserted. A synthetic gene for the polypeptides of the present invention can be designed such that it includes convenient restriction sites for ease of mutagenesis and uses specific codons for high-level protein expression (Gribskov et al., "The Codon Preference Plot: Graphic Analysis of Protein Coding Sequences and Prediction of Gene Expression," *Nuc. Acids. Res.* 12:539-549 (1984), which is hereby incorporated by reference in its entirety).

The gene may be assembled as follows: first the gene sequence can be divided into parts with boundaries at designed restriction sites; for each part, a pair of oligonucleotides that code opposite strands and have complementary overlaps of about 15 bases can be synthesized; the two oligonucleotides can be annealed and single strand regions can be filled in using the Klenow fragment of DNA polymerase; the double-stranded oligonucleotide can be cloned into a vector, such as, the pET3a vector (Novagen) using restriction enzyme sites at the termini of the fragment and its sequence can be confirmed by a DNA sequencer; and these steps can be repeated for each of the parts to obtain the whole gene. This approach takes more time to assemble a gene than the one-step polymerase chain reaction (PCR) method (Sandhu et al., "Dual Asymetric PCR: One-Step Construction of Synthetic Genes," *BioTech.* 12:14-16 (1992), which is hereby incorporated by reference in its entirety). Mutations could likely be introduced by the low fidelity replication by Taq polymerase and would require time-consuming gene-editing. Recombinant DNA manipulations can be performed according to SAMBROOK & RUSSELL, MOLECULAR CLONING: A LABORATORY MANUAL (2d ed. 1989), which is hereby incorporated by reference in its entirety, unless otherwise stated. To avoid the introduction of mutations during one-step PCR, high fidelity/low error polymerases can be employed as is known in the art.

Desired mutations can be introduced to the polypeptides sequence of the present invention using either cassette mutagenesis, oligonucleotide site-directed mutagenesis techniques (Deng & Nickoloff, "Site-Directed Mutagenesis of Virtually any Plasmid by Eliminating a Unique Site," *Anal. Biochem.* 200:81-88 (1992), which is hereby incorporated by reference in its entirety), or Kunkel mutagenesis (Kunkel et al., "Rapid and Efficient Site-Specific Mutagenesis Without Phenotypic Selection," *Proc. Natl. Acad. Sci. USA* 82:488-492 (1985); Kunkel et al., "Rapid and Efficient Site-Specific Mutagenesis Without Phenotypic Selection," *Methods Enzymol.* 154:367-382 (1987), which are hereby incorporated by reference in their entirety).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the nucleotide sequence encoding a polypeptide according to the present invention, sequencing can be performed to confirm that the designed mutations (and no other mutations) were introduced by mutagenesis reactions.

In contrast, Kunkel mutagenesis can be utilized to randomly produce a plurality of mutated polypeptide coding sequences which can be used to prepare a combinatorial library of polypeptides for screening. Basically, targeted loop regions (or C-terminal or N-terminal tail regions) can be randomized using the NNK codon (N denoting a mixture of A, T, G, C, and K denoting a mixture of G and T) (Kunkel et al., "Rapid and Efficient Site-Specific Mutagenesis Without Phenotypic Selection," *Methods Enzymol.* 154:367-382 (1987), which is hereby incorporated by reference in its entirety).

Regardless of the approach used to prepare the nucleic acid molecules encoding the polypeptide according to the present invention, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressors, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with this aspect of the invention, the polynucleotides of the present invention are inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6×His tags (BD Biosciences, Franklin Lakes, N.J.). Viral vectors suitable for use in carrying out this aspect of the invention include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of antibodies or antibody fragments that are produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV 5 (tac) promoter or other *E. coli* promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. The promoters can be constitutive or, alternatively, tissue-specific or inducible. In addition, in some circumstances inducible (TetOn) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine- Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," *Methods in Enzymology*, 68:473-82 (1979), which is hereby incorporated by reference in its entirety.

The present invention also includes a host cell transformed with the DNA construct of the present invention. The host cell can be a prokaryote or a eukaryote. Host cells suitable for expressing the polypeptides of the present invention include any one of the more commonly available gram negative bacteria. Suitable microorganisms include *Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N meningitides, Haemophilus influenzae, H pleuropneumoniae, Pasteurella haemolytica, P. multilocida, Legionella pneumophila, Treponema pallidum, T. denticola, T. orales, Borrelia burgdorferi, Borrelia* spp., *Leptospira interrogans, Klebsiella pneumoniae, Proteus vulgaris, P. morganii, P. mirabilis, Rickettsia prowazeki, R. typhi, R. richettsii, Porphyromonas (Bacteroides) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida,* and *Yersinia pestis.*

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecule of the present invention. Mammalian cell lines commonly used in the art include Chinese hamster ovary cells, HeLa cells, baby hamster kidney cells, COS cells, and many others. Suitable insect cell lines include those susceptible to baculoviral infection, including Sf9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct of the present invention is co-transfected with baculovirus DNA, such as AcNPV, to facilitate the production of a recombinant virus. Subsequent recombinant viral infection of Sf cells results in a high rate of recombinant protein production. Regardless of the expression system and host cell used to facilitate protein production, the expressed antibodies, antibody fragments, or antibody mimics of the present invention can be readily purified using standard purification methods known in the art and described in PHILIP L. R. BONNER, PROTEIN PURIFICATION (Routledge 2007), which is hereby incorporated by reference in its entirety.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a humanized (or chimeric) antibody, as discussed above. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

A third aspect of the present invention is related to a pharmaceutical composition comprising a carrier and one or more monoclonal antibodies or one or more binding portions thereof in accordance with the present invention. This pharmaceutical composition may contain two or more antibodies or binding fragments where all antibodies or binding fragments recognize the same epitope. Alternatively, the pharmaceutical composition may contain an antibody or binding fragment mixture where one or more antibodies or binding fragments recognize one epitope of *S. aureus* Gmd and one or more antibodies or binding fragments recognize a different epitope of *S. aureus* Gmd. For example, the mixture may contain one or more antibodies of the present invention that bind specifically to an R3 domain of *Staphylococcus aureus* glucosaminidase in combination with any other antibody that binds to glucosaminidase, such as an antibody that binds to the catalytic domain of glucosaminidase. The pharmaceutical composition of the present invention further contains a pharmaceutically acceptable carrier or other pharmaceutically acceptable components as described infra In accordance with one embodiment, the pharmaceutical composition includes one or more of mAbs 1C11, 2D11, 3H6, 1E12, and 3A8 in a pharmaceutically acceptable carrier. In accordance with another embodiment, the pharmaceutical composition includes two or more of mAbs 1C11, 2D11, 3H6, 1E12, and 3A8 in a pharmaceutically acceptable carrier.

A pharmaceutical composition containing the monoclonal antibodies of the present invention can be administered to a subject having or at risk of having *Staphylococcus* infection. Various delivery systems are known and can be used to administer the antibodies of the present invention. Methods of introduction include but are not limited to intradermal, intramuscular, intraperitoneal, intravenous, subcutaneous, intranasal, epidural, and oral routes. The therapeutic agent can be administered, for example by infusion or bolus injection, by absorption through epithelial or mucocutaneous linings (e.g., oral mucosa, rectal and intestinal mucosa, and the like) and can be administered together with other biologically active agents, such as chemotherapeutic agents, antibiotic agents, or other immunotherapeutic agents. Administration can be systemic or local, i.e., at a site of Staph infection or directly to a surgical or implant site.

The pharmaceutical composition of the present invention can further comprise administering a second therapeutic agent to the patient, wherein the second therapeutic agent is an antibiotic agent or immunotherapeutic agent. Exemplary antibiotic agents include, without limitation, vancomycin, tobramycin, cefazolin, erythromycin, clindamycin, rifampin, gentamycin, fusidic acid, minocycline, co-trimoxazole, clindamycin, linezolid, quinupristin-dalfopristin, daptomycin, tigecycline, dalbavancin, telavancin, oritavancin, ceftobiprole, ceftaroline, iclaprim, the carbapenem CS-023/RO-4908463, and combinations thereof. Exemplary immunotherapeutic agents include, without limitation, tefibazumab, BSYX-A110, Aurexis™, and combinations thereof. The above lists of antibiotic agents and immunotherapeutic agents are intended to be non-limiting examples; thus, other antibiotic agents or immunotherapeutic agents are also contemplated. Combinations or mixtures of the second therapeutic agent can also be used for the purposes of the present invention. These agents can be administered contemporaneously or as a single formulation.

The pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein, typically in purified form, together with a suitable amount of carrier so as to provide the form for proper administration to the patient. The formulations correspond to the mode of administration.

Effective doses of the compositions of the present invention, for the treatment of the above described bacterial infections vary depending upon many different factors, including mode of administration, target site, physiological state of the patient, other medications administered, and whether treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime. For prophylactic treatment against *Staphylococcus* bacterial infection, it is intended that the pharmaceutical composition(s) of the present invention can be administered prior to exposure of an individual to the bacteria and that the resulting immune response can inhibit or reduce the severity of the bacterial infection such that the bacteria can be eliminated from the individual. For example, the monoclonal antibody or the pharmaceutical composition can be administered prior to, during, and/or immediately following a surgical procedure, such as joint replacement or any surgery involving a prosthetic implant.

For passive immunization with an antibody or binding fragment of the present invention, the dosage ranges from about 0.0001 to about 100 mg/kg, and more usually about 0.01 to about 5 mg/kg, of the host body weight. For example, dosages can be about 1 mg/kg body weight or about 10 mg/kg body weight, or within the range of about 1 to about 10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be daily, weekly, monthly, or yearly. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies.

A further aspect of the invention relates to an active vaccine (e.g., pharmaceutical composition) that includes a carrier and an antigenic molecule comprising at least a fragment of the *S. aureus* glucosaminidase. The antigenic molecule can be in the form of (i) a fusion protein that includes the glucosaminidase polypeptide and an adjuvant polypeptide or (ii) an immunogenic conjugate that includes the glucosaminidase polypeptide conjugated to another immunogenic molecule.

By way of example, and without limitation, suitable fusion proteins of the present invention include those containing an adjuvant polypeptide selected from the group of flagellin, human papillomavirus (HPV) L1 or L2 proteins, herpes simplex glycoprotein D (gD), complement C4 binding protein, a toll-like receptor-4 (TLR4) ligand, and IL-1β.

The fusion polypeptide or protein of the present invention can be generated using standard techniques known in the art. For example, the fusion polypeptide can be prepared by translation of an in-frame fusion of the polynucleotide sequences of the present invention and the adjuvant, i.e., a hybrid or chimeric gene. The hybrid gene encoding the fusion polypeptide is inserted into an expression vector which is used to transform or transfect a host cell. Alternatively, the polynucleotide sequence encoding the polypeptide of the present invention is inserted into an expression vector in which the polynucleotide encoding the adjuvant is already present. The peptide adjuvant of the fusion protein can be fused to the N-, or preferably, to the C-terminal end of the glucosaminidase polypeptide of the present invention.

Fusions between the polypeptides of the present invention and the protein adjuvant may be such that the amino acid sequence of the polypeptide of the present invention is directly contiguous with the amino acid sequence of the adjuvant. Alternatively, the polypeptide portion may be coupled to the adjuvant by way of a short linker sequence. Suitable linker sequences include glycine rich linkers (e.g., GGGS$_{2-3}$ (SEQ ID NO: 37), serine-rich linkers (e.g., GS$_N$), or other flexible immunoglobulin linkers as disclosed in U.S. Pat. No. 5,516,637 to Huang et al, which is hereby incorporated by reference in its entirety.

Suitable immunogenic conjugates of the present invention include, but are not limited to, those containing an immunogenic carrier molecule covalently or non-covalently bonded to any glucosaminidase polypeptide. Any suitable immunogenic carrier molecule can be used. Exemplary immunogenic carrier molecules include, but are in no way limited to, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

The pharmaceutical composition in the form of an active vaccine can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, and/or non-infective *Bordetella pertussis*.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

In prophylactic applications, pharmaceutical compositions containing the immunogenic glucosaminidase polypeptides are administered to a patient susceptible to, or otherwise at risk of, the bacterial infection in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, pharmaceutical compositions containing a monoclonal antibody or binding fragment according to the present invention are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose, which is identified supra. In both prophylactic and therapeutic regimes, agents are usually administered in several dosages until a sufficient response has been achieved. Typically, the response is monitored and repeated dosages are given if the response starts to wane.

Treatment dosages should be titrated to optimize safety and efficacy. The amount of immunogen depends on whether adjuvant is also administered, with higher dosages being required in the absence of adjuvant. The amount of an immunogen for administration sometimes varies from 1-500 μg per patient and more usually from 5-500 μg per injection for human administration. Occasionally, a higher dose of 1-2 mg per injection is used. Typically about 10, 20, 50, or 100 μg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at time intervals, such as 6 week intervals. Another regimen consists of an immunization followed by booster injections 1, 2, and 12 months later. Alternatively, booster injections can be provided on a regular or irregular basis, as indicated by monitoring of immune response.

A fourth aspect the present invention relates to a method of treating an *S. aureus* infection that includes administering to a patient having an *S. aureus* infection an effective amount of a monoclonal antibody or binding fragment thereof or a pharmaceutical composition of the present invention.

In one embodiment of this aspect of the invention the method of treating *S. aureus* infection further comprises repeating said administering. The method of treating *S. aureus* infection can be such that the administering is carried out systemically or carried out directly to a site of the *S. aureus* infection.

The method of treating *S. aureus* infection can be used to treat *S. aureus* infection at sites which include, without limitation, infection of the skin, muscle, cardiac, respiratory tract, gastrointestinal tract, eye, kidney and urinary tract, and bone or joint infections.

In one embodiment, this method is carried out to treat osteomyelitis by administering an effective amount of the monoclonal antibody or binding fragment thereof or the pharmaceutical composition of the present invention to a patient having an *S. aureus* bone or joint infection. Administration of these agents or compositions can be carried out using any of the routes described supra; however, administration directly to the site of the bone or joint infection is preferred.

A sixth aspect of the present invention relates to a method of introducing an orthopedic implant into a patient that includes administering to a patient in need of an orthopedic implant an effective amount of a monoclonal antibody, binding portion, or pharmaceutical composition of the present invention, and introducing the orthopedic implant into the patient.

In one embodiment, the method of introducing an orthopedic implant includes administering to the patient in need of the orthopedic implant an effective amount of a monoclonal antibody or binding fragment or a pharmaceutical composition containing the same, directly to the site of implantation. Alternatively, or in addition, the orthopedic implant can be coated or treated with the monoclonal antibody or binding fragment or a pharmaceutical composition containing the same before, during, or immediately after implantation thereof at the implant site.

The orthopedic implant can be a joint prosthesis, graft or synthetic implant. Exemplary joint prosthetics includes, without limitation, a knee prosthetic, hip prosthetic, finger prosthetic, elbow prosthetic, shoulder prosthetic, temporomandibular prosthetic, and ankle prosthetic. Other prosthetics can also be used. Exemplary grafts or synthetic implants include, without limitation, an artificial intervertebral disk, meniscal implant, or a synthetic or allograft anterior cruciate ligament, medial collateral ligament, lateral collateral ligament, posterior cruciate ligament, Achilles tendon, and rotator cuff. Other grafts or implants can also be used.

In one embodiment, the method of introducing an orthopedic implant is intended to encompass the process of installing a revision total joint replacement. Where infection, particularly Staph infection of an original joint replacement occurs, the only viable treatment is a revision total joint replacement. In this embodiment, the infected joint prosthesis is first removed and then the patient is treated for the underlying infection. Treatment of the infection occurs over an extended period of time (i.e. 6 months), during which time the patient is immobile (or has only limited mobility) and receives high doses of antibiotics to treat the underlying infection and optionally one or more monoclonal antibodies or binding portions, or pharmaceutical compositions of the present invention. Upon treatment of the underlying infection, the new joint prosthesis is installed. Immediately prior (i.e., within the two weeks preceding new joint prosthesis installation) and optionally subsequent to installation of the new joint prosthesis, the patient is administered one or more monoclonal antibodies or binding portions, or pharmaceutical compositions of the present invention. This treatment can be repeated one or more times during the post-installation period. Antibiotic treatment may be administered in combination with or concurrently with the one or more monoclonal antibodies or binding portions, or pharmaceutical compositions of the present invention. These treatments are effective to prevent infection or reinfection during the revision total joint replacement.

The methods of treatment according to the present invention can be used to treat any patient in need, however, the methods are particularly useful for immuno-compromised patients of any age, as well as patients that are older than 50 years of age.

EXAMPLES

The present invention is illustrated by reference to the following examples. These examples are not intended to limit the claimed invention.

Example 1—A Murine Transtibial Model of Implant-Associated Osteomyelitis

Orthopedic implant-associated OM occurs for both intramedullary devices (i.e. joint prostheses) and transcortical implants (i.e. external fixation devices, FIG. 1A). Although the infection rate of fixation devices is 2.5 times greater, and has an incidence of over 8-times that of total joint prostheses, it is not considered to be as serious because the revision surgery is much simpler (Darouiche, "Treatment of Infections Associated With Surgical Implants," *N Engl. J. Med.* 350(14):1422-9 (2004), which is hereby incorporated by reference in its entirety). While most cases involving an infected transcortical implant can be resolved in a single surgery to relocate the pin and treating the abscess independently, the majority of infected prostheses must undergo two revision surgeries (Darouiche, "Treatment of Infections Associated With Surgical Implants," *N Engl. J. Med.* 350 (14):1422-9 (2004), which is hereby incorporated by reference in its entirety). The first is needed to cure the infection, and the second replaces the prosthesis. Thus, from a clinical significance standpoint, the field has focused primarily on models of implant-associated OM that involve an intramedullary device with the UAMS-1 (ATCC 49230) strain of *S. aureus* (Daum et al., "A Model of *Staphylococcus aureus* Bacteremia, Septic Arthritis, and Osteomyelitis in Chickens," *J. Orthop. Res.* 8(6):804-13 (1990); Rissing et al., "Model of Experimental Chronic Osteomyelitis in Rats," *Infect. Immun.* 47(3):581-6 (1985); Passl et al., "A Model of Experimental Post-Traumatic Osteomyelitis in Guinea Pigs," *J. Trauma* 24(4):323-6 (1984); Worlock et al., "An Experimental Model of Post-Traumatic Osteomyelitis in Rabbits," *Br. J. Exp. Pathol.* 69(2):235-44 (1988); Varshney et al., "Experimental Model of Staphylococcal Osteomyelitis in Dogs," *Indian J. Exp. Biol.* 27(9):816-9 (1989); Kaarsemaker et al., "New Model for Chronic Osteomyelitis With *Staphylococcus aureus* in Sheep," *Clin. Orthop. Relat. Res.* 339:246-52 (1997), which are hereby incorporated by reference in their entirety). Unfortunately, this approach has significant limitations, most notably the inability to generate reproducible (temporal and spatial) lesions. In an effort to overcome this the location of the infection was guided to the diaphysis by fracturing the tibia immediately after inserting an intramedullary pin containing $1 \times 10^6$ CFU, using an Einhorn device as described previously (Zhang et al., "Cyclooxygenase-2 Regulates Mesenchymal Cell Differentiation Into the Osteoblast Lineage and is Critically Involved in Bone Repair," *J. Clin. Invest.* 109(11):1405-15 (2002), which is hereby incorporated by reference in its entirety). It was found that implantation of an infected transcortical pin always produces lesions adjacent to the pin, and never results in chronic OM in other regions of the tibia or hematogenous spreading in mice (FIGS. 1A-C).

Figure 1B:
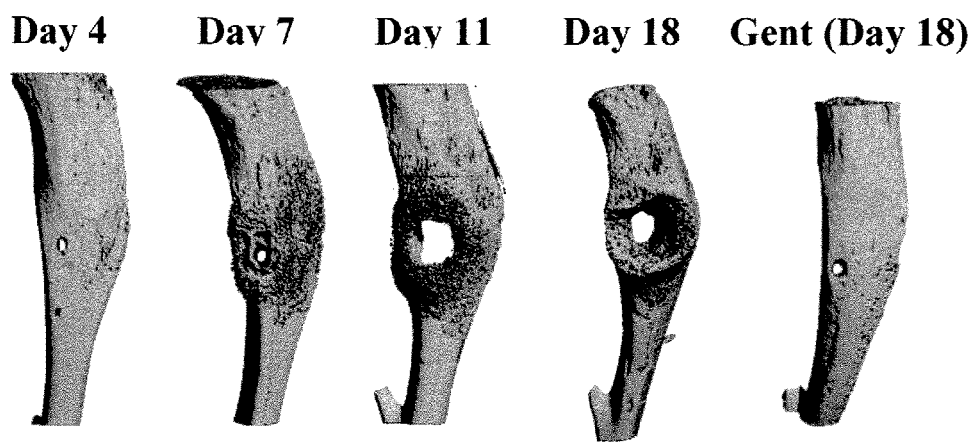
Figure 1C:
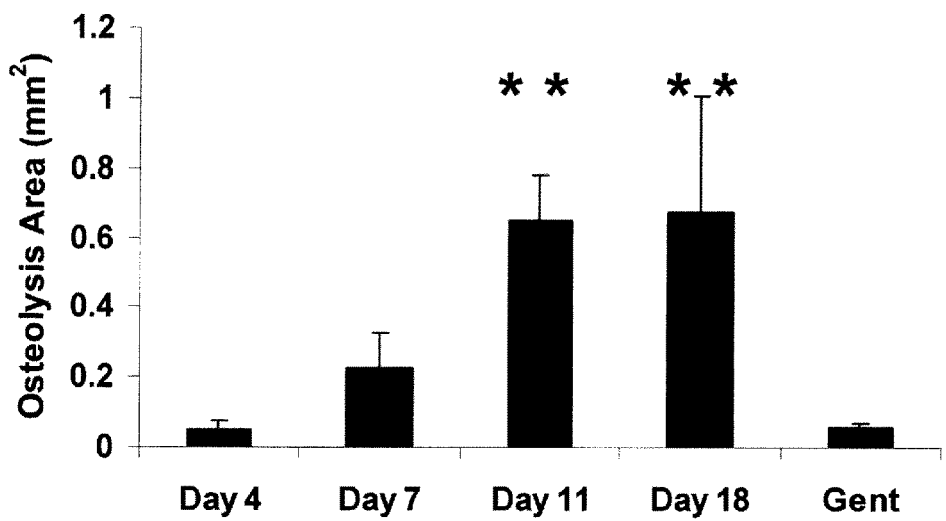

To quantify the osteolysis, a time-course study was performed in which the infected tibiae were analyzed by µCT (FIGS. 1B-C). These results are consistent with sequestrum formation in which osteoclastic bone resorption around the infected implant occurs with concomitant reactive periosteal bone formation.

The presence of OM in the mice was confirmed histologically. FIGS. 2A-H demonstrate that the tibial transcortical pin model contains all of the salient features of chronic OM including: sequestrum and involucrum formation, osteoclastic resorption of the cortical bone and Gram stained extracellular bacteria and biofilm that reside in the necrotic bone surrounding the implant. None of the negative controls, including heat killed *S. aureus* and non-pathogenic *E. coli*, demonstrated these features.

Example 2—Real Time PCR Quantitation of Osteomyelitis

There are no known methods to quantify OM. Since it is impossible to effectively extract live bacteria from infected bone to determine bacterial load by classical colony forming units (CFU), a real time PCR method was developed to quantify the number of recoverable nuc genes in DNA samples, as is done to test for contamination in cheese (Hein et al., "Comparison of Different Approaches to Quantify *Staphylococcus aureus* Cells by Real-Time Quantitative PCR and Application of This Technique for Examination of Cheese,"*Appl. Environ. Microbiol.* 67(7):3122-6 (2001), which is hereby incorporated by reference in its entirety) and blood (Palomares et al., "Rapid Detection and Identification of *Staphylococcus aureus* From Blood Culture Specimens Using Real-Time Fluorescence PCR,"*Diagn. Microbiol. Infect. Dis.* 45(3):183-9 (2003), which is hereby incorporated by reference in its entirety), as a surrogate outcome measure of bacterial load.

RTQ-PCR for the *S. aureus*-specific nuc gene can be performed using primers 5'-GCGATTGATGGTGATACG-GTT-3' (SEQ ID NO: 15) and 5'-AGCCAAGCCTTGAC-GAACTAA-3' (SEQ ID NO: 16) that amplify a previously described 269-bp product (Hein et al., "Comparison of Different Approaches to Quantify *Staphylococcus aureus*

Cells by Real-Time Quantitative PCR and Application of This Technique for Examination of Cheese,"*Appl. Environ. Microbiol.* 67(7):3122-6 (2001), which is hereby incorporated by reference in its entirety). The reactions can be carried out in a final volume of 20 µl consisting of 0.3 µM primers, 1× Sybr Green PCR Super Mix (BioRad, Hercules, Calif.), and 2 µl of the purified tibia DNA template. The samples can be assayed using a Rotor-Gene RG 3000 (Corbett Research, Sydney, AU).

To control for the integrity of the DNA template between samples, RTQ-PCR can also be performed for the mouse β-actin gene that detects a 124-bp product using primers 5'-AGATGTGAATCAGCAAGCAG-3' (SEQ ID NO: 17) and 5'-GCGCAAGTTAGGTTTTGTCA-3' (SEQ ID NO: 18). Using PCR primers specific for murine β-actin, *S. aureus* nuc, and rRNA genomic DNA, the specificity of these PCRs and the ability to amplify the predicted products was demonstrated (Li et al., "Quantitative Mouse Model of Implant-Associated Osteomyelitis and the Kinetics of Microbial Growth, Osteolysis, and Humoral Immunity," *J. Orthop. Res.* 26(1):96-105 (2008), which is hereby incorporated by reference in its entirety). Then, using purified plasmid DNA containing the nuc gene, or *S. aureus* genomic DNA, a dose response experiment was performed and it was determined that the detection limit for this RTQ-PCR is ~100 copies (Li et al., "Quantitative Mouse Model of Implant-Associated Osteomyelitis and the Kinetics of Microbial Growth, Osteolysis, and Humoral Immunity," *J. Orthop. Res.* 26(1):96-105 (2008), which is hereby incorporated by reference in its entirety). This assay has been used to quantify the in vivo bacterial load as a secondary outcome measure of infection and efficacy of the passive immunization.

Figure 3A:
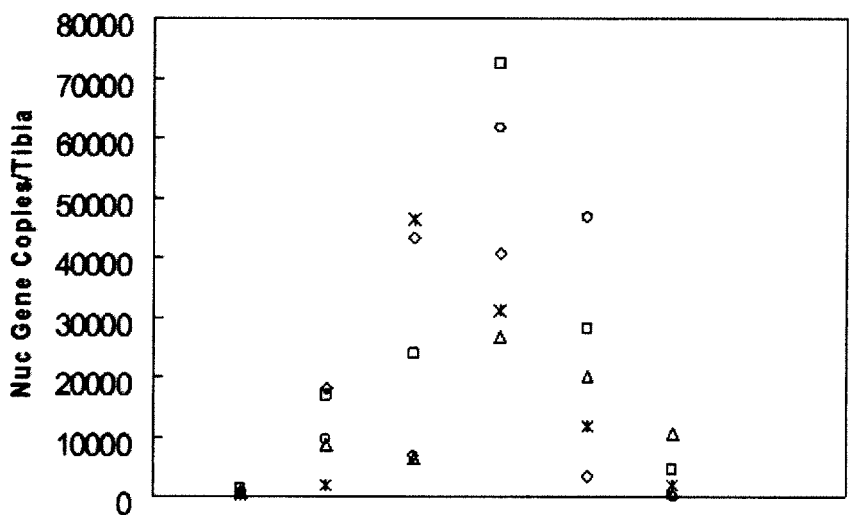
FIGS. 3A-C show the inverse correlation between bacterial load and humoral immunity against *S. aureus* antigens during the establishment of chronic osteomyelitis. A time course study was performed in which mice were given an infected transcortical pin containing $1 \times 10^6$ CFU of *S. aureus* in their tibia and sacrificed on the indicated day. At sacrifice, DNA was purified from the infected tibia and RTQ-PCR was performed to determine the Ct values for *S. aureus* nuc. Using a standard curve shown, this number was converted to the recoverable nuc genes per tibia. To control for the integrity of the samples, the recoverable nuc gene per tibia value was standardized to the Ct value for mouse β-actin for each sample. From this conversion the bacterial load was derived as "Nuc Gene Copies/Tibia." The data from each mouse is shown in FIG. 3A as an individual point, and the mean+/−SD for each time point (n=5) is presented in FIG. 3B. To assess the development of anti-*S. aureus* specific antibodies during the establishment of OM, serum was taken from each mouse in the group that was sacrificed on day 18, before infection (day 0) and on days 4, 7, 11, 14 and 18 after infection. This serum was used as the primary antibody in Western blots of total *S. aureus* extract that were then probed with HRP-conjugated antibodies that are specific for mouse IgG as shown in FIG. 3C. The data show that there is a steady increase in bacterial growth from day 0 to day 11, when the host first develops specific antibodies against the bacteria. As the titer of the anti-*S. aureus* antibodies increases the bacterial load drops, suggesting that the antibodies are protective. The Western blots also clearly identify four immuno-dominant antigens of 26, 34, 38 and 56 kDa (arrows). It has also been demonstrated that Xen 29 also induces antibodies against these same 26, 34, 38 and 56 kDa proteins.
Figure 3B:
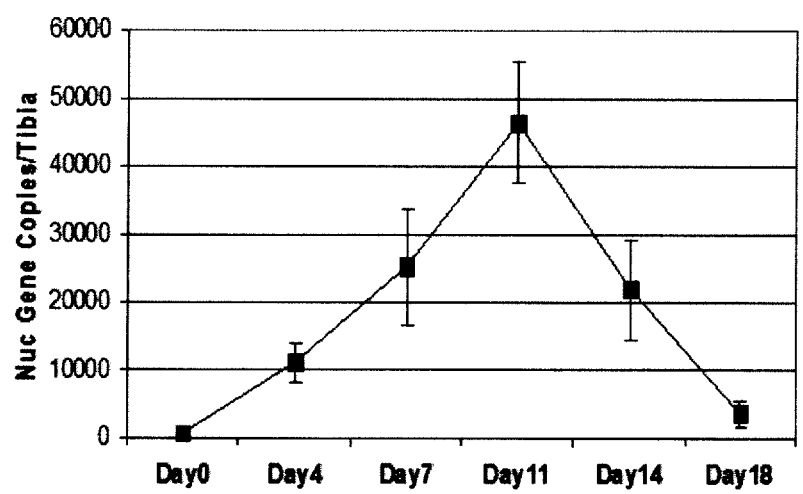
Figure 3C:
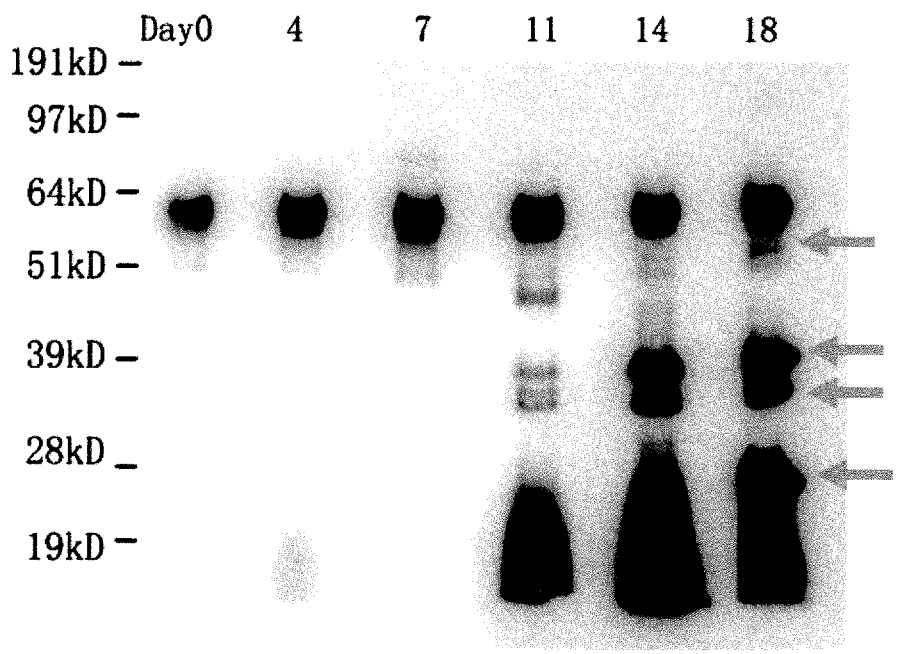

Example 3—Kinetics of Infection and Humoral Immunity During the Establishment of Osteomyelitis To quantify microbial pathogenesis and host immunity during the establishment of osteomyelitis, a time course study was performed in which mice were given an infected transcortical pin implant in their tibia, and the bacterial load and the host humoral response was determined over time by nuc/β-actin RTQ-PCR and western blot, respectively (FIGS. 3A-C). The results indicate a clear inverse correlation between infection and humoral immunity. Consistent with classical microbial pathogenesis and acquired immunity to extracellular bacteria, these results indicate that the bacteria immediately establish themselves and enter an exponential growth phase, which is extinguished by a neutralizing humoral response after 11 days. Based on the coincidence of the peak bacterial load with the genesis of high affinity IgG antibodies against specific bacterial proteins, it is evident that these "immuno-dominant" antigens elicit a functional immune response that is both diagnostic and protective against the establishment of OM.

Example 4—Identification and Cloning of the Glucosaminidase Subunit of *S. aureus* Autolysin as 56 kDa Immuno-Dominant Antigen that Elicits a Specific IgG2b Response During the Establishment of OM To further characterize the humoral response during the establishment of OM, the prevalence of Ig isotypes in the serum of mice was determined over the first two weeks of infection by ELISA (Li et al., "Quantitative Mouse Model of Implant-Associated Osteomyelitis and the Kinetics of Microbial Growth, Osteolysis, and Humoral Immunity,"*J. Orthop. Res.* 26(1):96-105 (2008), which is hereby incorporated by reference in its entirety). The results showed that the mice initiate a classical IgM response in the first week that converts to a specific IgG2b response in the second week, which has recently been shown to have potent opsonic and protective activities against *S. aureus* antigens (Maira-Litran et al., "Comparative Opsonic and Protective Activities of *Staphylococcus aureus* Conjugate Vaccines Containing Native or Deacetylated Staphylococcal Poly-N-acetyl-beta-(1-6)-glucosamine," *Infect. Immun.* 73(10):6752-62 (2005), which is hereby incorporated by reference in its entirety).

To elucidate the molecular identity of the immuno-dominant antigens identified in FIG. 3C, subtractive Western blotting of total *S. aureus* extract was performed that was separated by 2D-PAGE (FIGS. 4A-C). This analysis revealed a polypeptide that was not detected by the pre-immune serum, but had strong reactivity with the day 14 post-immune serum. The protein was isolated from a preparative Coomassie blue stained gel, digested with trypsin, and analyzed by matrix-assisted laser desorption/ionization (MALDI), which resolved 70 individual peptide peaks. The amino acid sequence from every peptide was a 100% match with the known sequence of the Gmd subunit of *S. aureus* Alt. Interestingly, others have also recently found Atl to be an immuno-dominant antigen in a rabbit tibia model of MRSA OM (Brady et al., "Identification of *Staphylococcus aureus* Proteins Recognized by the Antibody-Mediated Immune Response to a Biofilm Infection," *Infect. Immun.* 74(6):3415-26 (2006), which is hereby incorporated by reference in its entirety).

To confirm that the spot picked from the 2D-PAGE gel in FIG. 4C was the relevant immuno-dominant antigen, a recombinant 6-His tagged fusion protein was generated by cloning the 1,465 bp coding region of the 53 kDa glucosaminidase subunit of *S. aureus* autolysin into the XhoI-BamHI site of the pET-28a(+) expression plasmid (Novagen), which contains the lac I promoter for IPTG induction. Following DNA sequencing, the plasmid was used to transform BL21 *E. coli*, which were used to make recombinant His-glucosaminidase (His-Gmd). This recombinant protein was then used to evaluate the reactivity of pre-immune and immune sera. The results showed that the IPTG induced 57 kDa recombinant protein is only recognized by immune serum, thus confirming that Gmd is a *S. aureus* immuno-dominant antigen. This experiment was repeated with antisera from mice infected with Xen 29, and confirmed that C57Bl/6 also generate Gmd specific antibodies against this bioluminescent strain of *S. aureus*.

Example 5—In Vivo Bioluminescence Imaging of Lux Transformed *S. aureus* as a Longitudinal Outcome Measure of OM and Bacterial Growth Although the RTQ-PCR method of quantifying OM in mouse model is very useful, there are three major limitations to this approach. First, it is not longitudinal, as analysis requires sacrifice of the mice to harvest the DNA. Second, it is very labor intense and requires great care during the DNA isolation, PCR and data analysis. Third, detection of *S. aureus* genomic DNA (nuc genes) cannot distinguish between bacteria that are in an active growth phase vs. dormant bacteria tightly packed in a biofilm. Thus, RTQ-PCR cannot be readily used to assess mAb effect on bacterial growth in vivo.

Figures 5A, 5B:
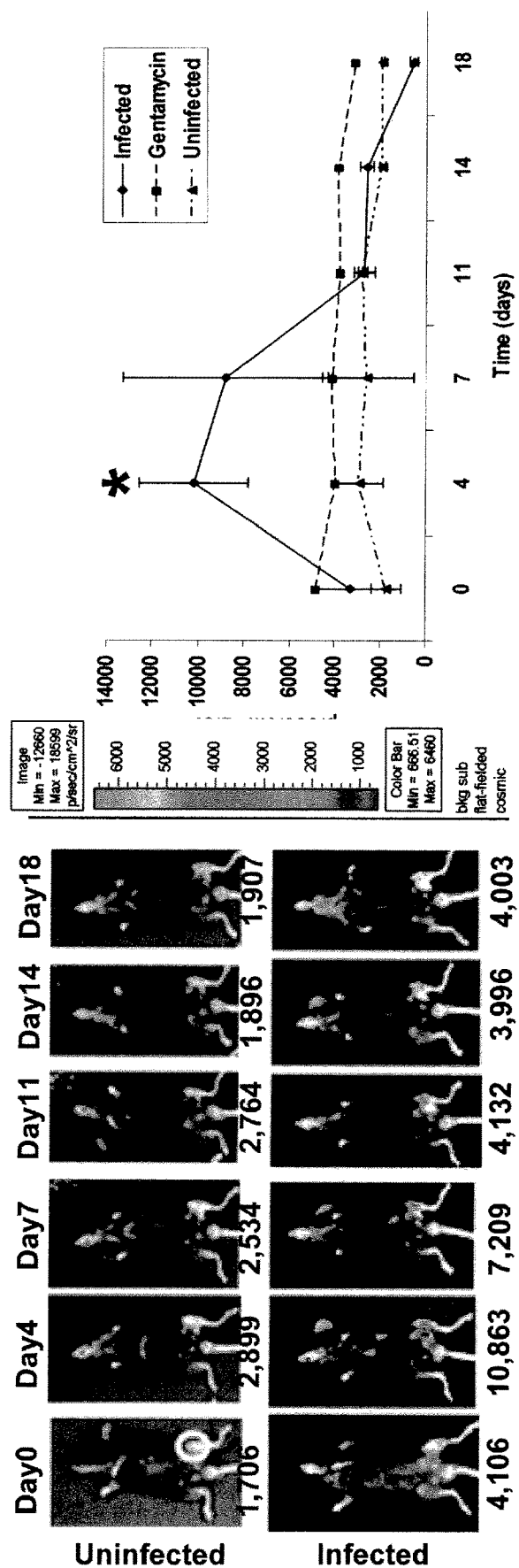
FIGS. 5A-B show bioluminescent imaging (BLI) quantification of bacterial growth during the establishment of chronic osteomyelitis.

To overcome these shortcomings, the present invention relates to a highly innovative approach to monitor pathogens in vivo using bioluminescence imaging (Contag et al., "Photonic Detection of Bacterial Pathogens in Living Hosts," *Mol. Microbiol.* 18(4):593-603 (1995), which is hereby incorporated by reference in its entirety). More recently, P. R. Contag and colleagues have generated bioluminescent *S. aureus* (Xen 29; ATCC 12600) for this purpose (Francis et al., "Monitoring Bioluminescent *Staphylococcus aureus* Infections in Living Mice Using a Novel luxABCDE Construct," *Infect. Immun.* 68(6):3594-600 (2000), which is hereby incorporated by reference in its entirety). FIGS. 5A-B demonstrate how this approach is adapted in the model of OM of the present invention. In a time-course studies with Xen29, only background signal was detected in mice that received a sterile pin or infected mice treated with parenteral gentamycin. In contrast, the BLI of infected, untreated tibiae demonstrated a sharp 4-fold increase from baseline on day 4, which subsequently dropped to background levels by day 11.

Example 6—Recombinant Gmd Vaccine Protects Mice from Implant-Associated OM

To assess the potential of an anti-autolysin passive immunization for OM, an initial active recombinant Gmd vaccine study was performed in which mice (n=20) were immunized as follows: Group 1 (PBS in adjuvant (negative control)); Group 2 (20 µg *S. aureus* Xen 29 total proteome extract emulsified 1:1 with equal volume of adjuvant (positive control)); Group 3 (20 µg His-glucosaminidase in adjuvant). A 150 µl emulsion of each vaccine was injected intramuscularly (i.m.) 28 day prior to challenge. Booster immunizations (i.m.; 20 µg protein in Freund's incomplete adjuvant) were performed 14 days prior to challenge.

Figure 6B:
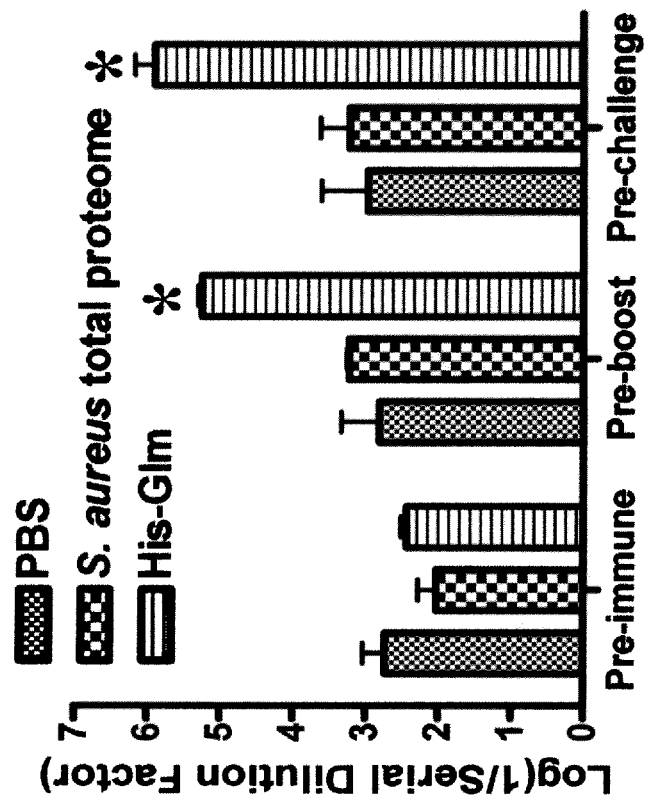
FIGS. 6A-B show that functional anti-Gmd ELISA demonstrated the efficacy of recombinant Gmd vaccine.
Figure 6A:
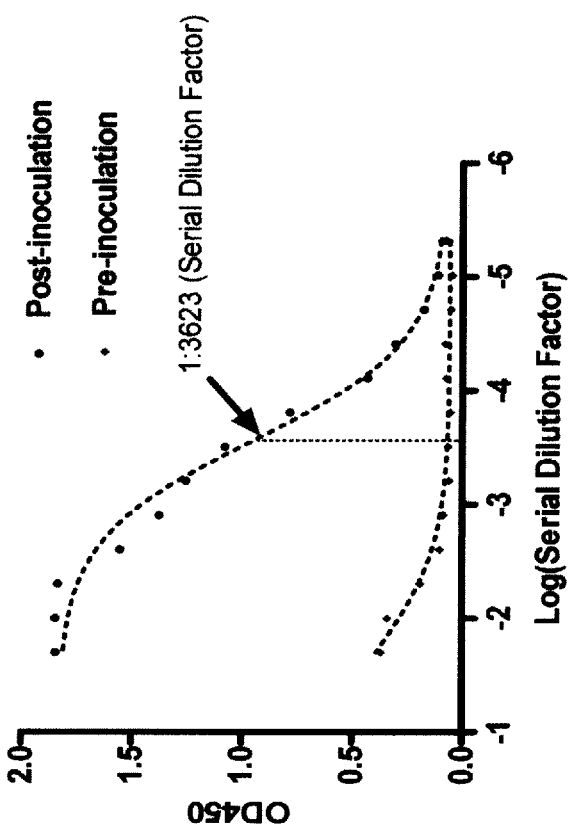

To assess the vaccine efficacy in these mice, an anti-Gmd ELISA was developed (FIG. 6A) and used to quantify serum antibody titers before initial immunization, before booster immunization, and before the bacterial challenge (FIG. 6B). Remarkably, the results demonstrated that only the recombinant vaccine elicited a high titer immune response. To assess the efficacy of these vaccines, the immunized mice were challenged with a Xen29 infected transtibial pin as described in the preceding Example (see FIG. 5A-C), BLI was performed on day 3, and the mice were euthanized for nuc RTQ-PCR on day 11. Remarkably, 18 out of the 20 mice immunized with *S. aureus* total proteome died within 48 hr of the challenge; thus efficacy data from that group are not available. While only speculative explanations can be provided for this observation (i.e. hyper-immunity to other antigens), the fact that no death occurred in any of the other groups and that the deaths were reproduced in the 4 cohorts of 5 mice in Group 2 indicates that the results are real. For this reason, this immunization protocol should not be used as a positive control for future studies. It also highlights the safety concerns with active vaccines, and supports the rationale of a passive immunization with purified mAb or binding fragments thereof.

Figures 7A, 7B, 7C:
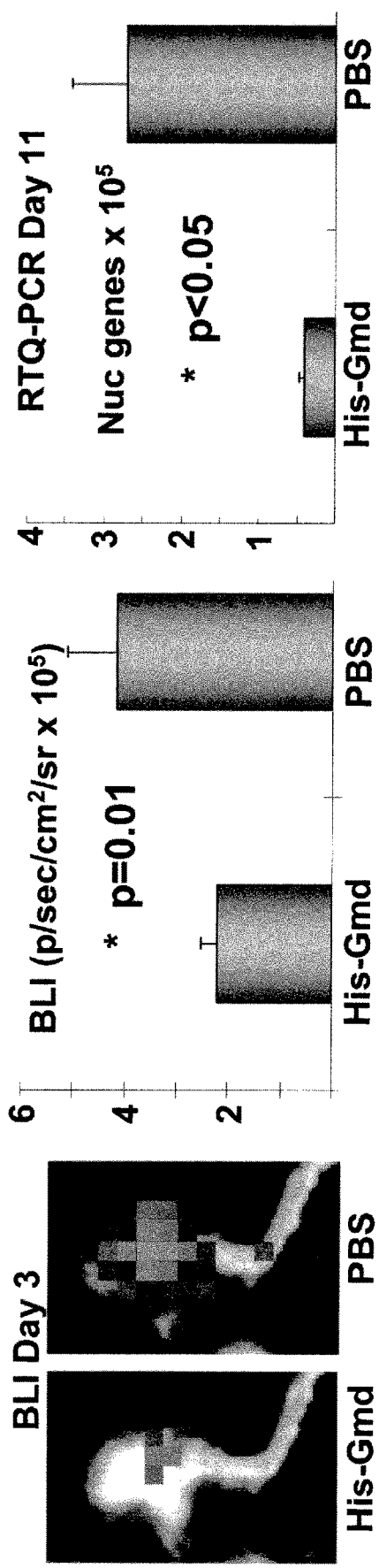
FIGS. 7A-C show that recombinant His-Gmd vaccine protects mice from implant-associated OM. The mice (n=20) were challenged with a Xen29 infected transtibial pin as described in the accompanying Examples, BLI was performed on day 3, and the mice were euthanized for nuc RTQ-PCR on day 11. An image of the BLI from a representative mouse in Group 1 & 3 is shown (FIG. 7A), and the mean+/−SD is presented to show the significant reduction BLI (FIG. 7B). This translated into a significant decrease in amplifiable nuc genes (mean+/−SD) on day 11 (FIG. 7C).

The BLI and nuc RTQ-PCR data from Groups 1 and 3 are presented in FIGS. 7A-C. The results clearly demonstrate a significant reduction of BLI detected in the His-Gmd immunized mice (FIGS. 7A-B), which shows a decrease in planktonic growth of the bacteria. Consistent with this finding, it was observed that there was a significant reduction in the number of nuc genes at the peak of the bacterial load in this model (day 11). Thus, these data demonstrate that the recombinant Gmd vaccine can protect mice from OM in the model.

Example 7—Generation and Screening of Mouse Anti-Gmd Monoclonal Antibodies

Based on the success of the His-Gmd immunization described in Example 6, this protocol was used to generate mouse anti-Gmd mAb. Standard procedures were used to generate the mAb. Out of an initial pool of hybridomas that were prepared, a first subset was selected following screened by ELISA for anti-Gmd activity and a second subset possessing higher affinity were selected following a western dot-blot assay.

Five of the hybridoma cell lines were selected based on their apparent high affinity for Gmd ($\leq 10^{-9}$M) and the putative epitope for these regions being found within the R3 domain of Gmd. Because the R3 domain is not the catalytic domain of the Gmd protein, it was unexpected that these monoclonal antibodies would possess as significant anti-Gmd inhibitory activity. The five selected hybridomas were 1C11, 1E12, 2D11, 3A8 and 3H6. All secreted mouse IgG1 antibodies.

Example 8—Alteration of In Vitro Growth of *Staphylococcus aureus* Xen29 by Monoclonal Anti-glucosaminidase Antibodies Frozen aliquots of each cell line (1C11, 1E12, 2D11, 3A8 and 3H6) were obtained directly from the vendor who prepared them at our request (Precision Antibodies, Inc., Columbia, Md.). The frozen cells were thawed, and then washed in Dulbecco's Modified Eagle's Medium (DMEM) supplemented with 50 µg/mL gentamicin and 10% fetal bovine serum (FBS). Harvested culture supernatant was clarified by centrifugation (10 min, 1000×g) and frozen.

Thirty mL of culture supernatant from each cell line was thawed at 37-45° C. and filtered through a 0.22 µm filter. Each was then purified on a 5 mL bed-volume Protein G-agarose column (GE Healthcare HiTrap™ Protein G HP, Cat. No. 17-0405-03, Lot #10036021). In the place of the pump for which these columns are designed, fluids were added by means of luer-lock syringes fitted by adapters to the top of the column. The column was first washed with PBS to remove the ethanol preservative and then culture supernatants were added at 5-6 mL/min, followed by six column volumes of PBS to wash out unbound protein. Adsorbed antibody was eluted with two column volumes of 0.1 M glycine, pH 2.7, into a collection vessel containing 1 mL of 1.0 M Tris, pH 8.0, to neutralize the eluted product. The column was then washed with four column volumes of PBS in preparation for the next antibody, or with PBS containing 0.02% $NaN_3$ for storage.

The eluted antibodies were concentrated and dialyzed into PBS in Pierce® concentrators (Thermo Scientific 7 mL/20K MWCO, Cat. No. 87750, lot #KH137631A) by successive centrifugations at 3500×g, 40 min, 4° C. Antibody concentration was determined by ELISA using MOPC21 or Phe12.15 (both mouse IgG1) as standards. Unlabelled goat antimouse IgG (Southern Biotechnology Cat. No. 1030-01) was adsorbed onto 96-well NUNC Maxisorp microtiter plates at 5 µg/mL in PBS, 100 µL per well, one hour RT or overnight at 4° C. Wells were blocked by the addition of 200 µL of 3% BSA in PBS for one hour RT or overnight at 4° C. Blocked plates were washed twice with PBS containing 0.05% Tween 20 (PBST) and ready for use. Samples were prepared as serial dilutions in PBST and 100 µL was added to wells designated for standards and samples. The samples were incubated for one hour, RT, and then washed 4 times with PBST from a squirt bottle. The captured mouse antibody was detected by the addition to each well of 100 µL of HRP-conjugated goat anti-mouse IgG (HRP-GAM; Southern Biotechnology, Cat. No. 1031-05), diluted 1:2000 in PBST, and incubated for one hour, RT. After washing the plates 4 times with PBST from a squirt bottle, the chromogenic HRP substrate ABTS (Southern Biotechnology, Cat. No. 0401-01) was added, 100 µL per well. Color was allowed to develop for 5-10 minutes, RT. Antibody concentrations were determined by projecting sample color values onto the standard curves and then correcting for dilution. These concentrations were used for titration studies to determine their effect on *S. aureus* growth.

*S. aureus* Xen29 (Kadurugamuwa et al., "Rapid Direct Method for Monitoring Antibiotics in a Mouse Model of Bacterial Biofilm Infection," *Antimicrob Agents Chemother* 47:3130-7 (2003) and Kadurugamuwa et al., "Noninvasive Optical Imaging Method to Evaluate Postantibiotic Effects on Biofilm Infection In Vivo," *Antimicrob Agents Chemother* 48:2283-7 (2004), which are hereby incorporated by reference in their entirety) was the only bacterial strain used in these experiments. 1 µL of *S. aureus* Xen29 was taken from a frozen stock and grown in 10 mL of LB medium at 37° C. on a rotating platform at 200 rpm for 12 hours to mid-log phase. The bacteria were then diluted in LB medium to 1000 cfu/mL and 100 µL of the diluted suspension was added to wells of a flat-bottomed microtiter (with cover) designated for the addition of the antibodies and controls. Each anti-Gmd and control antibody was diluted into LB from stocks about 1 mg/mL in PBS and sterilized through a 0.2µ filter. 100 µL of each antibody was added to designated quadruplicate wells. Plates were then incubated at 37° C. and light scattering was measured at 490 and 670 nm at t=0, 5, 7, 9, 11, 13, 15 hours on a microtiter plate reader. A final time point was taken some time after 24 hours to confirm the measured plateau values.

The five antibodies were purified by affinity chromatography on Protein G-Agarose, concentrated to 1 mg/mL in PBS and dialyzed to remove preservatives such as $NaN_3$ and antibiotics that might interfere in the assay. 100 cfu of *S. aureus* strain Xen29 from a mid-log phase culture were placed in each microtiter well in LB medium along with 100 µL of each antibody or control (also in LB medium) at 50 µg/mL ($\sim 3\times 10^{-7}$ M). Growth was monitored by measuring light scattering at 490 and 670 nm at intervals over 26 hours.

Figure 8:
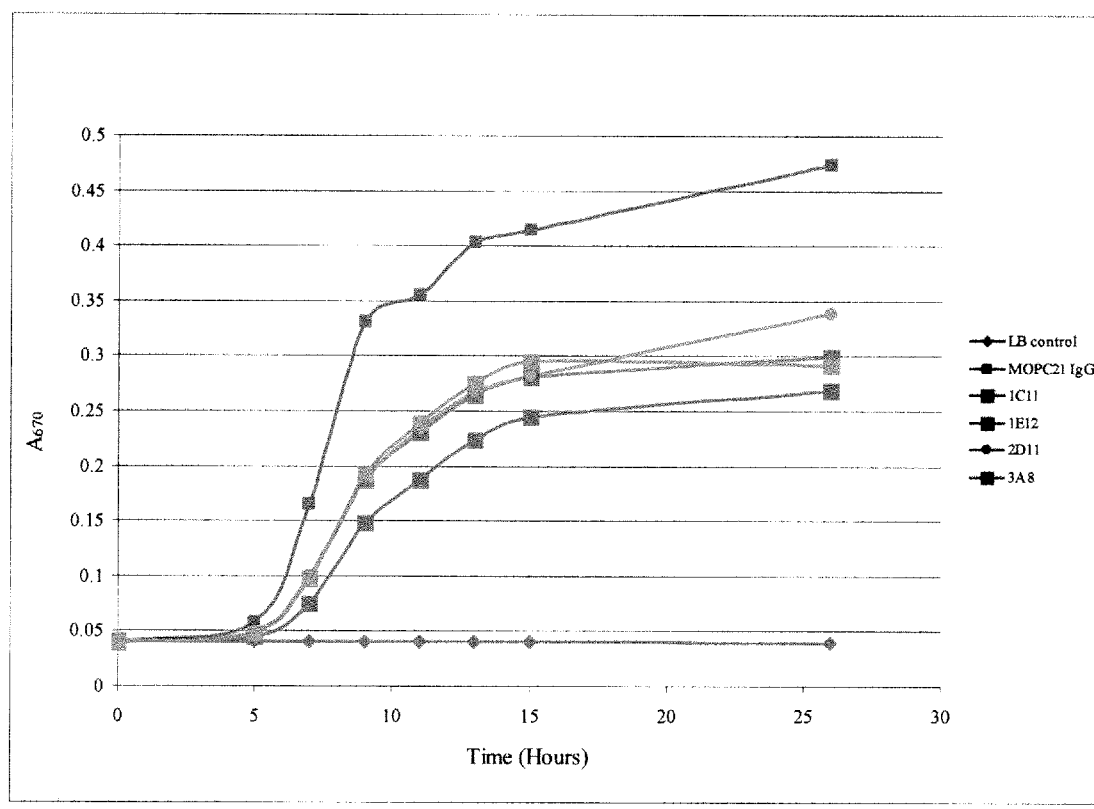
FIG. 8 shows the in vitro growth of *S. aureus* Xen29 in the presence of anti-Gmd monoclonal antibodies (anti-Gmd mAb). 100 cfu of Xen29 from a culture in log-phase growth were incubated at 37° C. with anti-Gmd monoclonal antibodies 1C11, 1E12, 2D11, and 3A8, 50 μg/mL in LB medium. Growth was monitored by light scattering at both 670 and 490 nm at the indicated intervals. MOPC21 is the isotype-matched control antibody.

Apparent reduction in the growth of *S. aureus* was observed by anti-Gmd monoclonal antibodies. As depicted in FIG. 8, four of the antibodies depressed the growth-related increase in light scattering of Xen29. The four antibodies that reduced light scattering all did so to the same degree while the isotype-matched control (MOPC21) was identical to Xen29 grown in the absence of any antibody. The fifth antibody, 3H6, also demonstrated similar behavior in a separate experiment.

It was also observed that the alteration of Xen29 growth-related light scattering is dose-dependent and consistent with high affinity interaction between monoclonal antibodies and native Gmd. The critical decision in addressing dose-dependence of the observed growth alteration of Xen29 was whether the apparent reduction in Xen29 growth was only partially revealed because the concentration of antibody was too low or the maximum effect was already observed and higher concentrations would have no further effect.

Figure 9:
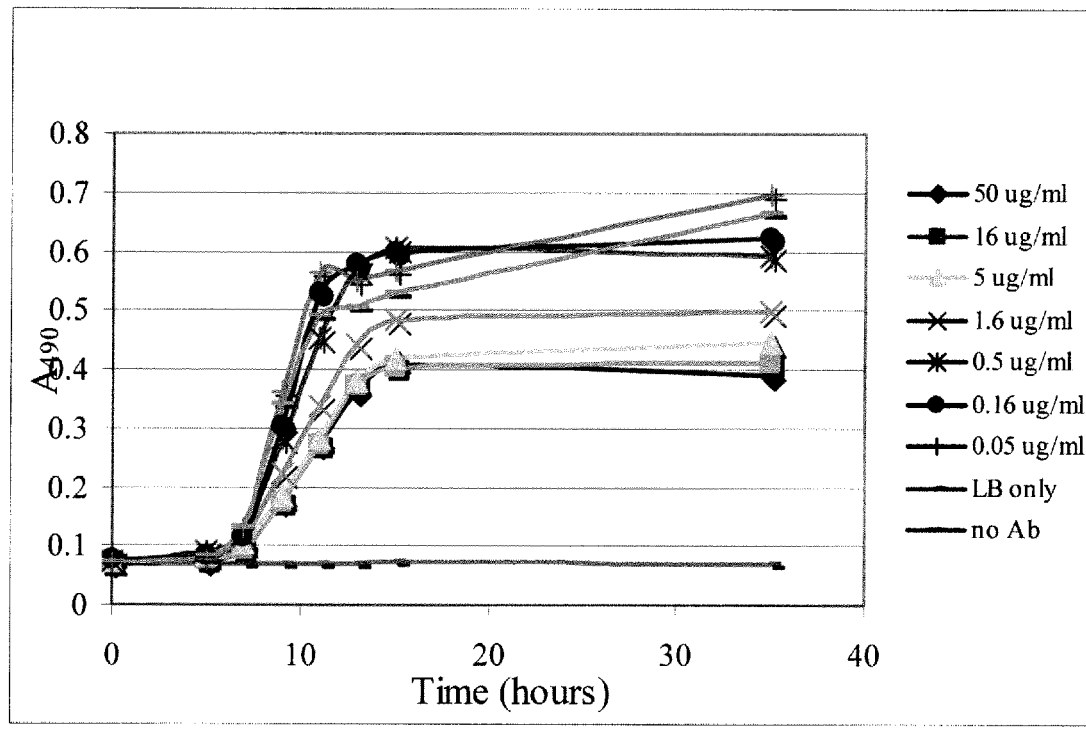
FIG. 9 shows the dose-dependent effect of anti-Gmd mAb 1C11 on in vitro *S. aureus* growth. 100 cfu of Xen29 from a culture in log-phase growth were incubated at 37° C. with a range of concentrations of anti-Gmd mAb 1C11 in LB medium. Growth was monitored by light scattering at both 670 and 490 nm at the indicated intervals.

Because four of the antibodies had the same magnitude of effect and 50 µg/mL ($3\times 10^{-7}$ M) was a very high concentration, the antibody levels were titrated down from 50 µg/mL in serial $10^{0.5}$ dilutions. Representative data is presented in FIG. 9. Monoclonal antibody 1C11 altered the growth of Xen 29 to the same degree at 50, 16 and 5 µg/mL, partially at 1.6 ($\sim 1\times 10^{-8}$ M), and was not different from the irrelevant antibody MOPC21 at 0.5 ug/mL (FIG. 10). Essentially identical results were obtained for mAbs 2D11, 1E12 and 3A8.

Results for the isotype-matched control antibody MOPC21 are presented in FIG. 10. The growth curves were essentially identical to the no antibody control. The slight elevation of the 50 µg/mL samples was due to their placement in outside wells in the microtiter plate (edge effect).

Assuming that the inhibition of Gmd is due to a high degree of antibody binding, then an estimate assuming that about ten times the $K_d$ is required places the operational affinity for the Gmd in the vicinity of 1 nM.

These data indicate that the four anti-Gmd mAbs inhibit Gmd activity, leading to a change in the in vitro growth pattern of Xen29, but they have no effect on the doubling time. The inhibition of Gmd activity leads to failed cytokinesis, i.e., the genome and cell membranes divide normally, but the cell walls fail to separate leading to large clusters of aggregated cells (Sugai et al., "Identification of Endo-beta-N-acetylglucosaminidase and N-acetylmuramyl-L-alanine Amidase as Cluster-dispersing Enzymes in *Staphylococcus aureus*," *J Bacteriol* 177:1491-6 (1995), which is hereby incorporated by reference in its entirety). This change is detectable by light scattering because there are fewer (albeit larger) scattering centers than when the Xen29 cells divide freely.

The antibodies of the present invention have already been shown to satisfy several key criteria. These are high affinity IgG antibodies produced by the parental hybridomas at robust levels (~50 µg/mL in static culture). They recognize conserved epitopes and consequently some or most will recognize Gmd from the majority of *S. aureus* strains. In addition, these experiments provide evidence that these monoclonal antibodies recognize native Gmd and not merely the recombinant His-Gmd that was used as the immunogen, and that they act as Gmd inhibitors. The monoclonal antibodies all exhibit Gmd-inhibitory activity of between about 70 to about 80 percent. This level of Gmd-inhibitory activity is rather surprising given that the five selected antibodies bind to epitopes located within the Gmd R3 domain rather than its catalytic domain.

Example 9—Monoclonal Antibodies Specific for Glucosaminidase from *Staphylococcus aureus* Use a Diverse Array of $V_H$ Genes To determine that the five monoclonal antibodies under investigation were unique, the sequences of the $V_H$ and $V_L$ genes were determined for the five candidate hybridomas (1C11, 1E12, 2D11, 3A8 and 3H6) identified in the preceding example.

Because there are considerable medical applications and advantages in the study of each of a set of monoclonal antibodies specific for the *S. aureus* glucosaminidase (Gmd), it is beneficial to identify hybridomas expressing identical antibodies (sibs). Five hybridomas were selected for sequence analysis of their Ig heavy and light chain genes.

Frozen aliquots of the five hybridoma cell lines were obtained from the vendor A&G Precision Antibody™ (9130 Red Branch Road, Suite U, Columbia, Md. 21045), who prepared the hybridomas at our direction. Cells were thawed, washed in DMEM with gentamicin and 10% FBS to remove DMSO, and then cultured in DMEM with gentamicin and 10% FBS. After a few days, cells were harvested by centrifugation and stored at −20° C. as a frozen pellet for subsequent RNA extraction.

RT-PCR amplification of the heavy chain mRNA was successful in the five hybridomas. Sequence analysis revealed that three different germ-line $V_H$ gene segments were used. Two of the hybridomas (2D11 and 3H6) used the same germ-line $V_H$ and J segments, but different D-segments and each displayed only modest sequence diversification from germ-line at the protein level. The heavy chain from the fifth hybridoma (1C11) did not initially amplify in RT-PCR even with PCR primers designed to amplify some of the more rarely used $V_H$ gene-segments. It can be inferred that it expressed an Ig $V_H$ gene distinct from the others.

Total RNA was extracted from freshly growing hybridoma cells and ~5 micrograms of RNA was reverse transcribed using the BioRad iScript kit. Aliquots of cDNA were PCR amplified with consensus primers for the 5'-ends of murine variable heavy and light regions paired with constant region primers. Strong products were obtained for 4/5 $V_H$ and 5/5 $V_L$ genes. The PCR products were gel purified and directly sequenced. All 4 $V_H$ products gave clean sequence, but 2/4 light chain products were mixed. The remaining two gave good sequences. The light chain derived from the cell line that failed to give a heavy chain product was not sequenced. The variable regions for those antibodies that failed to amplify in the initial experiments using framework 1 primers were successfully amplified using a different primer set that targets the secretory leader regions of the variable gene segments. These PCR products were also directly sequenced after purification.

Best matches for germ-line V-region genes were determined by using Ig BLAST (NCBI). The determined DNA sequence was translated into protein sequence by using an on-line program available at Expasy website. Sequence alignment of the 2D11 and 3H6 sequences was performed by visual inspection.

As noted above, eventually all of the five $V_H$ genes were successfully amplified and sequenced. Detailed DNA and protein sequence results for the five hybridomas are presented below.

Hybridoma 2D11 (Closest germ line match: J558.18.108) has the $V_H$ nucleotide sequence (SEQ ID NO: 21) as follows:

```
GAGGTGCAGCTGCAGGAGTCTGGACCTGTGCTGGTGAAGCCTGGGCTTC
AGTGAAGATGTCCTGTAAGGCTTCTGGATACACATTCACTGACTACTATA
TGAACTGGGTGAAGCAGAGCCATGGAAAGAGCCTTGAGTGGATTGGAGTT
ATTAATCCTTACAACGGTGATACTACCTACAGCCAGAAGTTCAAGGGCAA
GGCCACATTGACTGTTGACAAGTCCTCCAGCACAGCCTACATGGAGCTCA
ACAGCCTGACATCTGAGGACTCTGCAGTCTATTACTGTGCAAGAAATTAC
GACGAGTACTTCGATGTCTGGGGCACAGGGACCACGGTCACCGTCTCCTC
AGCCAAAACGACACCCCCATCTGTCTATCCACTGGCCCCTGGATCTGCTG
CCCAAACTAACTCCATGGTGACCCTGGGATGCCNGGTCAAGGGC
```

The 2D11 $V_L$ (Closest germ line match: at4) has the nucleotide sequence (SEQ ID NO: 22) as follows:

```
GATATTGTGATGACCCAGTCTCCAGCAATCATGTCTGCATCTCCAGGGGA
GAAGGTCACCATGACCTGCAGTGCCAGCTCAAGTGTAAGTTACATGTACT
GGTACCAGCAGAAGCCAGGATCCTCCCCCAGACTCCTGATTTATGACACA
TCCAACCTGGCTTCTGGAGTCCCTGTTCGCTTCAGTGGCAGTGGGTCTGG
GACCTCTTACTCTCTCACAATCAGCCGAATGGAGGCTGAGGATGCTGCCA
CTTATTACTGCCAGCAGTGGAGTAGTTACCCGCTCACGTTCGGT
```

The amino acid sequence of hybridoma 2D11 $V_H$ (SEQ ID NO: 1) is as follows:

```
EVQLQESGPVLVKPGASVKMSCKASGYTFTDYYMNWVKQSHGKSLEWIGV
INPYNGDTTYSQKFKGKATLTVDKSSSTAYMELNSLTSEDSAVYYCARNY
DEYFDVWGTGTTVTVSSAKTTPPSVYPLAPGSAAQTNSMVTLGCXVKG
```

The 2D11 $V_L$ has the amino acid sequence (SEQ ID NO: 8) as follows:

```
DIVMTQSPAIMSASPGEKVTMTCSASSSVSYMYWYQQKPGSSPRLLIYDT
SNLASGVPVRFSGSGSGTSYSLTISRMEAEDAATYYCQQWSSYPLTFG
```

Hybridoma 3H6 (Closest germ line match: J558.18.108) has the $V_H$ nucleotide sequence (SEQ ID NO: 23) as follows:

```
GAGGTGCAGCTGCAGGAGTCTGGACCTGTGCTGGTGAAGCCTGGGCTTC
AGTGAAGCTGTCCTGTAAGGCTTCTGGATACACATTCACTGACTACTTTA
TGAACTGGGTGAAGCAGAGCCATGGAAAGAGCCTTGAGTGGATTGGAGTT
ATTAATCCTTTCAACGGTGGTAATAGGTACAACCAGAACTTCAAGGGCAA
GGCCACATTGACTGTTGACAAGTCCTCCAGCACAGCCTACATGGAGCTCA
ACAGCCTGACATCTGAGGACTCTGCAGTCTATTACTGTGCAAGAGGGGAC
TATGACTCCCCCTGGTTTGATTACTGGGGCCAAGGGACTCTGGTCACTGT
CTCTGCAGCCAAAACGACACCCCCATCTGTCTATCCACTGGCCCCTGGAT
CTGCTGCCCAAACTAACTCCATGGTGACCCTGGGATGCCTGGTCAAGGGC
TATTCCCNGAGCCAGTG
```

The 3H6 $V_L$ (closest germ line match: cp9, JK1) has the nucleotide sequence (SEQ ID NO: 24) as follows:

```
CAGATGACACAGACTACGTCCTCCCTGTCTGCCTCTCTGGGAGACAGAGT
CACCATCAGTTGCAGTGCAAGTCAGGGCATTAGCAATTATTTAAACTGGT
ATCAGCAGAAACCAGATGGAACTGTTAAACTCCTGATCTATTACACATCA
AGTTTACACTCAGGAGTCCCATCAAGGTTCAGTGGCGGTGGGTCTGGGAC
AGATTATTCTCTCTCCATCAGCAACCTGGAACCTGAAGATATTGCCACTT
ACTATTGTCAGCAGTATAGTAAGCTTCCTTGGACGTTCGGTGGAGGCACC
AAGCTGGAAATCAAA
```

The amino acid sequence of hybridoma 3H6 $V_H$ (SEQ ID NO: 2) is as follows:

EVQLQESGPVLVKPGASVKLSCKASGYTFTDYFMNWVKQSHGKSLEWIGV
INPFNGGNRYNQNFKGKATLTVDKSSSTAYMELNSLTSEDSAVYYCARGD
YDSPWFDYWGQGTLVTVSAAKTTPPSVYPLAPGSAAQTNSMVTLGCLVKG
YSXSQ

The amino acid sequence of hybridoma 3H6 $V_L$ (SEQ ID NO: 9) is as follows:

QMTQTTSSLSASLGDRVTISCSASQGISNYLNWYQQKPDGTVKLLIYYTS
SLHSGVPSRFSGGGSGTDYSLSISNLEPEDIATYYCQQYSKLPWTFGGGT
KLEIK

Hybridoma 1E12 (Closest germ line match: 7183.46 VH7) has the $V_H$ nucleotide sequence (SEQ ID NO: 25) as follows:

GAGGTGCAGCTGCAGGAGTCTGGGGGAGGCTTCGTGAAGCCTGGAGGGTC
CCTGAAACTCTCCTGTGCAGCCTCTGGATTCACTTTCAGTACCTATGTCA
TGTCTTGGGTTCGCCAGACTCCGGAAAAGAGGCTGGAGTGGGTCGCAACC
ATTAGTGATGGTGGTGGTCATACTTACTATCTAGACAATGTAAAGGGCCG
ATTCACCATCTCCAGAGACAATGCCAAGAACAACCTGTACCTGCACATGA
GCCATCTGAAGTCTGAGGACACAGCCATGTATTACTGTGCAAGAGCTTAC
TACGGTAGTAGTTACGACGCTATGGACTACTGGGGTCAAGGAACCTCAGT
CACCGTCTCCTCAGCCAAAACGACACCCCCATCTGTCTATCCACTGGCCC
CTGGATCTGCTGCCCAAACTAACTCCATGGTGACCCTGGGATGCCTGGTC
AAGGGC

The 1E12 $V_L$ (Closest germ line match: ai4) has the nucleotide sequence (SEQ ID NO: 26) as follows:

GATATTGTGATCACCCAGTCTCCAGCAATCATGTCTGCATCTCTAGGGGA
ACGGGTCACCATGACCTGCACTGCCAGCTCAAGTGTAAGTTCCAGTTACT
TACACTGGTACCAGCAGAAGCCAGGATCCTCCCCCAAACTNTGGATTTAT
AGCACATCCAACCTGGCTTCTGGAGTCCCAGCTCGCTTCAGTGGCAGTGG
GTCTGGGACCTCTTACTCTCTCACAATCAGCAGCATGGAGGCTGAAGATG
CTGCCACTTATTACTGCCACCAGTATCATCGTTCCCCATGGACGTTCGGT
GGAGGCACC

The amino acid sequence of hybridoma 1E12 $V_H$ (SEQ ID NO: 3) is as follows:

EVQLQESGGGFVKPGGSLKLSCAASGFTFSTYVMSWVRQTPEKRLEWVAT
ISDGGGHTYYLDNVKGRFTISRDNAKNNLYLHMSHLKSEDTAMYYCARAY
YGSSYDAMDYWGQGTSVTVSSAKTTPPSVYPLAPGSAAQTNSMVTLGCLV
KG

The 1E12 $V_L$ has the amino acid sequence (SEQ ID NO: 10) as follows:

DIVITQSPAIMSASLGERVTMTCTASSSVSSSYLHWYQQKPGSSPKXWIY
STSNLASGVPARFSGSGSGTSYSLTISSMEAEDAATYYCHQYHRSPWTFG
GGT

Hybridoma 3A8 (Closest germ line match: VHJ606.4.8.2) has the $V_H$ nucleotide sequence (SEQ ID NO: 27) as follows:

GAGGTGCAGCTGCAGGAGTCTGGAGGAGGCTTGGTGCAACCTGGAGGATC
CATGAAACTCTCTTGTGCTGCCTCTGGATTCACTTTTAGTGACGCCTGGA
TGGACTGGGTCCGCCAGTCTCCAGAGAAGGGGCTTGAGTGGGTTGCTGAA
ATTAAAGACAAAACTAATAATCATGCAACATACTATGCTGAGTCTGTGAA
AGGGAGGTTCACCATCTCAAGAGATGTTTCCAAAAGTCGTGTCTTCCTGC
AAATGAACAGCTTAAGACCTGAAGACACTGGCATTTATTACTGTACGTCT
GGGCCATATTTTGACTACTGGGGCCAAGGCACCACTCTCACAGTCTCCTC
AGCCAAAACGACACCCCCATCTGTCTATCCACTGGCCCCTGGATCTGCTG
CCCAAACTAACTCCATGGTGACCCTGGGATGCCTGGTCAAGGGCTATTTC
CCTGAG

The 3A8 $V_L$ (closest germ line match: KV 19-25, JK2) has the nucleotide sequence (SEQ ID NO: 28) as follows:

GACATTGTGATGACCCAGTCTCACAAATTCATGTCCACATCAGTAGGAGA
CAGGGTCAGCATCACCTGCAAGGCCAGTCAGGACGTGAGTACTGCTGTAG
CCTGGTATCAACAAAAACCAGGGCAATCTCCTAAACTACTGATTTACTGG
ACATCCACCCGGCACACTGGAGTCCCTGATCGCTTCACAGGCAGTGGATC
TGGGACAGATTTTACTCTCACCATCAGCAGTGTGCAGGCTAAAGACCTGG
CACTTTATTACTGTCAGCAACATTATACCACTCCGTACACGTTCGGAGGG
GGGACCAAGCTGGAAATAAAA

The amino acid sequence of hybridoma 3A8 $V_H$ (SEQ ID NO: 4) is as follows:

EVQLQESGGGLVQPGGSMKLSCAASGFTFSDAWMDWVRQSPEKGLEWVAE
IKDKTNNHATYYAESVKGRFTISRDVSKSRVFLQMNSLRPEDTGIYYCTS
GPYFDYWGQGTTLTVSSAKTTPPSVYPLAPGSAAQTNSMVTLGCLVKGYF
PE

The amino acid sequence of hybridoma 3A8 $V_L$ (SEQ ID NO: 11) is as follows:

DIVMTQSHKFMSTSVGDRVSITCKASQDVSTAVAWYQQKPGQSPKLLIYW
TSTRHTGVPDRFTGSGSGTDFTLTISSVQAKDLALYYCQQHYTTPYTFGG
GTKLEIK

Hybridoma 1C11 (closest germline match: VH 9-15, DST4-057B1-6, JH3) has the $V_H$ nucleotide sequence (SEQ ID NO: 29) as follows:

```
CAGATCCAGTTGGTACAGTCTGGACCTGAGCTGAAGAAGCCTGGAGAGAC

AGTCAAGATCTCCTGCAAGGCTTCTGGGTATACCTTCACAACGTATGGAA

TGAGCTGGGTGAATCAGGCTCCAGGAAAGGGTTTAAAGTGGATGGGCTGG

ATAAACACCTACTCTGGAGTGCCAACATATGCTGATGACTTCAAGGGACG

GTTTGTCTTCTCTTTGGAAACCTCTGCCAGCACTGCCTATTTGCAGATCA

ACAACCTCAAAAATGAGGACACGGCTACATATTTCTGTGCAAGAGAGGAG

TACAGCTCAGGCTACGCGGCCTGGTTTCCTTACTGGGGCCAAGGGACTCT

GGTCACTGTCTCTGCA
```

The 1C11 $V_L$ (closest germ line match: VK23-43, JK5) has the nucleotide sequence (SEQ ID NO: 30) as follows:

```
GATATTGTGCTAACTCAGTCTCCAGCCACCCTGTCTGTGACTCCAGGAGA

TAGCGTCAGTCTTTCCTGCAGGGCCAGCCAAAGTATTAGCAACAACCTAC

ACTGGTATCAACAAAAATCACATGAGTCTCCAAGGCTTCTCATCGAATAT

GCTTCCCGGTCCATCTCTGGGATCCCCTCTAGGTTCAGTGGCGGTGGATC

AGGGACAGATTTCACTCTCAGTATCAACAGTGTGGAGTCTGAAGATTTTG

GATTGTATTTCTGTCAACAGAGTAACAGCTGGCCGCTCACGTTCGGTGCT

GGGACCAAGCTGGAGCTGAAA
```

The amino acid sequence of hybridoma 1C11 $V_H$ (SEQ ID NO: 5) is as follows:

```
QIQLVQSGPELKKPGETVKISCKASGYTFTTYGMSWVNQAPGKGLKWMGW

INTYSGVPTYADDFKGRFVFSLETSASTAYLQINNLKNEDTATYFCAREE

YSSGYAAWFPYWGQGTLVTVSA
```

The amino acid sequence of hybridoma 1C11 $V_L$ (SEQ ID NO: 12) is as follows:

```
DIVLTQSPATLSVTPGDSVSLSCRASQSISNNLHWYQQKSHESPRLLIEY

ASRSISGIPSRFSGGGSGTDFTLSINSVESEDFGLYFCQQSNSWPLTFGA

GTKLELK
```

From the obtained sequences the closest fit for germ line $V_H$ and $V_L$ gene segments was determined as shown in Table 1.

TABLE 1

Germline Matches for Sequenced Hybridoma Cell Lines

| Hybridoma | Germ Line $V_H$ | Germ Line $V_L$ |
|---|---|---|
| 1C11 | VH 9-15, DST4-C57Bl-6, JH3 | VK23-43, JK5 |
| 1E12 | 7183.46 VH7 | ai4 |
| 2D11 | J558.18.108 | at4 |
| 3A8 | VHJ606.48.2 | KV 19-25, JK2 |
| 3H6 | J558.18.108 | cp9, JK1 |

Each of the five hybridomas expressed a unique $V_H$ gene. FIG. 11 shows the alignment of the four initially sequenced $V_H$ genes, and FIG. 13 shows the alignment of all five sequenced $V_H$ genes. FIG. 15 shows the alignment of the sequenced $V_H$ genes for 1C11 and 3A8 only.

FIG. 12 shows the alignment of the two initially obtained $V_L$ genes. FIG. 14A shows the alignment of all five sequenced $V_l$ genes, whereas FIG. 14B all five sequenced $V_l$ genes except of that for 1C11.

The fact that one hybridoma (1C11) did not yield a PCR product with the initial primers that amplify the most common $V_H$ genes suggests that it uses a fourth $V_H$ gene segment not identical to any of the others identified here. Two of the hybridomas used the same $V_H$ germ line gene, but are not identical. Hybridomas 2D11 and 3H6 both used the germ line $V_H$ gene segment J558.18.108. Their sequences are compared with the germ line gene in FIG. 11. Inspection of the sequence reveals that there is only one difference in CDR1, four in CDR2 and five in CDR3 (including gaps).

The five hybridomas are not sibs and among them at least four $V_H$ germ line genes were utilized.

Example 10—Inhibition of *S. aureus* Gmd Enzymatic Activity by mAbs 1C11, 2D11, 3H6, 1E12, and 3A8

The method of measurement of Gmd enzymatic activity is essentially the method of Mani et al. (Mani et al., "Isolation and Characterization of Autolysis-Defective Mutants of *Staphylococcus aureus* Created by Tn917-lacZ Mutagenesis" J. Bacteriol. 175(5): 1493-1499 (1993)). Lyophilized and resuspended *Micrococcus lysodeikticus* were degraded by the action of the Gmd resulting in a reduction in light scattering at 490 nm. 100 µL of sample containing Gmd diluted in phosphate-buffered saline with 0.05% Tween 20 (PBST) was added to the wells of a 96-well microtiter plate. 100 µL of a 0.15% (w/v) suspension of *Micrococcus lysodeikticus* was added to each well and the light scattering was measured immediately to establish the initial $A_{490}$, typically about 0.8. The plate was then incubated at 37° C. and light scattering was re-measured at 30 and 60 minutes. Reduction in $A_{490}$ at 60 minutes was taken as the measure of Gmd activity. The modest background rate (no Gmd) was subtracted. This method does not distinguish Gmd activity from lysozyme activity.

To measure inhibition of Gmd enzymatic activity the Gmd was pre-titered to determine the concentration that will yield about a 50% reduction in $A_{490}$ in 60 minutes. Then, 50 µL of antibody diluted in PBST was added to each well of a 96-well microtiter plate followed by 50 µL of appropriately diluted Gmd, and the mixtures were allowed to incubate for 5 or more minutes, and finally 100 µL of 0.15% *Micrococcus lysodeikticus* was added and the initial $A_{490}$ was measured. The plate was then incubated at 37° C. and the $A_{490}$ was measured at 30 and 60 minutes. Percent inhibition was calculated as $100*(1-(\Delta_{60}A_{490}$ inhibitor/$\Delta_{60}A_{490}$ no inhibitor control)).

Figure 18:
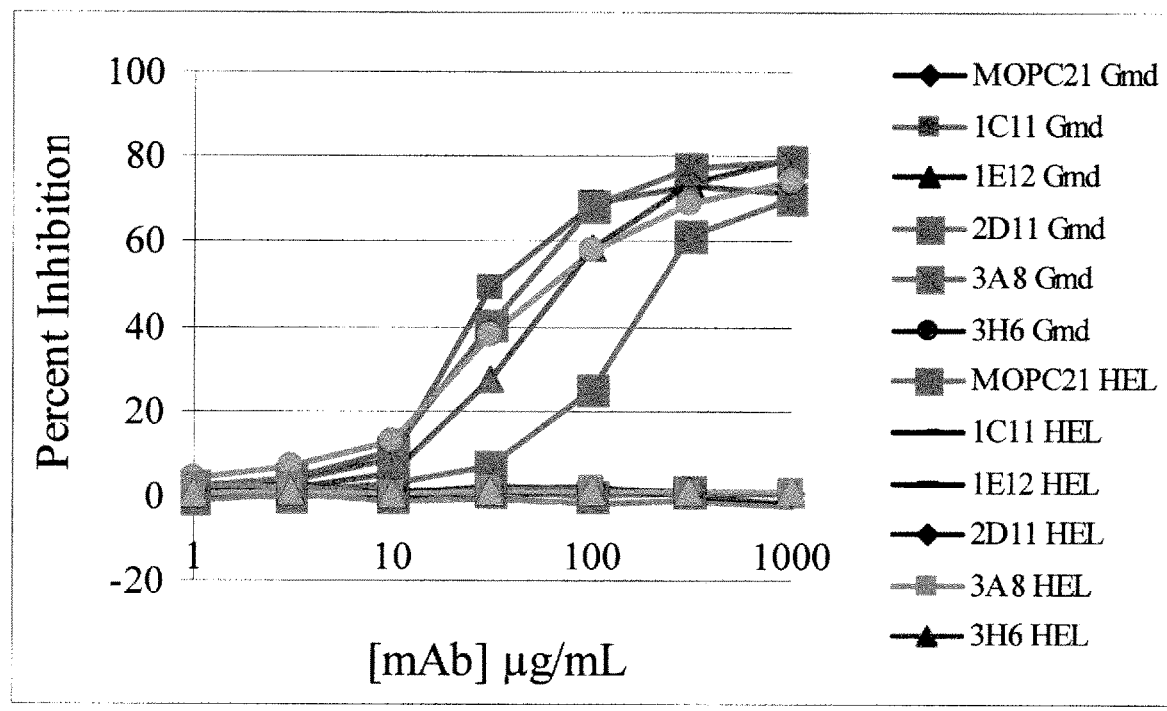
FIG. 18 shows the inhibition of S. aureus His-Gmd (Gmd) and hen egg lysozyme (HEL) by the five anti-Gmd monoclonal antibodies with MOPC21 as an isotype-matched negative control. The concentration of the antibody in μg/mL is listed on the x-axis; the inhibition of enzyme activity in percentage (%) is listed on the Y-axis. All five anti-Gmd mAbs (1C11, 1E12, 2D11, 3A8, and 3H6) inhibit Gmd activity, but have no effect on HEL activity, and MOPC21 (negative control) does not inhibit either enzyme.

In FIG. 18, serial dilutions of each of the five antibodies plus the isotype-matched negative control MOPC21 were assessed for their ability to inhibit the catalytic activity of recombinant *S. aureus* His-Gmd (Gmd) or hen egg lysozyme (HEL). Each of the five anti-Gmd monoclonal antibodies inhibited His-Gmd activity by 75-80%, while displaying no inhibitory activity with HEL. MOPC21 had no inhibitory activity with either enzyme. The degree of inhibition of His-Gmd has not been observed to exceed 80% by these five antibodies. High, though partial, inhibition is one of the characteristics of this group of antibodies.

Figure 19:
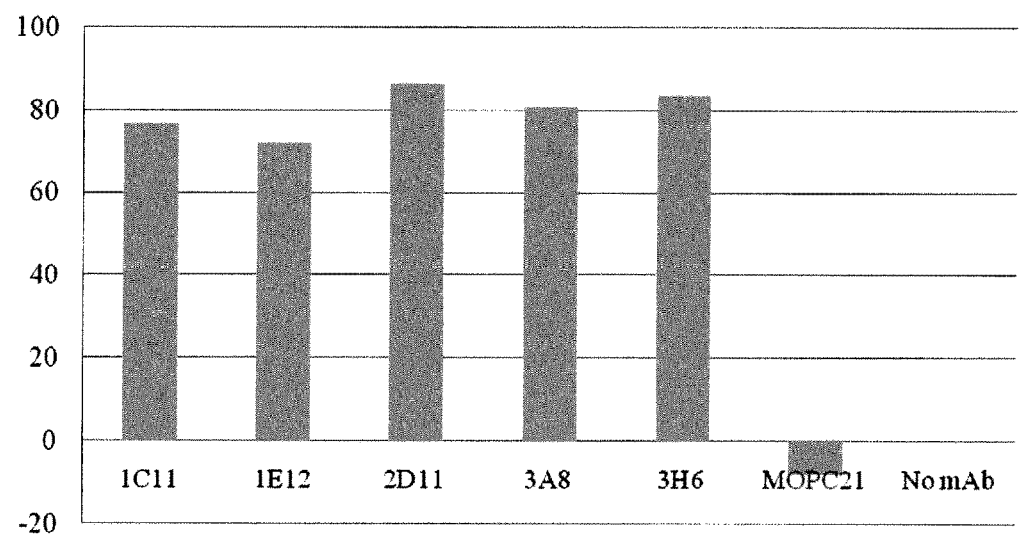
FIG. 19 shows inhibition of native Gmd by the five anti-His-Gmd mAbs 1C11, 1E12, 2D11, 3A8, and 3H6. Each antibody was added at a concentration of 100 μg/mL. All five are potent inhibitors and inhibit the native enzyme to about the same degree as they inhibit the recombinant Gmd-His. The isotype-matched (IgG1) antibody control MOPC21 had no effect on Gmd enzymatic activity.

The ability of the five antibodies to inhibit the native Gmd enzyme secreted by *S. aureus* strain UAMS-1 is depicted in FIG. 19. As with the recombinant Gmd, the native Gmd was inhibited about 80% by each antibody. By the measure of enzyme inhibition, the antibodies react similarly with both the native and recombinant Gmds.

An SEM analysis of anti-Gmd activity for several monoclonal antibodies is shown in FIGS. 20C-D. Xen29 *S. aureus* was grown for 12 hours in Luria-Bertani broth to achieve a mid-log growth suspension, and then 10,000 CFU were incubated with: (FIGS. 20A-B) no antibody, (FIG. 20C) 50 µg/ml 1E12, or (FIG. 20D) 50 µg/ml 1C11 for 1 hour. Samples were then plated onto sterile silicon chips, fixed, dehydrated, and coated with gold for visualization by scanning electron microscopy. Micrographs (FIGS. 20C-D) illustrate the effect of anti-Gmd antibody, promoting formation of large clusters and cell-independent lysis (arrows) of approximately 20% of the cells.

Figure 21A:
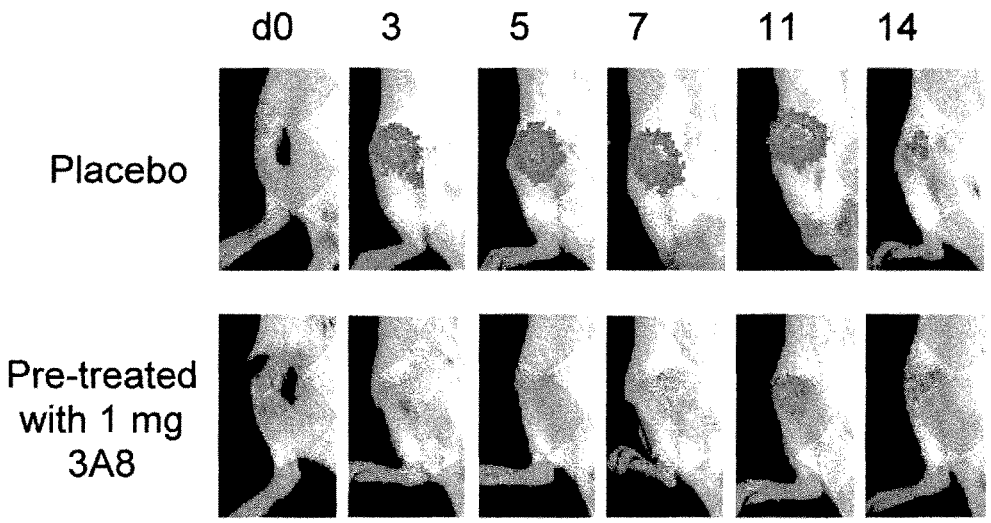
FIGS. 21A-C show that passive immunization with monoclonal antibody 3A8 inhibits S. aureus growth in vivo and protects mice from implant-associated osteomyelitis. The mice were imaged to assess bioluminescence on days 0, 3, 5, 7, 11, and 14, and images with the BLI heat map from a representative animal in each group are shown in FIG. 21A. The BLI values on day 3 for each mouse in the study are shown with the mean for each group (FIG. 21B, p=0.02). X-rays from a representative animal in each group obtained on day 14 are shown to illustrate the osteolytic lesion (arrow) in the placebo mouse, which was not present in the anti-Gmd treated animals (FIG. 21C).
Figure 21B:
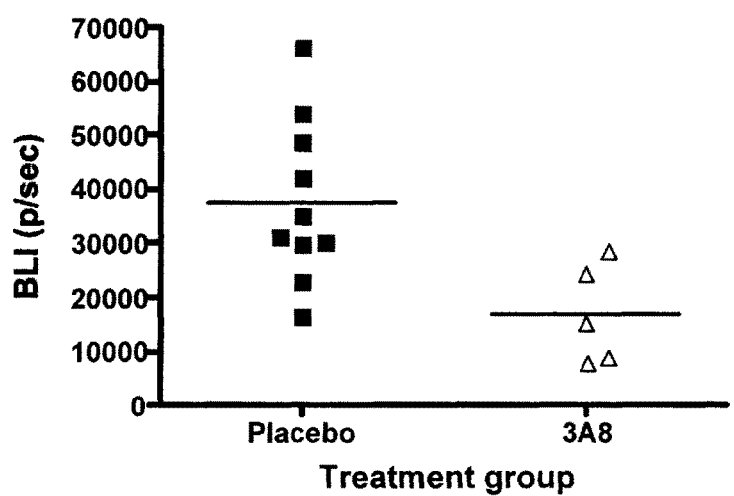
Figure 21C:
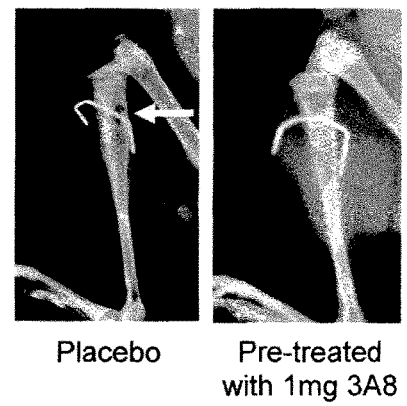
Figure 22A:
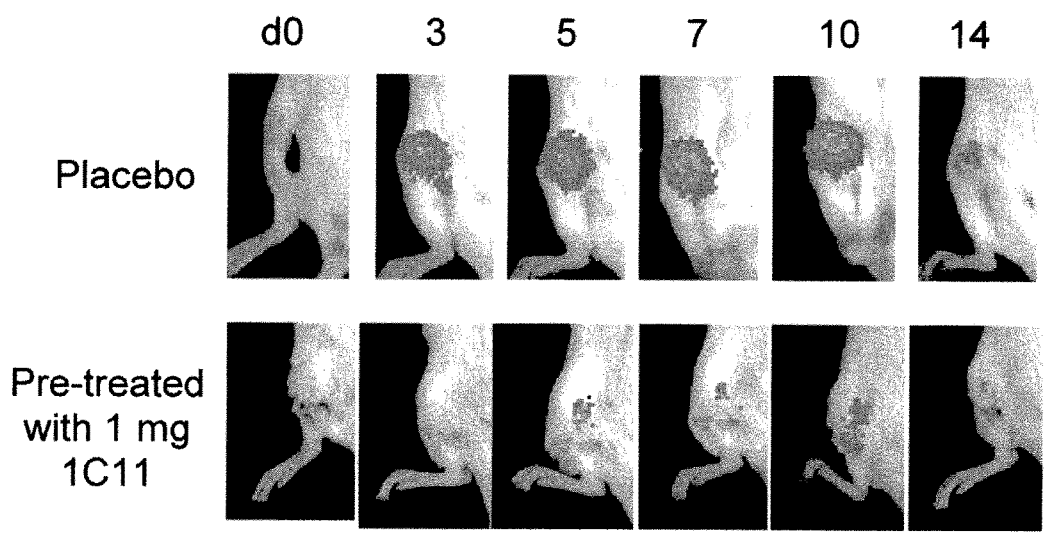
FIGS. 22A-C show that passive immunization with monoclonal antibody 1C11 inhibits S. aureus growth in vivo and protects mice from implant-associated osteomyelitis. The mice were imaged to assess bioluminescence on days 0, 3, 5, 7, 10, and 14, and images with the BLI heat map from a representative animal in each group are shown in (FIG. 22A). The BLI values on day 3 for each mouse in the study are shown with the mean for each group (FIG. 22B). X-rays from a representative animal in each group obtained on day 14 are shown to illustrate the osteolytic lesion (arrow) in the placebo mouse, which was not present in the anti-Gmd treated mouse (FIG. 22C).
Figure 22B:
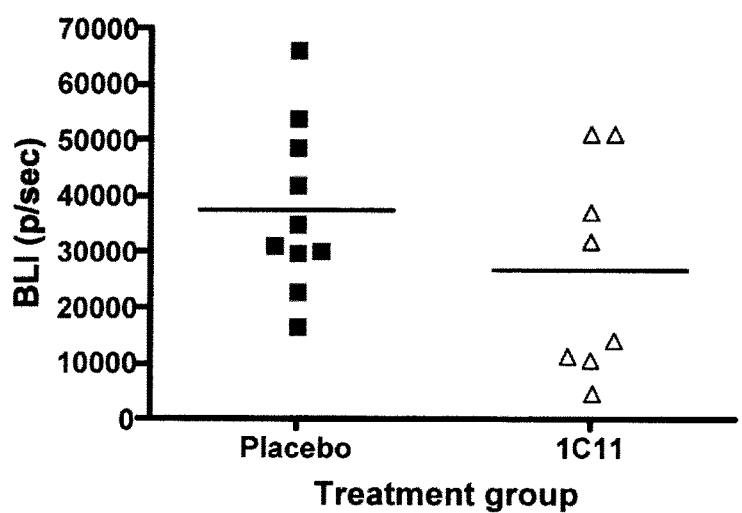
Figure 22C:
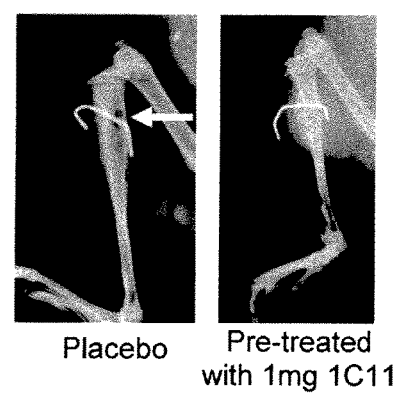

Example 11—Passive Vaccine Containing Anti-Gmd mAbs Inhibits *Staphylococcus aureus* In Vivo Following Orthopedic Implant in Mouse OM Model The OM model with trans-tibial pin (see Examples 1 and 6) was used to assess the ability of candidate mAbs 1C11 and 3A8 to inhibit *S. aureus* growth in vivo. Briefly, five week old female BALB/cJ mice received an intraperitoneal injection of saline (n=10) or 1 mg of purified 3A8 anti-Gmd antibody (n=5) in 0.25 ml saline or 31C11 A8 anti-Gmd antibody (n=5) in 0.25 ml saline 3 days prior to surgery. At surgery, the mice received a transtibial implant containing 500,000 CFU of Xen29 *S. aureus*. The mice were imaged to assess bioluminescence on days 0, 3, 5, 7, 10 or 11, and 14, and images with the BLI heat map from a representative animal in each group are shown in FIGS. 21A and 22A. Of note is the absence of a BLI signal in the anti-Gmd 3A8 animal until day 11 and 1C11 animal until day 5, presumably when the antibody titer decreased below the effective concentration. The BLI values on day 3 for each mouse in the study are shown with the mean for each group (FIG. 21B, p=0.02; FIG. 22B). For 1C11, it is interesting to note that this therapy cured 50% of the animals at day 3. X-rays from a representative animal in each group obtained on day 14 is shown to illustrate the osteolytic lesion (arrow) in the placebo mouse, which was not present in the anti-Gmd treated animals (FIGS. 21C, 22C).

Example 12—Generation of Humanized Antibody

The variable regions of the light and heavy chains of the 1C11 antibody were re-amplified from the purified hybridoma PCR product described in Example 9 using primers to permit cloning into the human antibody expression vectors described by Tiller et al. ("Efficient Generation of Monoclonal Antibodies from Single Human B Cells by Single Cell RT-PCR and Expression Vector Cloning," *J. Immunol.* Methods 329(1-2):112-24 (2008), which is hereby incorporated by reference in its entirety). Plasmids containing the 1C11 light and heavy chain variable regions and human kappa and IgG1 constant regions were prepared and co-transfected into HEK293 cells. After 3 days, the medium was removed from the cells and assayed for the presence of human IgG and for binding to immobilized Gmd protein by ELISA. Bound antibody was detected using a goat anti-Human IgG antibody coupled to horseradish peroxidase and 3,3', 5, 5' tetramethylbenzidene substrate.

Figure 23:
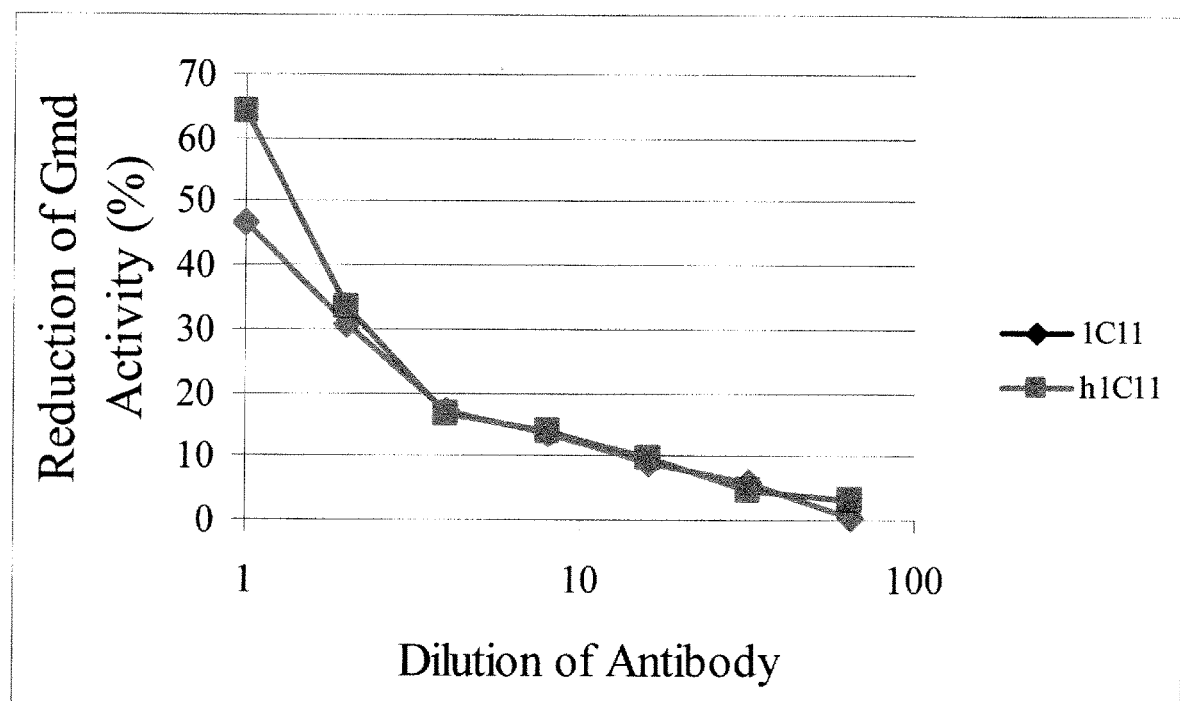
FIG. 23 is a graph comparing the anti-Gmd inhibitory activity of mouse monoclonal 1C11 with the humanized chimeric monoclonal derived from 1C11. The human:mouse chimeric IgG1 of 1C11 (h1C11) retains the ability to inhibit His-Gmd. The percent inhibition of His-Gmd activity on the Y-axis is displayed as a function of dilution of the antibody preparation on the X-axis. The mouse 1C11 concentration was 10 μg/mL; the concentration for chimeric h1C11 was not known for the assay shown.

To establish that the human:mouse chimeric 1C11 (h1C11) reacted with Gmd as well as the parental mouse 1C11, each was tested for its ability to inhibit the enzymatic activity of His-Gmd. Both h1C11 and mouse 1C11 displayed nearly identical inhibitory activity (FIG. 23), thereby demonstrating that the chimeric IgG molecule retained the binding activity of the parent.

A similar procedure will be performed using the human CDR1 and CDR2 homologs of 1C11 identified in FIGS. 17A-B, and a CDR3 region from one or more candidate D regions including, without limitation, IGHD5-5, 18, and 12*01.

The humanized 1C11 antibody and antibody comprising the human CDR1 and CDR2 homologs of 1C11 can be utilized in a phase I clinical trial in elderly patients (>65 yrs) undergoing primary total joint replacement.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. An isolated humanized monoclonal antibody or an antigen binding portion thereof that binds specifically to a *Staphylococcus aureus* glucosaminidase (Gmd) and comprises (i) the complementarity determining region sequences of the $V_H$ domain of SEQ ID NO: 1 and the $V_L$ domain of SEQ ID NO: 8, or (ii) the complementarity determining region sequences of the $V_H$ domain of SEQ ID NO: 2 and the $V_L$ domain of SEQ ID NO: 9.

2. The monoclonal antibody or antigen binding portion according to claim 1, which binds Gmd comprising the amino acid sequence of SEQ ID NO: 36.

3. The monoclonal antibody or antigen binding portion according to claim 1, wherein the monoclonal antibody or antigen binding portion inhibits in vivo growth of *S. aureus*.

4. The monoclonal antibody or antigen binding portion according to claim 3, wherein the *S. aureus* is methicillin resistant.

5. The monoclonal antibody or antigen binding portion according to claim 1, which comprises (i) the sequences of amino acid residues 31-35, 50-66, and 99-106 of SEQ ID NO: 1 and the sequences of amino acid residues 24-30, 49-55, and 88-94 of SEQ ID NO: 8; or (ii) the sequences of amino acid residues 31-35, 50-66, and 100-108 of SEQ ID NO: 2 and the sequences of amino acid residues 22-29, 48-54, and 87-93 of SEQ ID NO: 9.

6. The antigen binding portion according to claim 1.

7. The antibody binding portion according to claim 6, wherein the antigen binding portion comprises a Fab fragment, Fv fragment, or single-chain antibody.

8. A cell line that expresses a monoclonal antibody or antigen binding portion according to claim 1.

9. A pharmaceutical composition comprising a carrier and the monoclonal antibody or antigen binding portion according to claim 1.

10. The pharmaceutical composition according to claim 9 further comprising an antibiotic agent or immunotherapeutic agent.

11. The pharmaceutical composition according to claim 10, wherein the antibiotic agent is selected from the group consisting of vancomycin, tobramycin, cefazolin, erythromycin, rifampin, gentamycin, fusidic acid, minocycline, co-trimoxazole, clindamycin, linezolid, quinupristin-dalfopristin, daptomycin, tigecycline, dalbavancin, telavancin, oritavancin, ceftobiprole, ceftaroline, iclaprim, and the carbapenem CS-023/RO-4908463.

12. The pharmaceutical composition according to claim 10, wherein the immunotherapeutic agent is tefibazumab or BSYX-A110.

13. A method of introducing an orthopedic implant into a patient comprising:
  administering to a patient in need of an orthopedic implant an effective amount of a monoclonal antibody according to claim 1; and
  introducing the orthopedic implant into the patient.

14. A method of treating *S. aureus* infection comprising:
  administering to a patient having a *S. aureus* infection an effective amount of a monoclonal antibody according to claim 1.

15. A method of treating osteomyelitis comprising administering to a patient having a *S. aureus* bone or joint infection an effective amount of the monoclonal antibody according to claim 1.

16. The antigen binding portion according to claim 5.

17. The antigen binding portion according to claim 16, wherein the antigen binding portion comprises a Fab fragment, Fv fragment, or single-chain antibody.

18. A cell line that expresses a monoclonal antibody or antigen binding portion according to claim 5.

19. A pharmaceutical composition comprising a carrier and the monoclonal antibody or antigen binding portion according to claim 5.

20. The pharmaceutical composition according to claim 19 further comprising an antibiotic agent or immunotherapeutic agent.

21. The pharmaceutical composition according to claim 20, wherein the antibiotic agent is selected from the group consisting of vancomycin, tobramycin, cefazolin, erythromycin, rifampin, gentamycin, fusidic acid, minocycline, co-trimoxazole, clindamycin, linezolid, quinupristin-dalfopristin, daptomycin, tigecycline, dalbavancin, telavancin, oritavancin, ceftobiprole, ceftaroline, iclaprim, and the carbapenem CS-023/RO-4908463.

22. The pharmaceutical composition according to claim 20, wherein the immunotherapeutic agent is tefibazumab or BSYX-A110.

23. An isolated monoclonal antibody or an antigen binding portion thereof that binds specifically to a *Staphylococcus aureus* glucosaminidase (Gmd) and comprises (i) the complementarity determining region sequences of the $V_H$ domain of SEQ ID NO: 1 and the $V_L$ domain of SEQ ID NO: 8, or (ii) the complementarity determining region sequences of the $V_H$ domain of SEQ ID NO: 2 and the $V_L$ domain of SEQ ID NO: 9.

* * * * *